United States Patent
Boger

(10) Patent No.: US 8,124,778 B2
(45) Date of Patent: *Feb. 28, 2012

(54) TRICYCLIC INHIBITORS OF FATTY ACID AMIDE HYDROLASE

(75) Inventor: Dale L. Boger, La Jolla, CA (US)

(73) Assignee: The Scripps Research Institute, La Jolla, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/600,736

(22) PCT Filed: May 30, 2008

(86) PCT No.: PCT/US2008/006913
§ 371 (c)(1),
(2), (4) Date: Apr. 30, 2010

(87) PCT Pub. No.: WO2008/150492
PCT Pub. Date: Dec. 11, 2008

(65) Prior Publication Data
US 2010/0216750 A1    Aug. 26, 2010

Related U.S. Application Data

(60) Provisional application No. 60/932,494, filed on May 31, 2007.

(51) Int. Cl.
C07D 413/00  (2006.01)
C07D 263/30  (2006.01)
A61K 31/44   (2006.01)
A61K 31/505  (2006.01)

(52) U.S. Cl. ............ 546/271.4; 548/235; 514/340; 514/374

(58) Field of Classification Search .......... None
See application file for complete search history.

(56) References Cited

U.S. PATENT DOCUMENTS
2004/0127518 A1  7/2004  Piomelli et al.
2006/0111359 A1  5/2006  Boger
2006/0167075 A1  7/2006  Pearson et al.

FOREIGN PATENT DOCUMENTS
WO  WO-2007/098142 A2  8/2007
WO  WO-2008/150492 A1  12/2008

OTHER PUBLICATIONS

Dondi, J. Org. Chem. 1987 vol. 52 pp. 3413-3420.*
Boger, D. et al., J. Med. Chem., 2005, vol. 48, 1849-56.*
Tavora de Albuquerque Silva, Mini-Reviews in Med. Chem., 2005, vol. 5, pp. 893-914.*
Patani, G. et al., Chem. Rev. 1996, vol. 96, pp. 3147-3176.*
Ettmayer, P. et al., J. Med. Chem., 2004, vol. 47 (10), pp. 2393-2404.*
"International Application Serial No. PCT/US2008/006913, International Search Report and Written Opinion Mailed Oct. 9, 2008", 9 pgs.
"European Application Serial No. 08768012.0, Supplementary European Search Report mailed Mar. 15, 2011", 5 pgs.
"European Application Serial No. 08768012.0, European Search Report Response filed Sep. 22, 2011", 5 pgs.

* cited by examiner

Primary Examiner — Janet Andres
Assistant Examiner — Heidi Reese
(74) Attorney, Agent, or Firm — Schwegman, Lundberg & Woessner, P.A.

(57) ABSTRACT

A series of substituted oxazole compounds having an alpha keto side chain at the 2 position and an aromatic, heteroaromatic or heterocycle substituent at the 5 position are disclosed. These compounds exhibit inhibition of fatty acid amid hydrolase and arc useful for treatment of malconditions involving that enzyme.

14 Claims, 11 Drawing Sheets

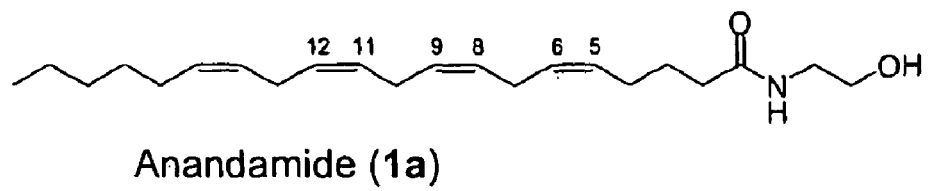
Anandamide (1a)
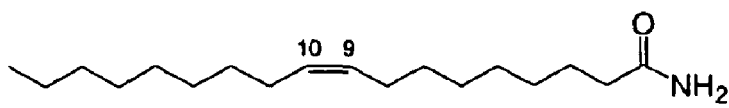
Oleamide (1b)
Fatty Acid Amide Hydrolase (FAAH)
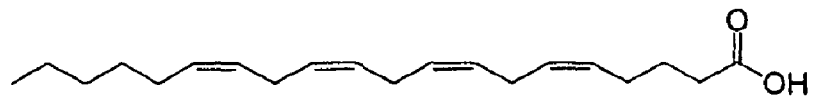
Arachidonic Acid (1c)
Oleic Acid (1d)
Figure 1

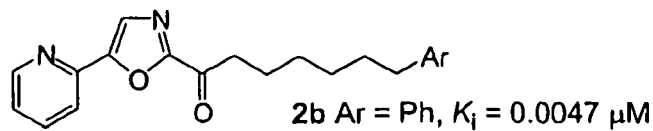

2b Ar = Ph, $K_i$ = 0.0047 μM

| compd | Ar | $K_i$, μM | compd | Ar | $K_i$, μM |
|---|---|---|---|---|---|
| 5a | 2-thienyl | 0.0043 ± 0.0008 | 5d | 2-naphthyl | 0.011 ± 0.001 |
| 5b | 3-thienyl | 0.0051 ± 0.0006 | 5e | 2-pyridyl | 0.12 ± 0.005 |
| 5c | 1-naphthyl | 0.0026 ± 0.003 | 5f | 3-pyridyl | 0.032 ± 0.032 |

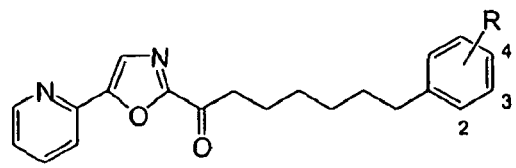

| compd | R | $K_i$, μM | compd | R | $K_i$, μM |
|---|---|---|---|---|---|
| 5g | 2-CH$_3$ | 0.0030 ± 0.0009 | 5x | 2-CF$_3$ | 0.004 ± 0.0001 |
| 5h | 3-CH$_3$ | 0.0033 ± 0.0001 | 5y | 3-CF$_3$ | 0.001 ± 0.0001 |
| 5i | 4-CH$_3$ | 0.0028 ± 0.0006 | 5z | 4-CF$_3$ | 0.004 ± 0.0007 |
| 5j | 2-OCH$_3$ | 0.0058 ± 0.0001 | 5aa | 2-CO$_2$CH$_3$ | 0.001 ± 0.0003 |
| 5k | 3-OCH$_3$ | 0.0025 ± 0.0005 | 5bb | 3-CO$_2$CH$_3$ | 0.0019 ± 0.0005 |
| 5l | 4-OCH$_3$ | 0.0062 ± 0.0007 | 5cc | 4-CO$_2$CH$_3$ | 0.0015 ± 0.0001 |
| 5m | 3-NH$_2$ | 0.030 ± 0.001 | 5dd | 2-CO$_2$H | >0.6 |
| 5n | 4-NH$_2$ | 0.0030 ± 0.0002 | 5ee | 3-CO$_2$H | >0.6 |
| 5o | 3-NHBOC | 0.0024 ± 0.0006 | 5ff | 4-CO$_2$H | >0.6 |
| 5p | 4-NHBOC | 0.0056 ± 0.0002 | 5gg | 2-Cl | 0.0019 ± 0.0001 |
| 5q | 2-F | 0.0017 ± 0.0002 | 5hh | 3-Cl | 0.0009 ± 0.00005 |
| 5r | 3-F | 0.0022 ± 0.0003 | 5ii | 4-Cl | 0.0027 ± 0.0001 |
| 5s | 4-F | 0.0032 ± 0.0005 | 5jj | 2,3-Cl$_2$ | 0.0009 ± 0.00005 |
| 5t | 2-SCH$_3$ | 0.0033 ± 0.0001 | 5kk | 2-SO$_2$CH$_3$ | 0.037 ± 0.0015 |
| 5u | 3-SCH$_3$ | 0.0042 ± 0.0003 | 5ll | 3-SO$_2$CH$_3$ | 0.0013 ± 0.0001 |
| 5v | 4-SCH$_3$ | 0.0025 ± 0.0001 | 5mm | 4-SO$_2$CH$_3$ | 0.019 ± 0.001 |
| 5w | 4-NO$_2$ | 0.0065 ± 0.0005 | | | |

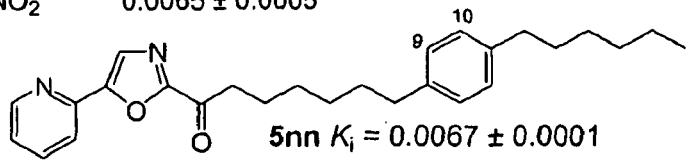

5nn $K_i$ = 0.0067 ± 0.0001

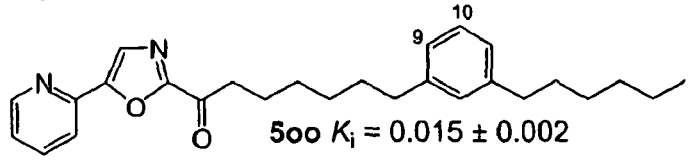

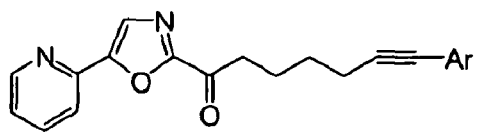
| compd | Ar | $K_i$, µM | compd | Ar | $K_i$, µM |
|---|---|---|---|---|---|
| 4e | 2-pyridyl | 0.28 ± 0.015 | 4pp | 4-pyridyl | 0.15 ± 0.008 |
| 4f | 3-pyridyl | 0.3 ± 0.018 | | | |
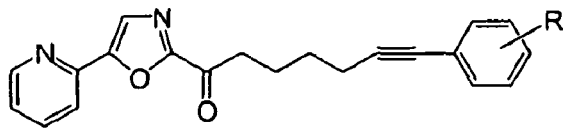
| compd | R | $K_i$, µM | compd | R | $K_i$, µM |
|---|---|---|---|---|---|
| 4qq | H | 0.025 ± 0.0014 | 4y | 3-CF$_3$ | 0.01 ± 0.0006 |
| 4o | 3-NHBOC | 0.012 ± 0.0008 | 4z | 4-CF$_3$ | 0.075 ± 0.004 |
| 4p | 4-NHBOC | 0.023 ± 0.0013 | 4aa | 2-CO$_2$CH$_3$ | 0.034 ± 0.002 |
| 4q | 2-F | 0.008 ± 0.0006 | 4bb | 3-CO$_2$CH$_3$ | 0.030 ± 0.0018 |
| 4r | 3-F | 0.0032 ± 0.0002 | 4cc | 4-CO$_2$CH$_3$ | 0.025 ± 0.0014 |
| 4s | 4-F | 0.036 ± 0.002 | 4gg | 2-Cl | 0.013 ± 0.0007 |
| 4rr | 2-NO$_2$ | 0.017 ± 0.001 | 4hh | 3-Cl | 0.007 ± 0.0004 |
| 4ss | 3-NO$_2$ | 0.0048 ± 0.0003 | 4ii | 4-Cl | 0.020 ± 0.0011 |
| 4w | 4-NO$_2$ | 0.031 ± 0.0018 | 4jj | 2,3-Cl$_2$ | 0.005 ± 0.0003 |
| 4x | 2-CF$_3$ | 0.016 ± 0.001 | | | |
Figure 6

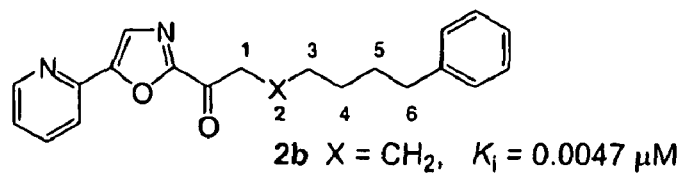
2b X = CH$_2$, $K_i$ = 0.0047 μM
| compd | X | $K_i$, μM | compd | X | $K_i$, μM |
|---|---|---|---|---|---|
| 12a | O | 0.06 ± 0.005 | 12c | SO | 1 ± 0.08 |
| 12b | S | 0.004 ± 0.0002 | 12d | SO$_2$ | 20 ± 1.2 |
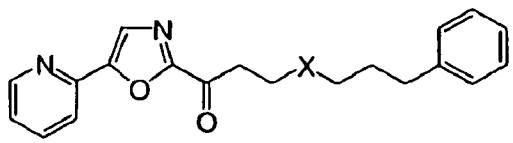
| compd | X | $K_i$, μM | compd | X | $K_i$, μM |
|---|---|---|---|---|---|
| 12e | O | 0.09 ± 0.005 | 12f | NCH$_3$ | 0.2 ± 0.015 |
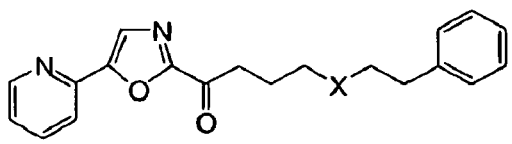
| compd | X | $K_i$, μM | compd | X | $K_i$, μM |
|---|---|---|---|---|---|
| 12g | O | 0.063 ± 0.006 | 12h | NCH$_3$ | 3.5 ± 0.2 |
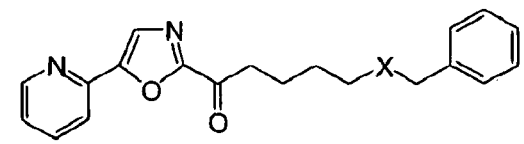
| compd | X | $K_i$, μM | compd | X | $K_i$, μM |
|---|---|---|---|---|---|
| 12i | O | 0.055 ± 0.005 | 12l | SO | 2.5 ± 0.13 |
| 12j | NCH$_3$ | 0.20 ± 0.012 | 12m | SO$_2$ | >10 |
| 12k | S | 0.025 ± 0.0018 | | | |
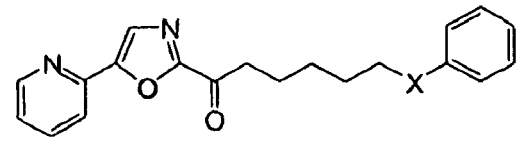
| compd | X | $K_i$, μM | compd | X | $K_i$, μM |
|---|---|---|---|---|---|
| 12n | O | 0.014 ± 0.0013 | 12q | SO | 1 ± 0.06 |
| 12o | NCH$_3$ | 0.04 ± 0.003 | 12r | SO$_2$ | 6 ± 0.4 |
| 12p | S | 0.003 ± 0.0002 | | | |
Figure 7

2b  R = C(O)(CH$_2$)$_6$Ph, $K_i$ = 0.0047 μM

| compd | R | $K_i$, μM |
|---|---|---|
| 13a | -C(O)CH$_2$CH$_2$C(O)NH-CH$_2$CH$_2$-Ph ⇌ hydroxy-pyrrolidinone (>95%), N-(CH$_2$)$_2$Ph | >100 |
| 13b | -C(O)(CH$_2$)$_3$C(O)NH-CH$_2$Ph | 20 ± 1.2 |
| 13c | -C(O)(CH$_2$)$_4$C(O)NH-Ph | 3.1 ± 0.1 |
| 13d | -C(O)CH(OH)(CH$_2$)$_4$CH$_2$Ph | 0.008 ± 0.0006 |
| 13e | -C(O)CH$_2$CH(OH)(CH$_2$)$_3$Ph | 0.035 ± 0.002 |
| 13f | -C(O)(CH$_2$)$_2$CH(OH)(CH$_2$)$_2$Ph ⇌ tetrahydrofuran (50%) | 0.5 ± 0.03 |
| 13g | -C(O)(CH$_2$)$_3$CH(OH)CH$_2$Ph ⇌ tetrahydropyran (50%) | 1.5 ± 0.08 |
| 13h | -C(O)(CH$_2$)$_4$CH(OH)CH$_2$Ph | 0.2 ± 0.015 |
| 13I | -C(O)(CH$_2$)$_5$CH(OH)Ph | 0.035 ± 0.0025 |

2b R = (CH$_2$)$_6$Ph, $K_i$ = 0.0047 μM

| compd | R | $K_i$, μM |
|---|---|---|
| 14a | ⟜⌒CO$_2$CH$_3$ | >100 |
| 14b | ⟜⌒⌒CO$_2$CH$_3$ | 7 ± 0.4 |
| 14c | ⟜⌒⌒⌒CO$_2$CH$_3$ | 1.8 ± 0.13 |
| 14d | ⟜-cyclopropyl | >50 |
| 14e | ⟜-cyclopentyl | 2.5 ± 0.15 |
| 14f | ⟜⌒Cl | 0.8 ± 0.05 |
| 14g | ⟜C(O)(CH$_2$)$_4$Ph | >2 |

| compd | | $K_i$, μM |
|---|---|---|
| 14h (pyridyl-oxazole-CH(OH)CH(OH)(CH$_2$)$_5$Ph) | | 2 ± 0.1 |
| 14i (pyridyl-oxazole-CH(OH)CH$_2$N(CH$_3$)(CH$_2$)$_4$Ph) | | >100 |

| compd | $K_i$, μM (human) | $K_i$, μM (rat) |
|---|---|---|
| 5jj | 0.0012 ± .001 | 0.0009 |

Figure 10

| compd | $K_i$, μM | FAAH | KIAA1363 | TGH |
|---|---|---|---|---|
| 2b | 0.0047 | 0.002 | >100 (>50000) | 0.6 (300) |
| 5a | 0.0043 | 0.02 | >100 (>5000) | 0.7 (35) |
| 5b | 0.0051 | 0.04 | >100 (>3300) | 0.8 (27) |
| 5c | 0.0026 | 0.01 | >100 (>10000) | 0.3 (30) |
| 5d | 0.011 | 0.04 | >100 (>2500) | 0.02 (0.5) |
| 5e | 0.12 | 0.03 | >100 (>3300) | 1 (33) |
| 5f | 0.032 | 0.02 | >100 (>5000) | 1 (50) |
| 5g | 0.003 | 0.03 | >100 (>3300) | 3 (100) |
| 5h | 0.0033 | 0.03 | >100 (>3300) | 5 (170) |
| 5i | 0.0028 | 0.04 | >100 (>2500) | 5 (125) |
| 5j | 0.0058 | 0.01 | >100 (>10000) | 5 (500) |
| 5k | 0.0025 | 0.02 | >100 (>5000) | 1 (50) |
| 5l | 0.0062 | 0.02 | >100 (>5000) | 5 (250) |
| 5n | 0.003 | 0.004 | >100 (>25000) | 3 (750) |
| 5q | 0.0017 | 0.03 | >100 (>3300) | 0.5 (17) |
| 5r | 0.0022 | 0.01 | >100 (>10000) | 1 (100) |
| 5s | 0.0032 | 0.02 | >100 (>5000) | 1 (50) |
| 5t | 0.0033 | 0.03 | >100 (>3300) | 10 (330) |
| 5u | 0.0042 | 0.01 | >100 (>10000) | 0.3 (30) |
| 5v | 0.0025 | 0.02 | >100 (>5000) | 0.8 (40) |
| 5w | 0.0065 | 0.0005 | >100 (>200000) | 50 (100000) |
| 5x | 0.004 | 0.03 | >100 (>3300) | 7 (230) |
| 5y | 0.001 | 0.02 | >100 (>5000) | 0.2 (10) |
| 5z | 0.004 | 0.009 | >100 (>10000) | 0.2 (20) |
| 5aa | 0.001 | 0.0004 | >100 (>250000) | 10 (25000) |
| 5bb | 0.0019 | 0.0004 | >100 (>250000) | 10 (25000) |
| 5cc | 0.0015 | 0.00024 | >100 (>400000) | 6 (25000) |
| 5gg | 0.0019 | 0.02 | >100 (>5000) | 0.6 (30) |
| 5hh | 0.0009 | 0.002 | >100 (>50000) | 0.5 (250) |
| 5ii | 0.0027 | 0.03 | >100 (>3300) | 2 (67) |
| 5jj | 0.0009 | 0.007 | >100 (>14000) | 0.5 (70) |
| 5kk | 0.037 | 0.1 | >100 (>1000) | 3 (30) |
| 5ll | 0.0013 | 0.004 | >100 (>25000) | 4 (1000) |
| 5mm | 0.019 | 0.05 | >100 (>2000) | 2 (40) |
| 5nn | 0.0067 | 0.03 | >100 (>3300) | 30 (1000) |
| 5oo | 0.015 | 0.08 | >100 (>1250) | 20 (250) |
| 12a | 0.06 | 0.01 | 0.58 (>58) | 0.34 (34) |

Figure 11

TRICYCLIC INHIBITORS OF FATTY ACID AMIDE HYDROLASE

PRIORITY CLAIM TO RELATED APPLICATIONS

This application is a national stage application under 35 U.S.C. §371 of PCT/US2008/006913, filed May 30, 2008, and published as WO 2008/150492 A1 on Dec. 11, 2008, which claims priority to U.S. Application No. 60/932,494, filed May 31, 2007, which applications and publication are incorporated herein by reference and made a part hereof in their entirety, and the benefit of priority is claimed thereto.

STATEMENT OF GOVERNMENT SUPPORT

A portion of the work described herein was supported by grant number DA 15648 from the National Institutes of Health. The United States Government has certain rights in this invention.

FIELD OF THE INVENTION

The present invention related to certain oxazole compounds, pharmaceutical compositions containing them, and methods of using them for the treatment of disease states, disorders, and conditions mediated by fatty acid amide hydrolase (FAAH) activity.

BACKGROUND OF THE INVENTION

The enzyme fatty acid amide hydrolase (FAAH) is the primary catabolic regulator of several bioactive lipid amides in vivo, including anandamide (1a) and oleamide (1b) (Bracey, M. H.; Hanson, M. A.; et al. *Science* 2002, 298, 1793-1796; Cravatt, B. F.; Giang, D. K.; et al. *Nature* 1996, 384, 83-87; Giang, D. K.; Cravatt, B. F. *Proc. Natl. Acad. Sci. U.S.A.* 1997, 94, 2238-2242; Patricelli, M. P.; Cravatt, B. F. *Vit. Hormones* 2001, 62, 95-131). The central nervous system distribution of FAAH suggests that it degrades neuromodulating fatty acid amides at their sites of action and is intimately involved in their regulation (Egertova, M.; Cravatt, B. F.; et al. *Neuroscience* 2003, 119, 481-496). Fatty acid amide hydrolase is currently the only characterized mammalian enzyme that is in the amidase signature family bearing an unusual catalytic Ser-Ser-Lys triad (Bracey, M. H.; Hanson, M. A.; et al. *Science* 2002, 298, 1793-1796; Patricelli, M. P.; Cravatt, B. F. *Vit. Hormones* 2001, 62, 95-131; Patricelli, M. P.; Cravatt, B. F. *Biochemistry* 1999, 38, 14125-14130; Patricelli, M. P.; Cravatt, B. F. *J. Biol. Chem.* 2000, 275, 19177-19184; Patricelli, M. P.; Lovato, M. A.; et al. *Biochemistry* 1999, 38, 9804-9812). Recently, the crystal structure of FAAH cocrystallized with an irreversibly-bound arachidonoyl fluorophosphonate confirmed its unusual catalytic triad and provided structural details of this enzyme (Bracey, M. H.; Hanson, M. A.; et al. *Science* 2002, 298, 1793-1796).

Both anandamide (1a) (Dervane, W. A.; Hanus, L.; et al. *Science* 1992, 258, 1946-1949) and oleamide (1b) (Boger, D. L.; Henriksen, S. J.; et al. *Curr. Pharm. Des.* 1998, 4, 303-314; Cravatt, B. F.; Lerner, R. A.; Boger, D. L. *J. Am. Chem. Soc.* 1996, 118, 580-590; Cravatt, B. F.; et al. *Science* 1995, 268, 1506-1509) have emerged as prototypical members of the class of bioactive lipid amides (Boger, D. L.; Fecik, R. A.; et al. *Bioorg. Med. Chem. Lett.* 2000, 10, 2613-2616; Lang, W.; Qin, C.; et al. *J. Med. Chem.* 1999, 42, 896-902) that serve as chemical messengers (FIG. 1). Anandamide (1a), the most recognizable member of the endogenous fatty acid ethanolamides (Schmid, H. H. O.; Schmid, P. C.; Natarajan, V. *Prog. Lipid Res.* 1990, 29, 1-43), binds and activates both the central type-1 (CB1) and peripheral type-2 (CB2) cannabinoid receptors. Anandamide (1a), and members of the cannabinoid family (Lambert, D. M.; Fowler, C. J. *J. Med. Chem.* 2005, 48, 5059-5087), have been implicated in the modulation of nociception (Calignano, A.; La Rana, G.; et al. *Nature* 1998, 394, 277-281; Cravatt, B. F.; Lichtman, A. H. *J. Neurobiol.* 2004, 61, 149-160; Walker, J. M.; Huang, S. M.; et al. *Proc. Natl. Acad. Sci. U.S.A.* 1999, 96, 12198-12203), feeding (Gomez, R.; Navarro, M.; et al. *J. Neurosci.* 2002, 22, 9612-9617; Williams, C. M.; Kirkham, T. C. *Physiol. Behav.* 2002, 76, 241-250), emesis, anxiety (Kathuria, S.; Gaetani, S.; et al. *Nat. Med.* 2003, 9, 76-81), cell proliferation (Melck, D.; Rueda, D.; et al. *FEBS Lett.* 1999, 463, 235-240; Yamaji, K.; Sarker, K. P.; et al. *Thromb. Haemostasis* 2003, 89, 875-884), inflammation (Massa, F.; Marsicano, G.; et al. *J. Clin. Invest.* 2004, 113, 1202-1209), memory (Mallet, P. E.; Beninger, R. J. *Psychopharmacology* 1998, 140, 11-19) and neuroprotection after brain injury (Panikashvili, D.; Simeonidou, C.; et al. *Nature* 2001, 413, 527-531). Thus, the cannabinoids have clinical relevance for analgesia, anxiety, epilepsy, cachexia, cancer, Alzheimer's disease as well as other neurodegenerative diseases (Axelrod, J.; Felder, C. C. *Neurochem. Res.* 1998, 23, 575-581; Di Marzo, V.; Bisogno, T.; et al. *Curr. Med. Chem.* 1999, 6, 721-744; Martin, B. R.; Mechoulam, R.; et al. *Life Sci.* 1999, 65, 573-595).

Oleamide (1b) was found to accumulate in the cerebrospinal fluid of animals under conditions of sleep deprivation and to induce physiological sleep in a dose dependent manner (Boger, D. L.; Henriksen, S. J.; et al. *Curr. Pharm. Des.* 1998, 4, 303-314; Cravatt, B. F.; et al. *Science* 1995, 268, 1506-1509). It modulates serotonergic systems (Cheer, J. F.; Cadogan, A.-K.; et al. *Neuropharmacology* 1999, 38, 533-541; Thomas, E. A.; Cravatt, B. F.; et al. *J. Neurochem.* 1999, 72, 2370-2378; Boger, D. L.; Patterson, J. E.; et al. *Proc. Natl. Acad. Sci. U.S.A.* 1998, 95, 4102-4107) and GABAergic transmission (Lees, G.; Dougalis, A. *Brain Res.* 2004, 997, 1-14; Yost, C. S.; Hampson, A. J.; et al. *Anesth. Analg.* 1998, 86, 1294-1299), decreases body temperature and locomotor activity (Huitrón-Reséndiz, S.; Gombart, L.; et al. *Exp. Neurol.* 2001, 172, 235-243), and blocks glial gap junction cell-cell communication (Boger, D. L.; Patterson, J. E.; et al. *Proc. Natl. Acad. Sci. U.S.A.* 1998, 95, 4810-4815; Guan, X.; Cravatt, B. F.; et al. *J. Cell Biol.* 1997, 139, 1785-1792). The dual inhibition of presynaptic $Na^+$ channels and postsynaptic $GABA_A$ receptors suggests oleamide (1b) may possess a mode of action common to drugs that are widely used for the treatment of anxiety, sleep disorders, and epilepsy and that it represents an endogenous ligand for such depressant drug sites in the mammalian brain. Oleamide (1b) decreases body temperature and locomotor activity (Huitrón-Reséndiz, S.; Gombart, L.; et al. *Exp. Neurol.* 2001, 172, 235-243), and exhibits the characteristic in vivo analgesic and cannabinoid behavioral effects of anandamide (Cheer, J. F.; Cadogan, A.-K.; et al. *Neuropharmacology* 1999, 38, 533-541; Mechoulam, R.; Fride, E.; et al. *Nature* 1997, 389, 25-26), albeit without apparent cannabinoid receptor activation. It has been suggested that the cannabinoid behavioral effects of oleamide (1b) may be mediated through an as yet unknown distinct pharmacological target (Lees, G.; Dougalis, A. *Brain Res.* 2004, 997, 1-14). Because oleamide (1b) may play an important role in sleep, it may provide opportunities for the development of sleep aids that induce physiological sleep lacking the side effects of the sedative-hypnotics (e.g., benzodiazepene class), which include rebound insomnia, anterograde amnesia and suicide abuse potential.

The pharmacological actions of anandamide (1a) and oleamide (1b) are terminated by FAAH (FIG. 1) (Bracey, M. H.; Hanson, M. A.; et al. *Science* 2002, 298, 1793-1796; Cravatt, B. F.; Giang, D. K.; et al. *Nature* 1996, 384, 83-87; Giang, D. K.; Cravatt, B. F. *Proc. Natl. Acad. Sci. U.S.A.* 1997, 94, 2238-2242; Patricelli, M. P.; Cravatt, B. F. *Vit. Hormones* 2001, 62, 95-131). Studies with FAAH knockout mice have not only shown that FAAH is a key regulator of fatty acid amide signaling in vivo, but that the animals exhibit a significantly augmented behavioral response (e.g., increased analgesia, hypomotility, catalepsy) to administered anandamide (1a) and oleamide (1b), that correlated with a CB1-dependent analgesic phenotype (Clement, A. B.; Hawkins, E. G.; et al. *J. Neurosci.* 2003, 23, 3916-3923; Cravatt, B. F.; Demarest, K.; et al. *Proc. Natl. Acad. Sci. U.S.A.* 2001, 98, 9371-9376; Cravatt, B. F.; Saghatelian, A.; et al. *Proc. Natl. Acad. Sci. U.S.A.* 2004, 101, 10821-10826; Lichtman, A. H.; Shelton, C. C.; et al. *Pain* 2004, 109, 319-327). As such, FAAH has emerged as an interesting new therapeutic target for a range of clinical disorders (Lambert, D. M.; Fowler, C. J. *J. Med. Chem.* 2005, 48, 5059-5087; Cravatt, B. F.; Lichtman, A. H. *Curr. Opin. Chem. Biol.* 2003, 7, 469-475).

Due to the potentially exciting therapeutic potential of inhibiting FAAH, there has been increasing interest in the development of potent inhibitors (FIG. 2) (Kathuria, S.; Gaetani, S.; et al. *Nat. Med.* 2003, 9, 76-81; Boger, D. L.; Miyauchi, H.; et al. *J. Med. Chem.* 2005, 48, 1849-1856; Boger, D. L.; Sato, H.; et al. *Bioorg. Med. Chem. Lett.* 1999, 9, 265-270; Boger, D. L.; Sato, H.; et al. *Proc. Natl. Acad. Sci. U.S.A.* 2000, 97, 5044-5049; De Petrocellis, L.; Melck, D.; et al. *Biochem. Biophys. Res. Commun.* 1997, 231, 82-88; Deutsch, D. G.; Omeir, R.; et al. *Biochem. Pharmacol.* 1997, 53, 255-260; Deutsch, D. G.; Lin, S.; et al. *Biochem. Biophys. Res. Commun.* 1997, 231, 217-221; Du, W.; Hardouin, C.; et al. *Bioorg. Med. Chem. Lett.* 2005, 15, 103-106; Edgemond, W. S.; Greenberg, M. J.; et al. *J. Pharmacol. Exp. Ther.* 1998, 286, 184-190; Fernando, S. R.; Pertwee, R. G. *Br. J. Pharmacol.* 1997, 121, 1716-1720; Koutek, B.; Prestwich, G. D.; et al. *J. Biol. Chem.* 1994, 269, 22937-22940; Patricelli, M. P.; Patterson, J. P.; et al. *Bioorg. Med. Chem. Lett.* 1998, 8, 613-618; Patterson, J. E.; Ollmann, I. R.; et al. *J. Am. Chem. Soc.* 1996, 1996, 5938-5945; Tarzia, G.; Duranti, A.; et al. *ChemMedChem* 2006, 1, 130-139; Tarzia, G.; Duranti, A.; et al. *J. Med. Chem.* 2003, 46, 2352-2360; Mor, M.; Rivara, S.; et al. *J. Med. Chem.* 2004, 47, 4998-5008; Muccioli, G. G.; Fazio, N.; et al. *J. Med. Chem.* 2006, 49, 417-425). These include the discovery that the endogenous sleep-inducing molecule 2-octyl γ-bromoacetoacetate is an effective FAAH inhibitor (Patricelli, M. P.; Patterson, J. P.; et al. *Bioorg. Med. Chem. Lett.* 1998, 8, 613-618), a series of reversible inhibitors bearing an electrophilic ketone (Boger, D. L.; Sato, H.; et al. *Bioorg. Med. Chem. Lett.* 1999, 9, 265-270; Koutek, B.; Prestwich, G. D.; et al. *J. Biol. Chem.* 1994, 269, 22937-22940; Patterson, J. E.; Ollmann, I. R.; et al. *J. Am. Chem. Soc.* 1996, 1996, 5938-5945) (e.g., trifluoromethyl ketone-based) that have not proven selective for FAAH over other mammalian serine hydrolases (Leung, D.; Du, W.; et al. *Bioorg. Med. Chem. Lett.* 2005, 15, 1423-1428) and a set of irreversible inhibitors (De Petrocellis, L.; Melck, D.; et al. *Biochem. Biophys. Res. Commun.* 1997, 231, 82-88; Deutsch, D. G.; Omeir, R.; et al. *Biochem. Pharmacol.* 1997, 53, 255-260; Deutsch, D. G.; Lin, S.; et al. *Biochem. Biophys. Res. Commun.* 1997, 231, 217-221; Edgemond, W. S.; Greenberg, M. J.; et al. *J. Pharmacol. Exp. Ther.* 1998, 286, 184-190; Fernando, S. R.; Pertwee, R. G. *Br. J. Pharmacol.* 1997, 121, 1716-1720) (e.g., fluorophosphonates and sulphonyl fluorides). Recently, two classes of inhibitors have been disclosed that provide significant opportunities for the development of an inhibitor with therapeutic potential. One class is the aryl carbamates (e.g., URB-597 2a; FIG. 2) that acylate an active site catalytic serine and which were shown to exhibit anxiolytic activity and induce analgesia (Kathuria, S.; Gaetani, S.; et al. *Nat. Med.* 2003, 9, 76-81; Tarzia, G.; Duranti, A.; et al. *ChemMedChem* 2006, 1, 130-139; Tarzia, G.; Duranti, A.; et al. *J. Med. Chem.* 2003, 46, 2352-2360; Mor, M.; Rivara, S.; et al. *J. Med. Chem.* 2004, 47, 4998-5008; Hohmann, A. G.; Suplita, R. L.; et al. *Nature* 2005, 435, 1108-1112). However, the selectivity of such aryl carbamate inhibitors is low and recent studies illustrate that either no or minimal selectivity is achieved (e.g., other targets of URB-597 2a are carboxylesterase 6 and triacylglyceride hydrolase) (Alexander, J. P.; Cravatt, B. F. *Chem. Biol.* 2005, 12, 1179-1187; Lichtman, A. H.; Leung, D.; et al. *J. Pharmacol. Exp. Ther.* 2004, 311, 441-448; Alexander, J. P.; Cravatt, B. F. *J. Am. Chem. Soc.* 2006, 128, 9699-9704). A second class is the α-ketoheterocycle-based inhibitors of which some are extraordinarily potent (e.g., OL-135 2b; FIG. 2) (Boger, D. L.; Miyauchi, H.; et al. *J. Med. Chem.* 2005, 48, 1849-1856; Boger, D. L.; Sato, H.; et al. *Proc. Natl. Acad. Sci. U.S.A.* 2000, 97, 5044-5049; Du, W.; Hardouin, C.; et al. *Bioorg. Med. Chem. Lett.* 2005, 15, 103-106; Leung, D.; Du, W.; et al. *Bioorg. Med. Chem. Lett.* 2005, 15, 1423-1428; Boger, D. L.; Miyauchi, H.; et al. *Bioorg. Med. Chem. Lett.* 2001, 11, 1517-1520). These competitive inhibitors bind to FAAH via reversible hemiketal formation with an active site serine, and are not only potent and extraordinarily selective for FAAH versus other mammalian serine hydrolases (Boger, D. L.; Miyauchi, H.; et al. *J. Med. Chem.* 2005, 48, 1849-1856; Leung, D.; Du, W.; et al. *Bioorg. Med. Chem. Lett.* 2005, 15, 1423-1428), but many are efficacious in vivo and promote analgesia (Lichtman, A. H.; Leung, D.; et al. *J. Pharmacol. Exp. Ther.* 2004, 311, 441-448; Chang, L.; Luo, L.; et al. *Br. J. Pharmacol.* 2006, 148, 102-113).

The present invention concerns the synthesis and evaluation of a systematic series of α-keto oxazole inhibitors having variations at the C2 acyl side chain along with results of the proteome-wide selectivity screening of the candidate inhibitors. The screening protocol is described by Leung, D.; Hardouin, C.; et al. *Nature Biotech.* 2003, 21, 687-691.

SUMMARY OF THE INVENTION

The novel 2-keto-oxazole derivatives of the invention have FAAH-modulating activity. A series of derivatives was prepared and evaluated for FAAH inhibitory potency as well as FAAH selectivity versus competitive serine proteases (e.g., TGH, KIAA1363). Aryl substitutions along the acyl side chain resulted in effective inhibitors. A large series of phenyl substituents proved to be effective inhibitors with hydrophobic or electron-withdrawing meta substituents generally enhancing binding affinity to the greatest extent, for example, compound 5hh (aryl=3-Cl—Ph, $K_i$=900 pM) displayed extremely potent activity. A systematic series of heteroatoms (O, NMe, S) and electron-withdrawing groups (SO, $SO_2$) positioned within the acyl side chain was investigated. The most tolerant position (position 6) along the acyl side chain provided effective inhibitors (see compound 12p, X=S, $K_i$=3 nM). A series of amides within the linking chain and hydroxyl substitutions on the chain were also explored. The activity of the compounds having amide placement at various positions along the side chain varied in potency. Hydroxyl substitution at positions 2 and 6 provided highly effective inhibitors (13a, 2-position OH, $K_i$=8 nM). Just as importantly, proteome-wide selectivity screening of the candidate inhibitors showed extraordinary selectivity for FAAH over all other serine hydrolases and proteases.

More particularly, in one general aspect, the invention relates to compounds of the following Formula (I), represented by following structure:

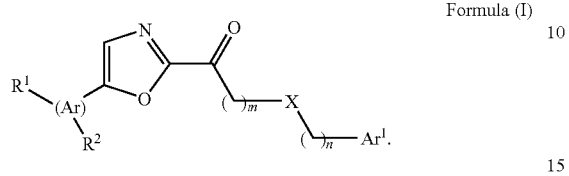

Formula (I)

In Formula I, Ar is a 5- or 6-membered aryl or heteroaryl ring having a carbon as its point of attachment to the oxazole; $R^1$ is independently selected from the group consisting of —($C_1$-$C_6$ alkyl), —($C_3$-$C_6$ alkyl), —$CF_3$, —CN, —C(O)$C_1$-$C_4$ alkyl optionally substituted with one, two, or three fluoro substituents, —$CO_2$($C_1$-$C_4$ alkyl), —$CO_2$H, —C(O)N($R^a$)$R^b$, —OH, —O($C_1$-$C_6$ alkyl), halo, —$NO_2$, —$NR^aR^b$, —N($R^a$)C(O)$R^b$, —N($R^a$)$SO_2R^b$, —$SO_2$N($R^a$)$R^b$, —$SR^a$, —S(O)$R^a$, —$SO_2R^a$; where $R^a$ and $R^b$ are each independently selected from the group consisting of —H, —($C_1$-$C_6$ alkyl), and —($C_3$-$C_6$ cycloalkyl); and $R^2$ is independently selected from the group consisting of —($C_1$-$C_6$ alkyl), —($C_3$-$C_6$ alkyl), —$CF_3$, —CN, —C(O)$C_1$-$C_4$ alkyl optionally substituted with one, two, or three fluoro substituents, —$CO_2$($C_1$-$C_4$ alkyl), —$CO_2$H, —C(O)N($R^c$)$R^d$, —OH, —O($C_1$-$C_6$ alkyl), -halo, —$NO_2$, —$NR^cR^d$, —N($R^c$)C(O)$R^d$, —N($R^c$)$SO_2R^d$, —$SO_2$N($R^c$)$R^d$, —$SR^c$, —S(O)$R^c$, —$SO_2R^c$; where $R^c$ and $R^d$ are each independently selected from the group consisting of —H, —($C_1$-$C_6$ alkyl), or —($C_3$-$C_6$ cycloalkyl); and $Ar^1$ selected from the group consisting of the following radicals:

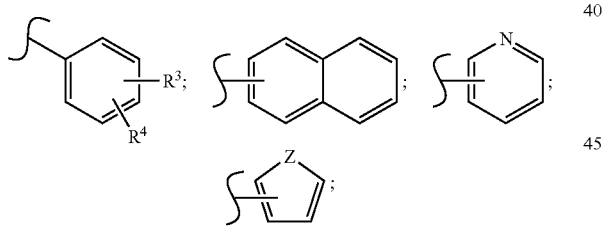

X is selected from the group of diradicals consisting of —$CH_2$—, —O—, —S—, —S(O)—, —S(O)$_2$—, —$NR^5$—, —C≡C—, —CH(OH)—, —C(O)NH—; and $R^3$ and $R^4$ are independently selected from the group consisting —H, —NHBOC, —F, —Cl, —Br, —I, —$NH_2$, —$NO_2$, —O($C_1$-$C_6$ alkyl), —S($C_1$-$C_6$ alkyl), —S(O)($C_1$-$C_6$ alkyl), —S(O)$_2$($C_1$-$C_6$ alkyl), —$CF_3$, —COOH, —$CO_2$($C_1$-$C_6$ alkyl), —($C_1$-$C_6$ alkyl); $R^5$ is selected from the group consisting of —H, and —($C_1$-$C_6$ alkyl); and Z is selected from the group of diradicals consisting of —O—, —S—, and —$NR^5$—; and m is an integer between 0 and 6; and n is an integer between 0 and 6. However, the following provisos apply: if m is 0, then n cannot be 0; and if X is —$CH_2$—, then $Ar^1$ cannot be phenyl. In a preferred embodiment, Ar is selected from the group consisting of phenyl, pyridyl, pyridazinyl, pyrimidinyl, pyrimidinedione, pyrazinyl, thiophenyl, furanyl, imidazolyl, oxazolyl, triazolyl and tetrazolyl. In other preferred embodiments, Ar is selected from the following group:

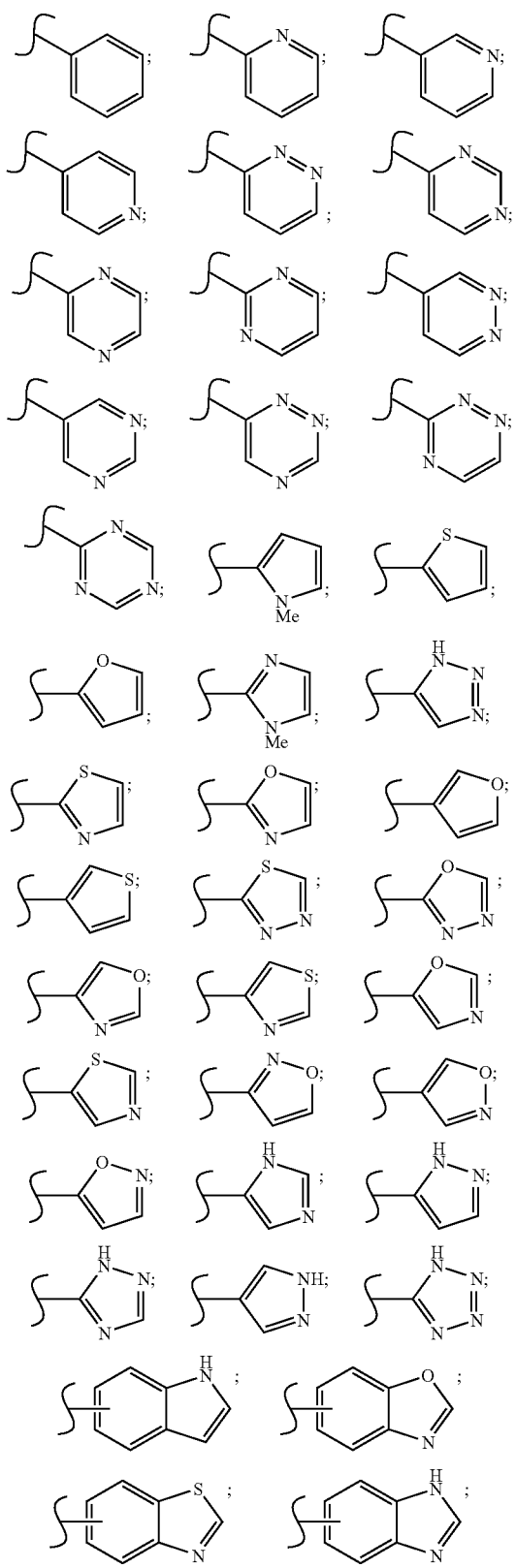

-continued

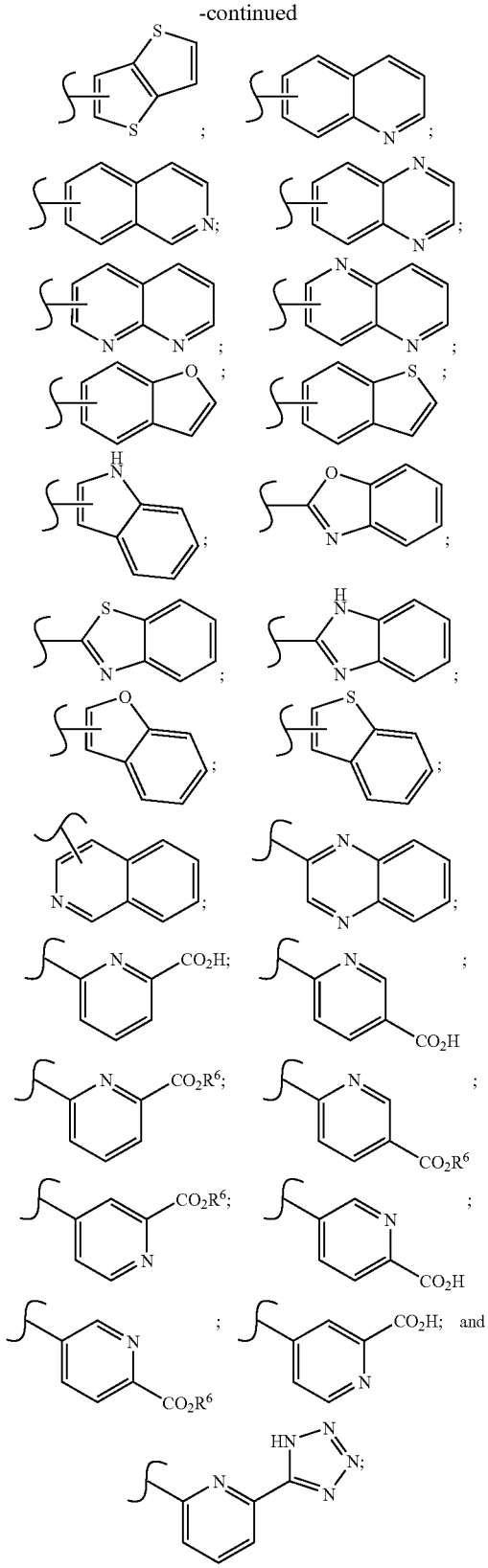

where $R^6$=($C_1$-$C_6$ alkyl).

In yet other embodiments, $R^1$ is selected from the group consisting of —CH$_3$, —CF$_3$, —CN, —C(O)CF$_3$, —CO$_2$CH$_3$, —CO$_2$H, —C(O)NH$_2$, —OH, —OCH$_3$, —F, —NO$_2$, —NH$_2$, and —SO$_2$NH$_2$. Preferably, $R^2$ is —H.

Another aspect of the invention is directed to a process for inhibiting the catalytic activity of fatty acid amide hydrolase. The process comprises the step of contacting the fatty acid amide hydrolase with a solution having an inhibitory concentration of a compound of Formula I.

In preferred embodiments, the compound of Formula (I) is a compound specifically described or exemplified in the detailed description below.

In a further general aspect, the invention relates to pharmaceutical compositions each comprising: (a) an effective amount of an agent selected from compounds of Formula (I) and pharmaceutically acceptable salts, pharmaceutically acceptable prodrugs, and pharmaceutically active metabolites thereof; and (b) a pharmaceutically acceptable excipient.

In another general aspect, the invention relates to pharmaceutical combinations of a compound of Formula I and another bioactive agent such as another FAAH inhibitor, as well as NSAIDS, Cox inhibitors and the like as described in detail in the following section.

In another general aspect, the invention relates to prodrugs and active metabolites of a compound of Formula I.

In another general aspect, the invention is directed to a method of treating a subject suffering from or diagnosed with a disease, disorder, or medical condition mediated by FAAH activity, comprising administering to the subject in need of such treatment an effective amount of a compound of Formula (I), or a pharmaceutically acceptable salt, pharmaceutically acceptable prodrug, or pharmaceutically active metabolite of such compound.

In certain preferred embodiments of the inventive method, the disease, disorder, or medical condition is selected from: anxiety, pain, sleep disorders, eating disorders, inflammation, multiple sclerosis and other movement disorders, HIV wasting syndrome, closed head injury, stroke, Alzheimer's disease, epilepsy, Tourette's syndrome, Niemann-Pick disease, Parkinson's disease, Huntington's chorea, optic neuritis, autoimmune uveitis, symptoms of drug withdrawal, nausea, emesis, sexual dysfunction, post-traumatic stress disorder, cerebral vasospasm, glaucoma, irritable bowel syndrome, inflammatory bowel disease, immunosuppression, gastroesophageal reflux disease, paralytic ileus, secretory diarrhea, gastric ulcer, rheumatoid arthritis, unwanted pregnancy, hypertension, cancer, hepatitis, allergic airway disease, autoimmune diabetes, intractable pruritis, and neuroinflammation.

Additional embodiments, features, and advantages of the invention will be apparent from the appended claims, which are incorporated into this summary by reference, as well as from the following detailed description.

BRIEF DESCRIPTION OF DRAWINGS

FIG. 1 illustrates both anandamide (1a) and oleamide (1b) undergoing hydrolysis by fatty acid amide hydrolase (FAAH) to their respective carboxylic acids. Both have emerged as prototypical members of the class of bioactive lipid amides that serve as chemical messengers. The pharmacological actions of anandamide (1a) and oleamide (1b) are terminated by FAAH. The enzyme fatty acid amide hydrolase converts Oleamide (1b) to Oleic acid (1d), and Anandamide (1a) to Arachidonic acid (1c).

FIG. 5 illustrates a collection of tables showing a systematic series of aryl replacements and phenyl substitutions for the terminal phenyl group of OL-135 (2b).

FIG. 6 illustrates two tables where the linker chain contains an alkynyl group connecting the methylene portion to the aryl ring.

FIG. 7 illustrates a series of tables showing the effects of substitution along the side chain.

FIG. 10 illustrates a short table listing the differing $K_i$'s between human FAAH and rat FAAH for some of the more potent compounds.

FIG. 11 illustrates is a table showing the $K_i$ with FAAH and the other columns are $IC_{50}$'s with FAAH, KIAA1363 and TGH.

DETAILED DESCRIPTION OF INVENTION AND ITS EMBODIMENTS

Figure 2:
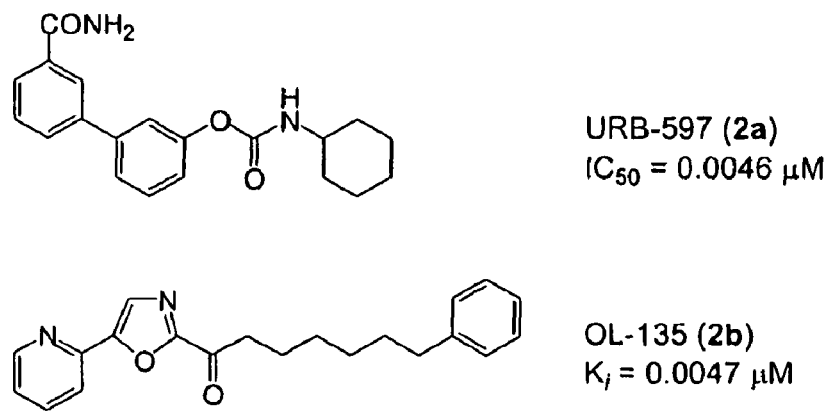
FIG. 2 shows the structures of URB-597 and OL-135 along with their respective activities. URB-597 is from one class comprising the aryl carbamates that acylate an active site catalytic serine and which were shown to exhibit anxiolytic activity and induce analgesia. OL-135 is an example of a ketoheterocycle-based inhibitor.

The present invention concerns substituted oxazole compounds having an alpha keto side chain at the 2 position of oxazole and an aryl or heteroaryl substituent at the 5 position of the oxazole. A series of aryl variations along the alpha keto side chain provided effective inhibitors (e.g., 5c, aryl=1-napthyl, $K_i$=2.6 nM) and an extensive series of phenyl substituents were incorporated to provide effective inhibitors with hydrophobic or electron-withdrawing meta substituents most significantly enhancing binding affinity. For example compound 5hh (aryl=3-Cl-Ph, $K_i$=900 pM) described below had extreme potency. Also, a series of heteroatom substitutions along the alpha keto side chain (O, NMe, S) and electron-withdrawing groups (SO, $SO_2$) were explored. It was discovered that these substitutions affected potency such that substitution β to the electrophilic carbonyl lowers potency. The most tolerant position (position 6 along the chain) provided effective inhibitors (12p, X=S, $K_i$=3 nM). A series of amides within the linking chain and hydroxyl substitutions on the chain were also explored. Amide placement within the side chain led to variation in inhibitory potency whereas hydroxyl substitution at positions 2 and 6 provided effective inhibitors (13d, 2-position OH, $K_i$=8 nM). Proteomic-wide screening of selected candidate inhibitors revealed that these new inhibitors are exquisitely selective for FAAH over all other mammalian serine proteases.

The invention may be more fully appreciated by reference to the following description, including the following glossary of terms and the concluding examples. For the sake of brevity, the disclosures of the publications cited in this specification are herein incorporated by reference.

As used herein, the terms "including", "containing" and "comprising" are used herein in their open, non-limiting sense.

Unless otherwise indicated by the text of this application, the use of the single articles of speech, "a", "an" and "the" include both the singular form and the plural form of the nouns with which they are associated. For example the term "a compound of Formula I" includes each single compound of Formula I, multiple compounds of Formula I and the group of compounds delineated by Formula I such that this term encompasses the phrases "compounds delineated by Formula I and "an individual compound delineated by Formula I."

The term "alkyl" refers to a straight- or branched-chain alkyl group having from 1 to 12 carbon atoms in the chain. Exemplary alkyl groups include methyl (Me, which also may be structurally depicted by /), ethyl (Et), n-propyl, isopropyl, butyl, isobutyl, sec-butyl, tert-butyl (tBu), pentyl, isopentyl, tert-pentyl, hexyl, isohexyl, and the like.

The term "aryl" refers to a monocyclic, fused bicyclic, or fused polycyclic, aromatic carbocycle (ring structure having ring atoms that are all carbon) having from 3 to 12 ring atoms per carbocycle. (Carbon atoms in aryl groups are $sp^2$ hybridized.) Illustrative examples of aryl groups include phenyl, naphthyl, anthracenyl, phenanthrenyl, and the like.

The term "heteroaryl" refers to a monocyclic, fused bicyclic, or fused polycyclic aromatic heterocycle (ring structure having ring atoms selected from carbon atoms as well as nitrogen, oxygen, and sulfur heteroatoms) having from 3 to 12 ring atoms per heterocycle. Illustrative examples of heteroaryl groups include the following moieties:

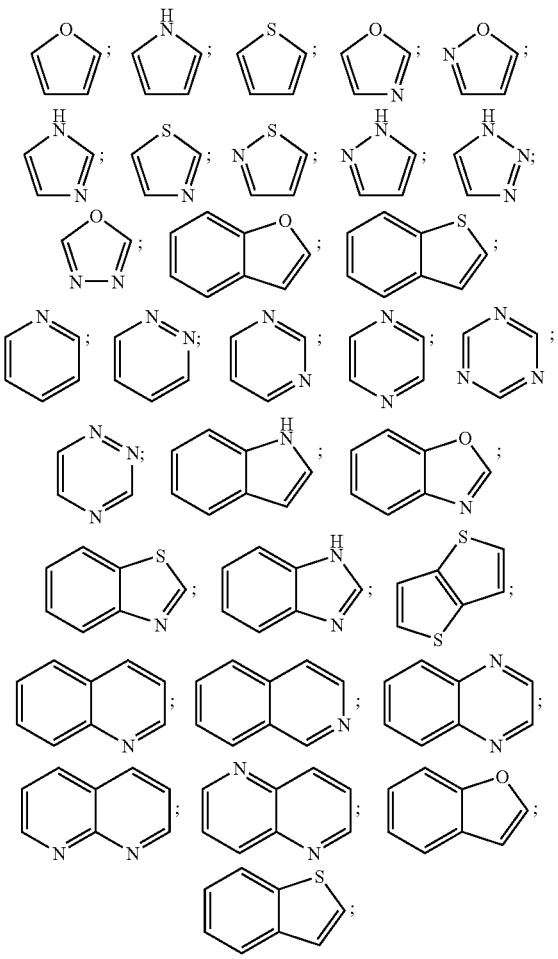

and the like.

The term "cycloalkyl" refers to a saturated or partially saturated, monocyclic, fused polycyclic, or spiro polycyclic, carbocycle having from 3 to 12 ring atoms per carbocycle. Illustrative examples of cycloalkyl groups include the following moieties:

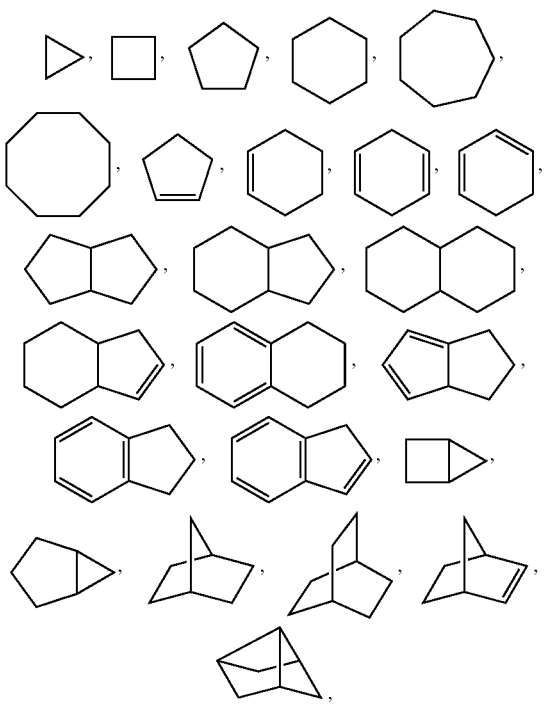

and the like.

The term "halogen" represents chlorine, fluorine, bromine or iodine. The term "halo" represents chloro, fluoro, bromo or iodo.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof.

Furthermore, certain structures may exist as geometric isomers (i.e., cis and trans isomers), as tautomers, or as atropisomers. Additionally, any formula given herein is intended to represent hydrates, solvates, and polymorphs of such compounds, and mixtures thereof.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, sulfur, phosphorous, fluorine, and chlorine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, $^{125}$I, respectively. Various isotopically labeled compounds of the present invention, for example those into which radioactive isotopes such as $^3$H, $^{11}$C, and $^{14}$C are incorporated. Such isotopically labeled compounds are useful in metabolic studies (preferably with $^{14}$C), reaction kinetic studies (with, for example $^2$H or $^3$H), detection or imaging techniques [such as positron emission tomography (PET) or single-photon emission computed tomography (SPECT)] including drug or substrate tissue distribution assays, or in radioactive treatment of patients. In particular, an $^{18}$F or $^{11}$C labeled compound may be particularly preferred for PET or SPECT studies. Further, substitution with heavier isotopes such as deuterium (i.e., $^2$H) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the moiety for the variable appearing elsewhere. In other words, where a variable appears more than once, the choice of the species from a specified list is independent of the choice of the species for the same variable elsewhere in the formula.

In preferred embodiments of the invention, Ar is selected from the group consisting of phenyl, pyridyl, pyridazinyl, pyrimidinyl, pyrimidine-dione, pyrazinyl, thiophenyl, furanyl, imidazolyl, oxazolyl, and tetrazolyl.

The invention includes also pharmaceutically acceptable salts of the compounds represented by Formula (I), such as of those described above. Pharmaceutically acceptable salts of the specific compounds exemplified are especially preferred.

A "pharmaceutically acceptable salt" is intended to mean a salt of a free acid or base of a compound represented by Formula (I) that is not toxic, biologically intolerable, or otherwise biologically undesirable. See, generally, S. M. Berge, et al., "Pharmaceutical Salts", J. Pharm. Sci., 1977, 66:1-19, and *Handbook of Pharmaceutical Salts, Propertions, Selection, and Use*; Stahl, P. H., Wermuth, C. G., Eds.; Wiley-VCH and VHCA: Zurich, 2002. Preferred pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt. Exemplary pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates.

If the compound of Formula (I) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, or ethanesulfonic acid, or the like.

If the compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, or alkaline earth metal hydroxide, or the like. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, and piperazine, and inorganic salts derived from sodium, calcium, potassium, magnesium, manganese, iron, copper, zinc, aluminum, and lithium.

The invention also relates to treatment methods employing pharmaceutically acceptable prodrugs of the compounds of Formula (I). The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I)). A "pharmaceutically acceptable prodrug" is a prodrug that is not toxic, biologically intolerable, or otherwise biologically unsuitable for administration to the subject. Conventional procedures for the selection and preparation of suitable prodrug derivatives are described, for example, in "Design of Prodrugs", ed. H. Bundgaard, Elsevier, 1985.

Exemplary prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formula (I). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) as amides or alkyl esters. Exemplary amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Preferred amides are derived from ammonia, $C_{1-3}$alkyl primary amines, and di($C_{1-2}$alkyl) amines. Exemplary esters of the invention include $C_{1-7}$alkyl, $C_{5-7}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in *Adv. Drug Delivery Rev.* 1996, 19, 115. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in *J. Med. Chem.* 1996, 39, 10. Free amines can also be derivatized as amides, sulfonamides or phosphonamides. All of these prodrug moieties may incorporate groups including ether, amine, and carboxylic acid functionalities.

Pharmaceutically active metabolites may also be used in the methods of the invention. A "pharmaceutically active metabolite" means a pharmacologically active product of metabolism in the body of a compound of Formula (I) or salt thereof. Prodrugs and active metabolites of a compound may be determined using routine techniques known or available in the art. See, e.g., Bertolini et al., *J. Med. Chem.* 1997, 40, 2011-2016; Shan et al., *J. Pharm. Sci.* 1997, 86 (7), 765-767; Bagshawe, *Drug Dev. Res.* 1995, 34, 220-230; Bodor, *Adv. Drug Res.* 1984, 13, 224-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

The compounds of Formula (I) and their pharmaceutically acceptable salts, pharmaceutically acceptable prodrugs, and pharmaceutically active metabolites (collectively, "agents") of the present invention are useful as FAAH inhibitors in the methods of the invention. The agents may be used in the inventive methods for the treatment or prevention of medical conditions, diseases, or disorders mediated through inhibition or modulation of FAAH, such as those described herein. Agents according to the invention may therefore be used as an analgesic, neuroprotectant, sedative, appetite stimulant, or contraceptive.

Exemplary medical conditions, diseases, and disorders include anxiety, pain, sleep disorders, eating disorders, inflammation, multiple sclerosis and other movement disorders, HIV wasting syndrome, closed head injury, stroke, Alzheimer's disease, epilepsy, Tourette's syndrome, epilepsy, Niemann-Pick disease, Parkinson's disease, Huntington's chorea, optic neuritis, autoimmune uveitis, symptoms of drug withdrawal, nausea, emesis, sexual dysfunction, post-traumatic stress disorder, or cerebral vasospasm.

Thus, the pharmaceutical agents may be used to treat subjects diagnosed with or suffering from a disease, disorder, or condition mediated through FAAH activity. The term "treat" or "treating" as used herein is intended to refer to administration of an agent or composition of the invention to a subject for the purpose of effecting a therapeutic or prophylactic benefit through modulation of FAAH activity. Treating includes reversing, ameliorating, alleviating, inhibiting the progress of, lessening the severity of, or preventing a disease, disorder, or condition, or one or more symptoms of such disease, disorder or condition mediated through modulation of FAAH activity. The term "subject" refers to a mammalian patient in need of such treatment, such as a human. "Modulators" include both inhibitors and activators, where "inhibitors" refer to compounds that decrease, prevent, inactivate, desensitize or down-regulate FAAH expression or activity, and "activators" are compounds that increase, activate, facilitate, sensitize, or up-regulate FAAH expression or activity.

Accordingly, the invention relates to methods of using the pharmaceutical agents described herein to treat subjects diagnosed with or suffering from a disease, disorder, or condition mediated through FAAH activity, such as: anxiety, pain, sleep disorders, eating disorders, inflammation, or movement disorders (e.g., multiple sclerosis).

Symptoms or disease states are intended to be included within the scope of "medical conditions, disorders, or diseases." For example, pain may be associated with various diseases, disorders, or conditions, and may include various etiologies. Illustrative types of pain treatable with a FAAH-modulating agent according to the invention include cancer pain, postoperative pain, GI tract pain, spinal cord injury pain, visceral hyperalgesia, thalamic pain, headache (including stress headache and migraine), low back pain, neck pain, musculoskeletal pain, peripheral neuropathic pain, central neuropathic pain, neurogenerative disorder related pain, and menstrual pain. HIV wasting syndrome includes associated symptoms such as appetite loss and nausea. Parkinson's disease includes, for example, levodopa-induced dyskinesia. Treatment of multiple sclerosis may include treatment of symptoms such as spasticity, neurogenic pain, central pain, or bladder dysfunction. Symptoms of drug withdrawal may be caused by, for example, addiction to opiates or nicotine. Nausea or emesis may be due to chemotherapy, postoperative, or opioid related causes. Treatment of sexual dysfunction may include improving libido or delaying ejaculation. Treatment of cancer may include treatment of glioma. Sleep disorders include, for example, sleep apnea, insomnia, and disorders calling for treatment with an agent having a sedative or narcotic-type effect. Eating disorders include, for example, anorexia or appetite loss associated with a disease such as cancer or HIV infection/AIDS.

In a treatment method according to the invention, an effective amount of a pharmaceutical agent according to the invention is administered to a subject suffering from or diagnosed as having such a disease, disorder, or condition. An "effective amount" means an amount or dose sufficient to generally bring about the desired therapeutic or prophylactic benefit in patients in need of such treatment.

Effective amounts or doses of the agents of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. An exemplary dose is in the range of from about 0.001 to about 200 mg of agent per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the agents of the invention may be used in combination with additional active compounds in the treatment of the above conditions. The additional compounds may be coadministered separately with an agent of Formula (I) or included with such an agent as an additional active ingredient in a pharmaceutical composition according to the invention. In an exemplary embodiment, additional active compounds are those that are known or discovered to be effective in the treatment of conditions, disorders, or diseases mediated by FAAH activity, such as another FAAH modulator or a compound active against another target associated with the particular condition, disorder, or disease. The combination may serve to increase efficacy (e.g., by including in the combination a compound potentiating the potency or effectiveness of an agent according to the invention), decrease one or more side effects, or decrease the required dose of the agent according to the invention. In one illustrative embodiment, a composition according to the invention may contain one or more additional active ingredients selected from opioids, NSAIDs (e.g., ibuprofen, cyclooxygenase-2 (COX-2) inhibitors, and naproxen), gabapentin, pregabalin, tramadol, acetaminophen, and aspirin.

The agents of the invention are used, alone or in combination with one or more other active ingredients, to formulate pharmaceutical compositions of the invention. A pharmaceutical composition of the invention comprises: (a) an effective amount of a pharmaceutical agent in accordance with the invention; and (b) a pharmaceutically acceptable excipient.

A "pharmaceutically acceptable excipient" refers to a substance that is not toxic, biologically intolerable, or otherwise biologically unsuitable for administration to a subject, such as an inert substance, added to a pharmacological composition or otherwise used as a vehicle, carrier, or diluent to facilitate administration of a pharmaceutical agent and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the pharmaceutical agents may be prepared using suitable pharmaceutical excipients and compounding techniques now or later known or available to those skilled in the art. The compositions may be administered in the inventive methods by oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the agents may be formulated to yield a dosage of, e.g., from about 0.05 to about 50 mg/kg daily, or from about 0.05 to about 20 mg/kg daily, or from about 0.1 to about 10 mg/kg daily.

Oral tablets may include the active ingredient mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The agents of this invention may also be administered by non-oral routes. For example, the compositions may be formulated for rectal administration as a suppository. For parenteral use, including intravenous, intramuscular, intraperitoneal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 µg/kg/minute of agent, admixed with a pharmaceutical carrier over a period ranging from several minutes to several days.

For topical administration, the agents may be mixed with a pharmaceutical carrier at a concentration of about 0.1% to about 10% of drug to vehicle. Another mode of administering the agents of the invention may utilize a patch formulation to affect transdermal delivery.

Agents may alternatively be administered in methods of this invention by inhalation, via the nasal or oral routes, e.g., in a spray formulation also containing a suitable carrier.

Chemistry

Figure 3:
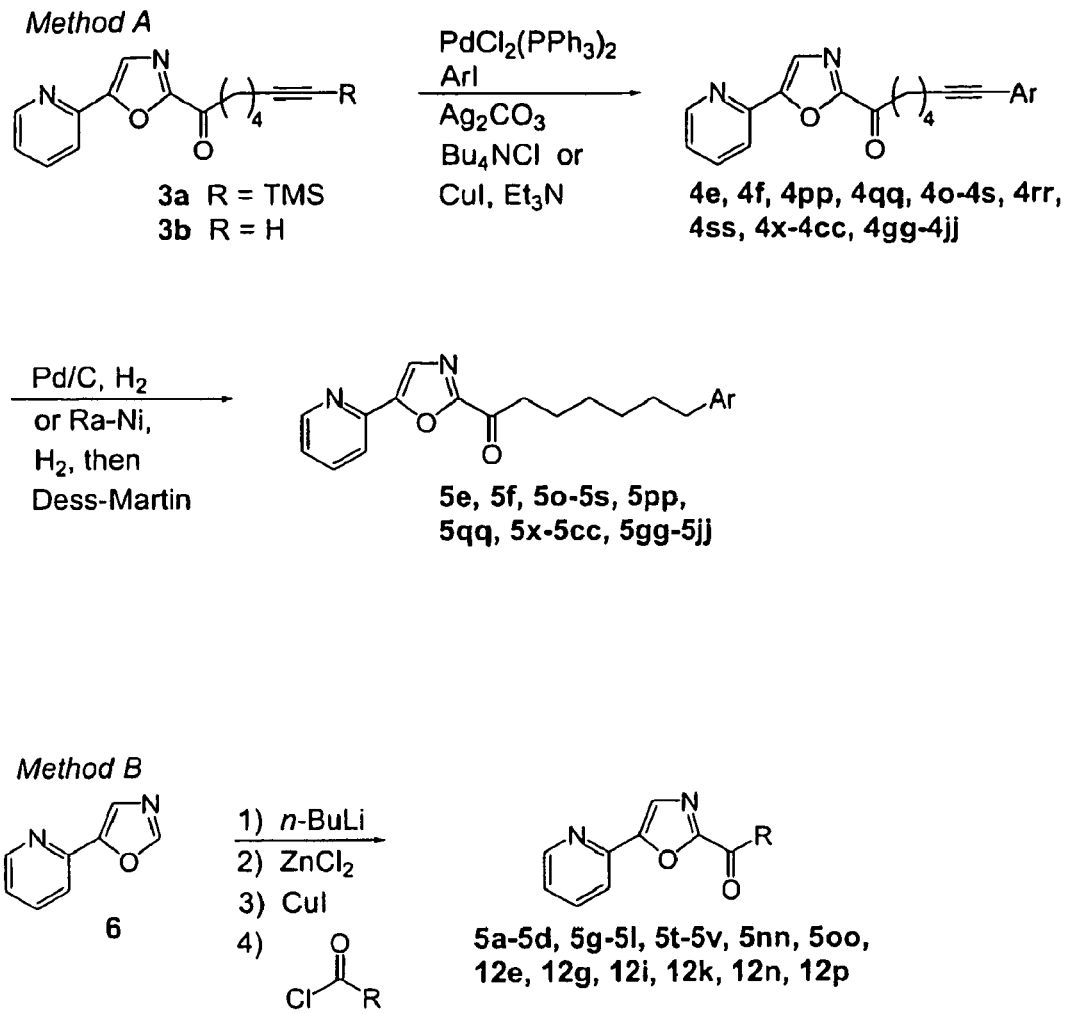
FIG. 3 illustrates how the majority of the candidate inhibitors were prepared.
Figure 4:
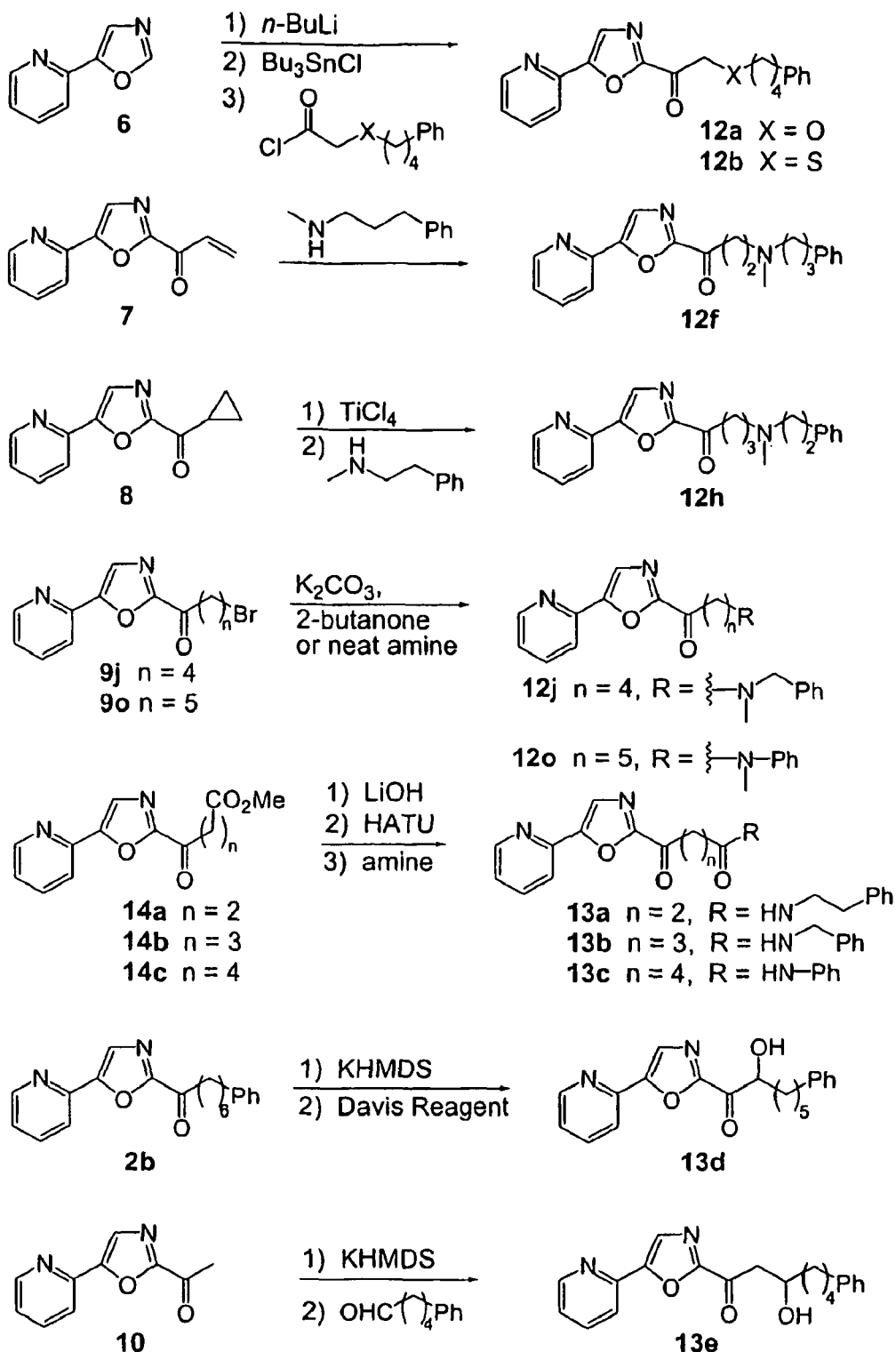
FIG. 4 illustrates the methods used in the synthesis of the inhibitors that were not prepared by either Method A or B.

Exemplary agents useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be desirable to employ, in the place of the ultimately desired substituent, a suitable group that may be carried through the reaction scheme and replaced as appropriate with the desired substituent. Unless otherwise specified, the variables are as defined above in reference to Formula (I). FIGS. 3 and 4 also illustrate these schemes.

SCHEME A

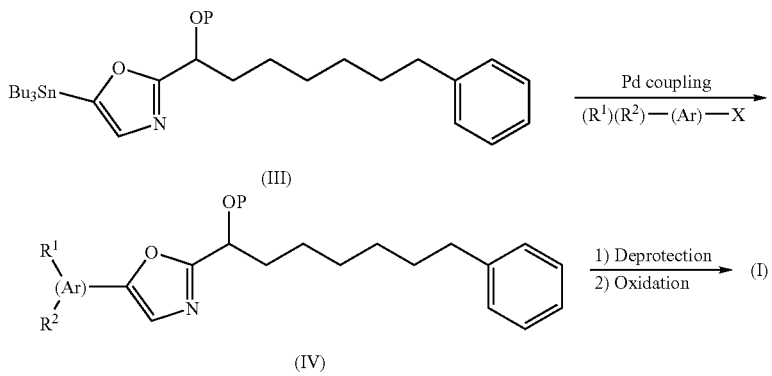

Referring to Scheme A, stannanes of formula (III), where P is a suitable hydroxyl protecting group, are prepared as previously described (Boger, *J. Med. Chem.* 2005, 48, 1849). Stannanes (III) are coupled with various aryl or heteroaryl halides using Stifle coupling procedures. Preferred conditions utilize $Pd(PPh_3)_4$ or $Pd(P(t-Bu)_3)_2$ as the catalyst. Compounds of formula (IV) are then deprotected (for example, where P is a silyl protecting group, with a silyl deprotecting agent such as TBAF) and oxidized to compounds of Formula (I) using oxidizing agents such as Dess-Martin periodinane or TPAP/NMO.

SCHEME B

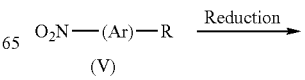

-continued

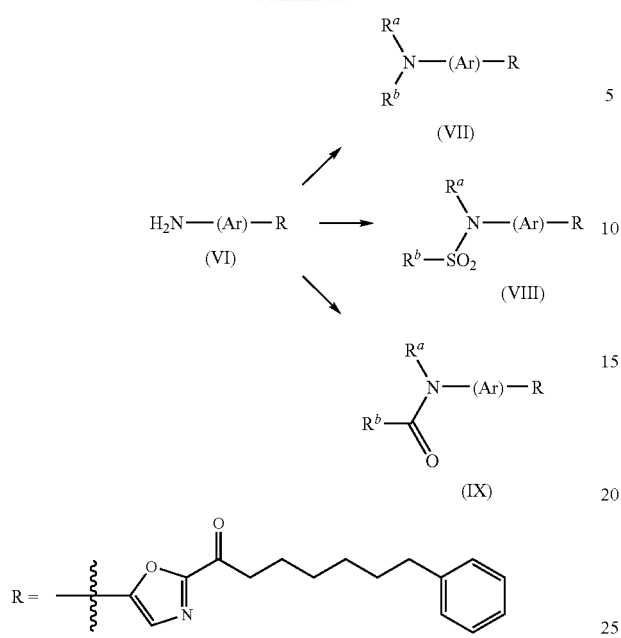

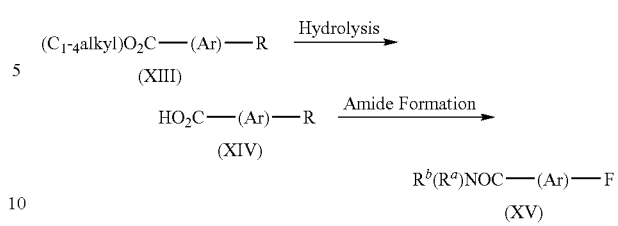

Referring to Scheme D, esters of formula (XIII), where R is defined as in Scheme B, and prepared according to Scheme A, may be hydrolyzed to acids (XIV) using a base such as LiOH. Acids (XIV) may be converted to their corresponding amides (XV) by reaction with a suitable amine under peptide coupling conditions (e.g. HOAt/EDCI). One skilled in the art will recognize that Formula (I) includes compounds of formulae (XIII), (XIV), and (XV).

One skilled in the art will recognize that transformations depicted for $R^1$ may analogously be performed for $R^2$.

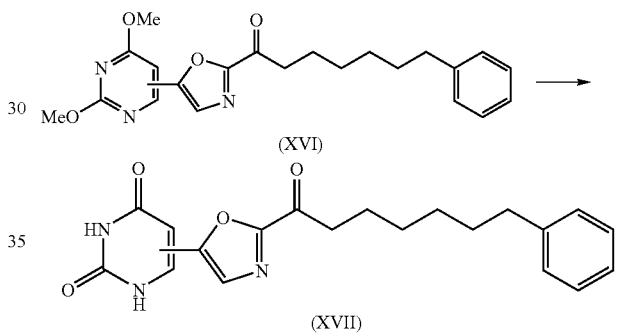

Referring to Scheme B, compounds of formula (V) may be obtained according to the methods shown in Scheme A. The nitro group may be reduced to an amino group (formula (VI)) using standard nitro reduction methods, such as exposure to $SnCl_2$ or by hydrogenation in the presence of a Pd catalyst. Amines (VI) may be alkylated via alkylation or reductive amination protocols to form amines (VII). Amines (VI) may be alternatively sulfonylated with the appropriately substituted sulfonyl chlorides to form compounds of formula (VIII). Reaction of amines (VI) with suitably substituted acid chlorides or via peptide coupling with appropriate acids (e.g. in the presence of HOAt/EDCI) generate amides (IX). Installation of the $R^a$ substituent may be accomplished before (via alkylation or reductive amination) or after (via alkylation) the sulfonylation/acylation step. One skilled in the art will recognize that Formula (I) includes compounds of formulae (VI), (VII), (VIII), and (IX).

Referring to Scheme E, pyrimidines (XVI), prepared according to Scheme A, may be converted to uracils (XVII) by treatment of a demethylating agent such as TMSI. One skilled in the art will recognize that Formula (I) includes compounds of formulae (XVI) and (XVII).

The following examples are provided to further illustrate the invention and various preferred embodiments.

The majority of the candidate inhibitors were prepared by one of two methods (FIG. 3). Sonogashira coupling (Method A) of 3a (Boger, D. L.; Miyauchi, H.; et al. *J. Med. Chem.* 2005, 48, 1849-1856) or 3b (Boger, D. L.; Miyauchi, H.; et al. *J. Med. Chem.* 2005, 48, 1849-1856) with a series of aryl iodides afforded inhibitors 4e, 4f, 4pp, 4qq, 4o-4-s, 4rr, 4ss, 4x-4 cc, 4gg-4-jj (Sonogashira, K.; Tohda, Y.; et al. *Tetrahedron Lett.* 1975, 16, 4467-4470). Hydrogenation of the alkyne provided inhibitors 5e, 5f, 5o-5s, 5pp, 5qq, 5x-5cc, 5gg-5jj. Alternatively, direct acid chloride acylation (Method B) of a Zn/Cu-metalated 5-(pyridin-2-yl)oxazole (Saikachi, H.; Kitagawa, T.; et al. *Chem. Pharm. Bull.* 1969, 27, 793-796) (6) following the protocol of Anderson et al. (Harn, N. K.; Gramer, C. J.; et al. *Tetrahedron Lett.* 1995, 36, 9453-9456) yielded inhibitors 5a-5d, 5g-5l, 5t-5v, 5nn, 5oo, 12e, 12g, 12i, 12k, 12n, 12p.

FIG. 4 summarizes the synthesis of the inhibitors that were not prepared by either Method A or B. Oxazole 6 was lithiated at C2, converted to its C2-stannane upon treatment with $Bu_3SnCl$ and subsequently treated with the corresponding

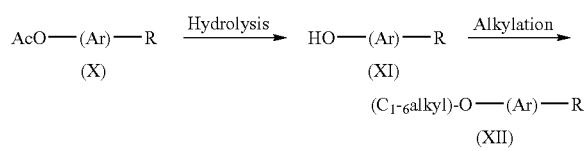

Referring to Scheme C, acetates of formula (X), where R is defined as in Scheme B, may be obtained according to the methods shown in Scheme A. Deprotection of the acetate group, using, for example, a base such as LiOH or NaOMe, gives the corresponding alcohols (XI). These alcohols may in turn be converted to ethers of formula (XII) by treatment with an appropriate alkyl halide in the presence of a base, or with an appropriate alcohol under Mitsunobu conditions (for example, $PPh_3/DEAD$). One skilled in the art will recognize that Formula (I) includes compounds of formulae (XI) and (XII).

acid chloride to afford 12a and 12b (Dondoni, A.; Fantin, G.; et al. *J. Org. Chem.* 1988, 53, 1748-1761; Dondoni, A.; Mastellari, A. R.; et al. *Synthesis* 1986, 757-760). Compound 12f was prepared by Michael addition of N-methyl-3-phenylpropylamine to enone 7. Treatment of 8 with $TiCl_4$ followed by N-methyl-2-phenylethylamine provided 12h (Pocar, D.; Stradi, R.; et al. *Tetrahedron* 1975, 31, 2427-2429; Yovell, J.; Hirsch, D.; et al. *J. Org. Chem.* 1977, 42, 850-855). Compounds 9j and 9o were transformed to a series of amino ketones upon treatment with the corresponding amine in the presence of $K_2CO_3$ in 2-butanone or by treatment with the neat amine. Esters 14a-14c were readily converted to their corresponding amides 13a-13c. α-Hydroxylation of OL-135 (2b) with the Davis reagent (Davis, F. A.; Vishwakarma, L. C.; et al. *J. Org. Chem.* 1984, 49, 3241-3243) afforded 13d. Enolization of 10 with KHMDS and subsequent treatment with 5-phenylpentanal yielded 13c. Inhibitors 5kk-5mm, 12c, 12d, 12l, 12m, 12q and 12r were prepared by oxidation (m-CPBA) of the corresponding sulfides 5t-v, 12b, 12k, and 12p.

Enzyme Assay

Enzyme assays were performed at 20-23° C. with purified recombinant rat FAAH expressed in *E. coli* (Patricelli, M. P.; Lashuel, H. A.; et al. *Biochemistry* 1998, 37, 15177-15187) (unless indicated otherwise) or with solubilized COS-7 membrane extracts from cells transiently transfected with human FAAH cDNA (Giang, D. K.; Cravatt, B. F. *Proc. Natl. Acad. Sci. U.S.A.* 1997, 94, 2238-2242) (where specifically indicated) in a buffer of 125 mM Tris/1 mM EDTA/0.2% glycerol/0.02% Triton X-100/0.4 mM Hepes, pH 9.0 buffer (Patricelli, M. P.; Patterson, J. P.; et al. *Bioorg. Med. Chem. Lett.* 1998, 8, 613-618). The initial rates of hydrolysis ($\leq$10-20% reaction) were monitored using enzyme concentrations at least three times below the measured $K_i$ by following the breakdown of $^{14}$C-oleamide and $K_i$'s (standard deviations are provided in Supporting Information tables) were established as described (Dixon plot) (Boger, D. L.; Sato, H.; et al. *Proc. Natl. Acad. Sci. U.S.A.* 2000, 97, 5044-5049). Lineweaver-Burk analysis previously established reversible, competitive inhibition (Boger, D. L.; Miyauchi, H.; et al. *J. Med. Chem.* 2005, 48, 1849-1856).

Substitution of C2 Side Chain Terminal Phenyl Group. A systematic series of aryl replacements and phenyl substitutions, aryl replacement derivatives (5a-5f), thiophene replacements 5a and 5b, 1-naphthyl substitution 5c, 2-naphthyl derivative 5d proved to be effective inhibitors. Incorporation of the more polar pyridine substituent 5e and 5f led to reductions in the $K_i$. FIG. 5 illustrates this series.

Substitution involving the terminal phenyl ring of the alpha acyl side chain provided effective inhibition and the complete range of ortho, meta, or para substituents provided effective FAAH inhibitors (5g-5oo; FIG. 5). However, the carboxylic acid derivatives (5dd-ff) that are deprotonated under the assay conditions did not display strong binding. Typically, hydrophobic or electron-withdrawing substituents enhanced the binding affinity of the inhibitors more significantly than polar or electron-donating substituents. However, and with a couple of notable exceptions, each substituent enhanced binding affinity indicative of additional favorable binding contacts within the active site. Although this may not be surprising for the hydrophobic substituents ($CH_3$, $CF_3$, F, Cl, $SCH_3 \geq OCH_3$, H), it is especially interesting that polar substituents ($CO_2CH_3$, $NO_2$, $SO_2CH_3$, $NH_2$) can be tolerated in this hydrophobic pocket and that some even enhance inhibitory potency. This appears to be especially true of the m-position where even the methylsulfone 5ll produced an inhibitor of significant potency. whereas the corresponding o- and p-methylsulfone derivatives (5kk and 5mm, respectively) were approximately 10-fold less effective. The potency of such derivatives typically ranged from 5-0.9 nM ($K_i$), displayed a variable and weak preference for the site of attachment, and the most potent members typically were the m-substituted derivatives. Significantly, 5hh (R=Cl) broke the nanomolar potency barrier providing a $K_i$ of 900 pM. Accordingly, this region provides a rich area where substituents or modifications can be introduced to enhance inhibitor potency, impact features contributing to or improving in vivo properties, and substantially enhance selectivity. The invention, therefore encompasses all hydrophobic as well as hydrophilic and ionic substitution at these positions.

Extending an alkyl m- or p-substituent revealed that 5nn (p-substituent) displayed significant potency whereas 5oo (m-substituent) was less effective.

Finally, the alkyne precursors 4 to series 5 inhibitors prepared by the Shonogashira coupling (Method A) were also examined for FAAH inhibition and the results are summarized in FIG. 6. It was observed that there was a loss in activity with the alkynes compared to their corresponding alkane derivatives (FIG. 5) suggesting that this restriction places the terminal aryl ring in a less favorable area in the FAAH active site.

Substitution along the side chain. A systematic series of heteroatoms and electron-withdrawing substituents positioned within the alpha keto side chain was also investigated (FIG. 7). Placing a heteroatom or electron-withdrawing substitutent at the 2-position of the side chain (12a-12d) β to the electrophilic carbonyl resulted in a loss in potency despite their inductive electron-withdrawing character that would be expected to enhance the electrophilic character of the carbonyl. Only the least electronegative atom of the series (X=S, 12b) displayed significant potency and the most electronegative functionality (X=$SO_2$, 12d) resulted in a significant loss in potency. A rough trend in the $K_i$ is observed as heteroatoms move along the chain where heteroatoms at each end of the chain (2- and 6-positions) are better tolerated than in the middle (3-5 positions). At each location, the substitutions exhibited a well-defined trend of $CH_2 \geq S > O > NMe > SO > SO_2$, which reflects the hydrophobic character of this region of FAAH active site. Introduction of a sulfur provided inhibitors that displayed significant potency (12b, 2-position; 12p, 6-position, 12k, 5-position). Other heteroatoms caused reduction in potency as the above delineated trend indicates. At the most tolerant position (position 6), the magnitude of these effects for sulfur, oxygen, and NMe are dampened with each providing effective inhibitors.

Figure 8:
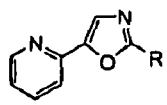
FIG. 8 illustrates a table showing a series of amides within the linking chain and hydroxyl substitutions on the chain was also explored.

A series of amides within the linking chain and hydroxyl substitutions on the chain was also explored (FIG. 8). Amide placement in the side chain led to a loss in inhibitory potency. Consistent with expectations, 13a, but not 13b or 13c, exists as the stable N-acyl hemiaminal and this is reflected in its lower ability to inhibit FAAH. Consistent with the previous series of inhibitors (FIG. 7), a well-defined trend in $K_i$ is observed as the hydroxyl substitution moves along the side chain where the hydroxyl group at each end of the side chain was better tolerated than those in the middle of the side chain. Within this series, only 13f (50%, $CDCl_3$) and 13g (50%, $CDCl_3$) exist in equilibrium with their internal hemiketal. Thus, even though 13f has a lower potency that other compounds of this series, it will prove useful to examine in vivo where the electrophilic carbonyl would potentially be less prone to metabolic reduction due to the reversible hemiketal formation.

Figure 9:
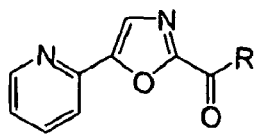
FIG. 9 illustrates is a table showing several additional side chain modifications that were examined and represent intermediates or byproducts derived from the synthesis of the preceding candidate inhibitors.

Several additional side chain modifications were examined and represent intermediates or byproducts derived from the synthesis of the preceding candidate inhibitors. The results of their examination are summarized in FIG. 9 and highlight several features. Shortening of the side chain and removal of the phenyl group of OL-135 (2b) with a small series of methyl esters (14a-14c) led to a significant progressive decrease in potency. The cyclopropyl and cyclopentyl derivatives 14d and 14e lacking the extended chain and phenyl group similarly resulted in a loss of activity. Interestingly, and in contrast, the simple α-chloroketone 14f was still a submicromolar inhibitor of FAAH although it lacked nearly all of the alpha keto side chain. Presumably this result reflects that inhibitor's increased electrophilic carbonyl reactivity which significantly increases its potency over the known inactive methyl ketone (Boger, D. L.; Miyauchi, H.; et al. *J. Med. Chem.* 2005, 48, 1849-1856). Placement of a ketone beta to the electrophilic carbonyl (14g) led to a significant loss of inhibitory potency. In this instance, the electrophilic C2 carbonyl of 14g is enolized (>95%, $CDCl_3$) and unreactive toward nucleophilic attack.

Finally two alcohol derivatives were examined, e.g., 14h and 14i, and both resulted in a substantial loss in inhibitory potency with 14h exhibiting a greater loss in activity relative to its corresponding ketone 13d.

Although inhibitory potency among the compounds of the invention varies, other factors such as lack of side effects, selectivity for the FAAH relative to other enzymes, bioavailability, ability to cross biological barriers such as the gut-blood barrier, the blood-cell barrier and the blood-brain barrier, among others, are important for development of an effective pharmaceutical compound. Consequently, lower potency does not mean that an individual compound of Formula I lacks pharmaceutical interest. For example, while pyridine substitution for phenyl on the alpha keto side chain led to lower potency, the selectivity for FAAH was increased as discussed below. Nevertheless, unless otherwise indicated by selectivity or other experimental factors described herein, the compounds of Formula I having higher inhibitory Ki's are preferred according to the invention.

Inhibition of Recombinant Human FAAH. Rat and human FAAH are very homologous (84% sequence identity), exhibit near identical substrate selectivities and inhibitor sensitivities in studies disclosed to date (Boger, D. L.; Sato, H.; et al. *Proc. Natl. Acad. Sci. U.S.A.* 2000, 97, 5044-5049), and embody an identical amidase signature sequence suggesting the observations made with rat FAAH would be analogous to those made with the human enzyme. Consequently, the inhibitors of the present inventive series were examined against the human enzyme and consistent with previous observations (Boger, D. L.; Miyauchi, H.; et al. *J. Med. Chem.* 2005, 48, 1849-1856; Romero, F. A.; Du, W.; et al. *J. Med. Chem.* 2006, submitted) were found to exhibit the same relative and absolute potencies (FIG. 10).

Selectivity Screening. Early assessments of α-ketoheterocycle inhibitors of FAAH against possible competitive enzymes (e.g., phospholipase A2, ceramidase) revealed no inhibition. Consequently a method for proteomic-wide screening capable of globally profiling all mammalian serine hydrolases was developed (Leung, D.; Hardouin, C.; et al. *Nature Biotech.* 2003, 21, 687-691) and studies have shown that the α-ketoheterocycle class of inhibitors generally are exquisitely selective for FAAH (Boger, D. L.; Miyauchi, H.; et al. *J. Med. Chem.* 2005, 48, 1849-1856; Leung, D.; Du, W.; et al. *Bioorg. Med. Chem. Lett.* 2005, 15, 1423-1428; Lichtman, A. H.; Leung, D.; et al. *J. Pharmacol. Exp. Ther.* 2004, 311, 441-448). However, two enzymes did emerge as potential competitive targets: triacylglycerol hydrolase (TGH) and an uncharacterized membrane-associated hydrolase that lacks known substrates or function (KIAA1363). In this screen, $IC_{50}$ values are typically higher than the measured $K_i$ values, but the relative potency, the magnitude of binding affinity differences and the rank order binding determined in the assay parallels that established by standard substrate assays.

Summarized in FIG. 11 are the results of the selectivity screening of selected candidate inhibitors. In general, the inhibitors were very selective for FAAH over TGH and KIAA1361. The pyridyl replacements (5e, 5f) of the terminal phenyl group of the alpha keto side chain proved very selective for FAAH over KIAA1363, but only moderately selective for FAAH over TGH. Substitution on the terminal phenyl ring of 2b also provided selective inhibitors and this was relatively independent of the substitution position (o-, m-, or p-) and whether it was electron-donating or electron-withdrawing (5j-5l vs. 5gg-5ii).

The following experimental description of individual compounds of Formula I further illustrates the present invention. These examples and their corresponding biological activities provide further information about the present invention. However, the invention is fully characterized in the foregoing Summary and the following claims. The examples are not meant to act as limitations of the invention. Additional embodiments and examples will be readily apparent to the practitioner based upon the foregoing Summary, synthetic schemes and the examples provided below.

EXPERIMENTAL

1-Oxo-1-[5-(2-pyridyl)oxazol-2-yl]-7-(3-chlorophenyl) heptane (5hh). A solution of hept-6-ynoic acid (1.90 g, 14.8 mmol) in anhydrous THF (90 mL) at −78° C. was treated with n-BuLi (2.3 M in hexanes, 14.5 mL, 33.3 mmol). After stirring for 2 min, TMSCl (5.8 mL, 46.0 mmol) was added. The reaction mixture was allowed to warm slowly to 25° C. and was stirred for 1 h. The reaction was quenched with the addition of aqueous 2 N HCl and extracted with $CH_2Cl_2$. The organic layer was dried over $Na_2SO_4$, filtered and concentrated. Column chromatography ($SiO_2$, 4×6 cm, 20% EtOAc-hexanes) afforded 7-(trimethylsilyl)hept-6-ynoic acid (2.7 g, 13.6 mmol, 92%) as a white solid: $^1$NMR ($CDCl_3$, 500 MHz) δ 2.40 (t, 2H, J=7.4 Hz), 2.24 (t, 2H, J=7.3 Hz), 1.78-1.72 (m, 2H), 1.62-1.56 (m, 2H), 0.15 (s, 9H).

A solution of 5-(2-pyridyl)oxazole (Saikachi, H.; Kitagawa, T.; et al. *Chem. Pharm. Bull.* 1969, 27, 793-796) (600 mg, 4.11 mmol) in anhydrous THF (15 mL) at −78° C. was treated dropwise with a solution of n-BuLi (2.2 M in hexanes, 2.4 mL, 4.52 mmol,) under $N_2$ and the resulting solution was stirred at −78° C. for 20 min. A solution of $ZnCl_2$ (0.5 M in THF, 18 mL, 8.22 mmol,) was added, and the mixture was warmed to 0° C. After stirring at 0° C. for 45 min, CuI (850 mg, 4.46 mmol) was added to the mixture. After the mixture was stirred at 0° C. for 10 min, a solution of 7-(trimethylsilyl) hept-6-ynoyl chloride (1.2 equiv; prepared from 7-(trimethylsilyl)hept-6-ynoic acid and oxalyl chloride) in anhydrous THF (9 mL) was added dropwise, and the mixture was stirred at 0° C. for an additional 1 h. The reaction mixture was diluted with a 1:1 mixture of hexanes and EtOAc (60 mL) and washed with 15% aqueous $NH_4OH$ (2×30 mL), water (30 mL) and saturated aqueous NaCl (30 mL). The organic layer was dried over anhydrous $Na_2SO_4$, filtered, and evaporated. Column chromatography ($SiO_2$, 4×6 cm, 30% EtOAc-hexanes) afforded 1-oxo-1-[5-(2-pyridyl)oxazol-2-yl]-7-(trimethylsilyl)hept-6-yne (3a, 875 mg, 2.68 mmol, 74%) as a tan oil: $^1$H NMR ($CDCl_3$, 400 MHz) 8.68 (m, 1H), 7.89-7.86 (m, 2H), 7.82 (td, 1H, J=7.6, 1.8 Hz), 7.34-7.31 (m, 1H), 3.15 (t, 2H, J=7.3 Hz), 2.30 (t, 2H, J=7.2 Hz), 1.94-1.86 (m, 2H), 1.68-1.60 (m, 2H), 0.14 (s, 3H); $^{13}$C NMR (CDCl$_3$, 100 MHz) ☐187.9, 157.2, 153.2, 150.0, 146.1, 137.0, 126.8, 124.1, 120.3, 106.6, 84.8, 38.4, 27.9, 22.9, 19.6, 0.0; IR (film) $v_{max}$ 2955, 2867, 2173, 1699, 1603, 1576, 1504, 1469, 1426, 1383, 1249, 1152, 1118, 1083, 1024, 929, 842, 784, 760 cm$^{-1}$; ESI-TOF m/z 327.1530 (C$_{18}$H$_{22}$N$_2$O$_2$Si+H$^+$ requires 327.1523).

A solution of 1-oxo-1-[5-(2-pyridyl)oxazol-2-yl]-7-(trimethylsilyl)hept-6-yne (3a, 570 mg, 1.75 mmol, 1 equiv) in anhydrous THF (6 mL) at 0° C. was treated with a solution of Bu$_4$NF in THF (1 M, 2.1 mL, 2.1 mmol). After stirring for 35 min at 0° C., the reaction mixture was quenched with H$_2$O and extracted with EtOAc. The organic layer was dried over anhydrous Na$_2$SO$_4$, filtered and evaporated. Column chromatography (SiO$_2$, 2.5×3 cm, 30% EtOAc-hexanes) afforded 1-oxo-1-[5-(2-pyridyl)oxazol-2-yl]-hept-6-yne (3b, 340 mg, 1.36 mmol, 77%) as a tan solid: $^1$H NMR (CDCl$_3$, 500 MHz) δ 8.68-8.66 (m, 1H), 7.89-7.86 (m, 2H), 7.82 (td, 1H, J=7.6, 1.8 Hz), 7.34-7.31 (m, 1H), 3.15 (t, 2H, J=7.3 Hz), 2.27 (td, 2H, J=7.2, 2.7 Hz), 1.96 (t, 2H, J=2.7 Hz), 1.94-1.88 (m, 2H), 1.68-1.62 (m, 2H); $^{13}$C NMR (CDCl$_3$, 125 MHz) δ 187.9, 157.2, 153.2, 150.1, 146.2, 137.1, 126.8, 124.1, 120.3, 83.8, 68.7, 38.4, 27.7, 22.9, 18.2; IR (film) $v_{max}$ 2938, 2867, 2115, 1698, 1603, 1575, 1505, 1470, 1426, 1385, 1283, 1245, 1127, 1086, 1024, 991, 962, 853, 785, 743 cm$^{-1}$; ESI-TOF m/z 255.1135 (C$_{15}$H$_{14}$N$_2$O$_2$+H$^+$ requires 255.1128).

A solution of 1-chloro-3-iodobenzene (49 mg, 0.205 mmol) in anhydrous THF (0.5 mL) was treated with PdCl$_2$(PPh$_3$)$_2$ (7 mg, 0.01 mmol). After stirring for 5 min at 25° C., Et$_3$N (0.2 mL, 0.603 mmol) and CuI (10 mg, 0.053 mmol) were added. The suspension was stirred for 35 min and 1-oxo-1-[5-(2-pyridyl)oxazol-2-yl]-hept-6-yne (3b, 30 mg, 0.067 mmol) was added. After stirring for 14 h at 25° C., the reaction mixture was filtered through Celite and concentrated. PTLC (SiO$_2$, 50% EtOAc-hexanes) afforded 1-oxo-1-[5-(2-pyridyl)oxazol-2-yl]-7-(3-chlorophenyl)hept-6-yne (4hh, 24 mg, 0.066 mmol, 56%) as a yellow solid: mp 50-51° C.; $^1$H NMR (CDCl$_3$, 500 MHz) δ 8.68-8.66 (m, 1H), 7.89-7.86 (m, 2H), 7.82 (td, 1H, J=7.7, 1.8 Hz), 7.38 (m, 1H), 7.34-7.31 (m, 1H), 7.27-7.18 (m, 3H), 3.20 (t, 2H, J=7.4 Hz), 2.49 (t 2H, J=7.0 Hz), 2.00-1.95 (m, 2H), 1.77-1.71 (m, 2H); $^{13}$C NMR (CDCl$_3$, 125 MHz) δ 187.9, 157.2, 153.3, 150.1, 146.2, 137.1, 133.9, 131.4, 129.6, 129.3, 127.8, 126.8, 125.5, 124.1, 120.3, 90.9, 79.8, 38.5, 27.8, 23.1, 19.1; IR (film) $v_{max}$ 3061, 2932, 2865, 2230, 1703, 1592, 1575, 1558, 1505, 1471, 1426, 1385, 1283, 1243, 1152, 1081, 1065, 1023, 990, 962, 930, 880, 784, 740, 683 cm$^{-1}$; ESI-TOF m/z 365.1058 (C$_{21}$H$_{17}$ClN$_2$O$_4$+H$^+$ requires 365.1051).

A solution of the oxo-1-[5-(2-pyridyl)oxazol-2-yl]-7-(3-chlorophenyl)hept-6-yne (4hh, 15 mg, 0.041 mmol) in anhydrous THF (1 mL) was treated with a catalytic amount of Raney nickel (washed before use with THF). The reaction mixture was purged with H$_2$ and stirred at 25° C. overnight. The suspension was filtered through Celite and concentrated. The crude product was dissolved in anhydrous CH$_2$Cl$_2$ (2 mL) and treated with Dess-Martin reagent (29 mg, 0.068 mmol). After stirring for 3 h at 25° C., the reaction mixture was quenched with saturated aqueous Na$_2$CO$_3$ and saturated aqueous Na$_2$S$_2$O$_3$. After stirring for 15 min, the mixture was extracted with CH$_2$Cl$_2$. The organic layer was dried over Na$_2$SO$_4$, filtered and concentrated. PTLC (SiO$_2$, 40% EtOAc-hexanes) afforded the title compound (5hh, 10 mg, 0.027 mmol, 67%) as a white solid: mp 91-92° C.; $^1$H NMR (CDCl$_3$, 600 MHz) ☐8.68-8.66 (m, 1H), 7.89-7.86 (m, 2H), 7.82 (td, 1H, J=7.8, 1.4 Hz), 7.34-7.31 (m, 1H), 7.21-7.14 (m, 3H), 7.04 (d, 1H, J=7.5 Hz), 3.11 (t, 2H, J=7.4 Hz), 2.59 (t, 2H, J=7.4 Hz), 1.81-1.76 (m, 2H), 1.65-1.60 (m, 2H), 1.46-1.36 (m, 4H); $^{13}$C NMR (CDCl$_3$, 125 MHz) ☐188.4, 157.3, 153.2, 150.1, 146.3, 144.7, 137.1, 133.9, 129.5, 128.5, 126.8, 126.6, 124.1, 120.4, 39.0, 35.5, 31.0, 28.8, 23.8; IR (film) $v_{max}$ 2930, 2856, 1698, 1601, 1575, 1505, 1470, 1426, 1385, 1285, 1081, 1035, 990, 962, 935, 783, 741, 696 cm$^{-1}$; ESI-TOF m/z 369.1363 (C$_{21}$H$_{21}$ClN$_2$O$_2$+H$^+$ requires 369.1364).

General Procedure A. A solution of the aldehyde (1 equiv) and BrPh$_3$P(CH$_2$)$_5$CO$_2$H (S1, 1.05 equiv) in anhydrous THF (20 mL/4.46 mmol of aldehyde) at −78° C. was treated with a suspension of t-BuOK (1.4 equiv) in anhydrous THF (8 mL). The reaction mixture was allowed to warm at 0° C. and was stirred for 20 h. The reaction mixture was concentrated, diluted with aqueous 4 N NaOH and extracted with EtOAc. The aqueous phase was treated with aqueous 4 N HCl and extracted with EtOAc. The organic layer was dried over Na$_2$SO$_4$, filtered and concentrated. Flash chromatography (SiO$_2$) afforded the corresponding unsaturated acid. The mixture of isomers (1 equiv) in EtOAc (10 mL) was treated with 10% Pd/C (0.2 equiv) and purged with H$_2$. After stirring for 24 h at 25° C., the reaction mixture was filtered through Celite and concentrated to afford the product.

General Procedure B. A solution of 5-(2-pyridyl)oxazole (1.0 equiv) in anhydrous THF (3 mL/0.34 mmol) at −78° C. was treated dropwise with a solution of n-BuLi in hexanes (2.5 M, 1.2 equiv) under N$_2$ and the resulting solution was stirred at −78° C. for 35 min. A solution of ZnCl$_2$ in THF (0.5 M, 2 equiv) was added to the mixture and the mixture was allowed to warm to 0° C. After stirring at 0° C. for 45 min, CuI (1.2 equiv) was added to the mixture. After the mixture was stirred at 0° C. for 15 min, a solution of the acid chloride (1.2 equiv; prepared from the corresponding carboxylic acid and oxalyl chloride) in anhydrous THF (2 mL) was added dropwise, and the mixture was stirred for an additional 1 h. The reaction mixture was quenched with addition of saturated aqueous NaHCO$_3$ and extracted with EtOAc. The organic layer was filtered through Celite, dried over anhydrous Na$_2$SO$_4$, filtered and evaporated to yield the crude product, which was purified by flash chromatography (SiO$_2$).

General Procedure C. A solution of 5-(2-pyridyl)oxazole (1.0 equiv) in anhydrous THF (5.0 mL/0.51 mmol) at −78° C. was treated dropwise with a solution of n-BuLi in hexanes (2.5 M, 1.1 equiv) under N$_2$ and the resulting solution was stirred at −78° C. for 20 min. A solution of ZnCl$_2$ in THF (0.5 M, 2.0 equiv) was added to the mixture, and the mixture was warmed to 0° C. After stirring at 0° C. for 45 min, CuI (1.0 equiv) was added to the mixture. After the mixture was stirred at 0° C. for 10 min, a solution of the acid chloride (1.2 equiv; prepared from the corresponding carboxylic acid and oxalyl chloride) in anhydrous THF (3.0 mL) was added dropwise, and the mixture was stirred at 0° C. for an additional 1 h. The reaction mixture was diluted with a 1:1 mixture of hexanes and EtOAc (60 mL) and washed with 15% aqueous NH$_4$OH (2×30 mL), water (30 mL) and saturated aqueous NaCl (30 mL). The organic layer was dried over anhydrous Na$_2$SO$_4$, filtered, and evaporated. Column chromatography (SiO$_2$) afforded the product.

General Procedure D. A solution of the alkyne (1.0 equiv) in anhydrous THF (0.5 mL/0.12 mmol of alkyne) was treated with the aryl iodide (1.5 equiv), Ag$_2$CO$_3$ (0.7 equiv), Bu$_4$NCl (1.8 equiv) and PdCl$_2$(PPh$_3$)$_2$ (0.10 equiv). After stirring for 22 h at 90° C., the reaction was quenched with aqueous saturated NaCl and extracted with EtOAc. The organic layer was dried over Na$_2$SO$_4$, filtered and concentrated. Chromatography (SiO$_2$) afforded the product.

General Procedure E. A solution of the aryl iodide (1.6 equiv) in anhydrous THF (0.6 mL/0.19 mmol of alkyne) was treated with PdCl$_2$(PPh$_3$)$_2$ (0.07 equiv). After stirring for 5 min at 25° C., Et$_3$N (9 equiv) and CuI (0.35 equiv) were added. The suspension was stirred for 35 min and 1-oxo-1-[5-(2-pyridyl)oxazol-2-yl]-hept-6-yne (3b (Boger, D. L.; Miyauchi, H.; et al. *J. Med. Chem.* 2005, 48, 1849-1856), 1 equiv) was added. After stirring for 14 h at 25° C., the reaction mixture was filtered through Celite and concentrated. Flash chromatography (SiO$_2$) afforded the product.

General Procedure F. A solution of the alkyne (1 equiv) in EtOAc (0.5 mL/0.027 mmol of alkyne) was treated with 10% Pd/C (0.2 equiv). The reaction mixture was purged with H$_2$ and stirred overnight at 25° C. The suspension was filtered through Celite and concentrated.

General Procedure G. A solution of the alkyne (1 equiv) in anhydrous THF (1 mL/0.038 mmol of alkyne) was treated with a catalytic amount of Raney nickel (washed before use with THF). The reaction mixture was purged with H$_2$ and stirred at 25° C. overnight. The suspension was filtered through Celite and concentrated. The crude product was dissolved with anhydrous CH$_2$Cl$_2$ (2 mL) and treated with Dess-Martin reagent (1.5 equiv). After stirring for 3 h at 25° C., the reaction mixture was quenched with saturated aqueous Na$_2$CO$_3$ and saturated aqueous Na$_2$S$_2$O$_3$. After stirring for 15 min, the mixture was extracted with CH$_2$Cl$_2$. The organic layer was dried over Na$_2$SO$_4$, filtered and concentrated. Chromatography (SiO$_2$) afforded the product.

General Procedure H. A solution of the sulfide (1.0 equiv) in anhydrous CH$_2$Cl$_2$ (0.7 mL/0.050 mmol of sulfide) at 0° C. was treated with m-CPBA (2.2 equiv). After 1 h, the reaction mixture was quenched with saturated aqueous NaHCO$_3$ and extracted with CH$_2$Cl$_2$. The organic layer was dried on Na$_2$SO$_4$, filtered and concentrated. Chromatography (SiO$_2$) afforded the product.

General Procedure I. A solution of the alkyne (1 equiv) in a mixture of THF/MeOH (1 mL, 1/1; for 0.12 mmol of alkyne) was treated with 10% Pd/C (0.2 equiv). The suspension was purged under H$_2$ and stirred for 20 h at 25° C. 10% Pd/C (0.2 equiv) was added again and the reaction mixture was stirred for an additional 20 h at 25° C. Chromatography (SiO$_2$) afforded the product.

General Procedure J. A solution of the carbamate (1 equiv) in CH$_2$Cl$_2$ (0.2 mL/0.045 mmol of carbamate) at 0° C. was treated with 0.2 mL of TFA. After stirring for 1 h at 0° C., the reaction mixture was concentrated, diluted with aqueous saturated NaHCO$_3$ and extracted with CH$_2$Cl$_2$. The organic layer was dried over Na$_2$SO$_4$, filtered and concentrated. Chromatography (SiO$_2$) afforded the product.

General Procedure K. A solution of the acid (1 equiv; prepared by hydrogenation of the 4-hydroxycinnamic acid) in anhydrous DMF (16 mL/4.2 mmol of acid) at 0° C. was treated with Bu$_4$NI (0.01 equiv) and a suspension of NaH (60% in mineral oil, 2.7 equiv) in anhydrous DMF (10 mL). After stirring for 10 min, benzyl bromide (1.3 equiv) was added dropwise. The reaction mixture was allowed to warm at 25° C. and was stirred overnight. The reaction was quenched with aqueous 10% HCl and extracted with EtOAc. The organic layer was washed with saturated aqueous NH$_4$Cl, dried and concentrated. Column chromatography (SiO$_2$) afforded the product.

General Procedure L. The methyl ester (1 equiv) was dissolved in THF (0.15 mL/0.033 mmol) and LiOH (1.1 equiv) was added. The reaction mixture was stirred at room temperature overnight, diluted with H$_2$O and acidified to pH 2 with aqueous 1 N HCl. The acidic aqueous phase was extracted with EtOAc and the organic extracts were combined, dried over anhydrous Na$_2$SO$_4$ and concentrated. Preparative thin layer chromatography (SiO$_2$) afforded the pure acids.

General Procedure M. A solution of the sulfide (1 equiv) in anhydrous CH$_2$Cl$_2$ (0.1 M) was cooled to 0° C. and treated with m-CPBA (1.0 or 1.5 equiv). The suspension was stirred for 2 h and quenched with saturated aqueous NaHCO$_3$. The organic layer was dried over anhydrous Na$_2$SO$_4$, filtered and concentrated. PTLC (66% EtOAc-hexanes, SiO$_2$) afforded in the order of elution the sulfones and the sulfoxides in good combined yields.

General Procedure N. The methyl ester (1.0 equiv) was dissolved in 1:1 THF:H$_2$O (4 mL/0.62 mmol of methyl ester) and LiOH (1.0 equiv) was added. After stirring at room temperature for 6 h, the reaction mixture was concentrated and the residue dried under high vacuum. The dried lithium carboxylate salt was dissolved in anhydrous DMF (5 mL) and HATU (1.0 equiv) was added. The reaction mixture was stirred for 10 min before adding a solution containing the requisite amine (1.1 equiv) and i-Pr$_2$NEt (2.1 equiv) in anhydrous DMF (2 mL). After stirring at room temperature for 1 h, the DMF was removed in vacuo and the residue taken up into EtOAc. The organic layer was washed successively with aqueous 0.1 N HCl, 0.1 N NaOH and H$_2$O, and then dried over anhydrous Na$_2$SO$_4$ and concentrated. The crude amides were purified using PTLC (SiO$_2$).

General Procedure O. The TIPS ether (1 equiv) was dissolved in anhydrous THF (0.5 mL/0.12 mmol of TIPS ether) under Ar and cooled to 0° C. Bu$_4$NF (1.0 M solution in THF, 1.3 equiv) was added dropwise and the reaction mixture stirred for 30 min. The ice bath was removed and the reaction mixture was allowed to stir for 3 h at room temperature. The THF was removed under a stream of N$_2$ and the residue taken up into Et$_2$O and washed with water. The organic phase was dried over anhydrous Na$_2$SO$_4$ and concentrated. PTLC (SiO$_2$) afforded the alcohol.

General Procedure P. A solution of the alcohol (1 equiv) in anhydrous CH$_2$Cl$_2$ (0.2 M) at 0° C. was treated with PCC (1.5 equiv) and the mixture was stirred for 45 min. The reaction mixture was allowed to warm at 25° C. and stirred for 3 h. The suspension was filtered through Celite and concentrated. Column chromatography (SiO$_2$) afforded the aldehyde.

General Procedure Q. A solution of the aldehyde (1 equiv) in anhydrous THF (65 mL/20.0 mmol of aldehyde) at 0° C. was treated with the Grignard reagent (1.2 equiv). After stirring for 30 min, the reaction mixture was quenched with saturated aqueous NH$_4$Cl. The organic layer was extracted with EtOAc, dried over Na$_2$SO$_4$, filtered and concentrated. Column chromatography (EtOAc-hexanes) afforded the alcohol. A solution of the alcohol (1 equiv) in anhydrous THF at 0° C. was treated with NaH (1.2 equiv). After 15 min, TIPS-OTf (1.2 equiv) was added dropwise and the reaction mixture was allowed to warm to 25° C. After 1 h, the reaction was quenched with saturated aqueous NH$_4$Cl. The organic phase was extracted with EtOAc, dried over Na$_2$SO$_4$, filtered and concentrated. Column chromatography (SiO$_2$) afforded the TIPS protected alcohol.

General Procedure R. A solution of the benzyl protected alcohol (1 equiv) in EtOAc (0.22 M) was treated with 10% Pd/C (0.2 equiv). The reaction mixture was purged with H$_2$ and stirred overnight at 25° C. The suspension was filtered through Celite, concentrated and purified by column chromatography (SiO$_2$) to afford the alcohol.

General Procedure S. A solution of the alcohol (1 equiv) in anhydrous DMF (0.14 M) was treated with PDC (3 equiv). After stirring at 25° C. for 20 h, the reaction mixture was quenched with saturated aqueous NH$_4$Cl. The organic layer was extracted with CH$_2$Cl$_2$, dried over Na$_2$SO$_4$, filtered and concentrated. Column chromatography (SiO$_2$) afforded the carboxylic acid.

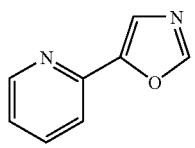

2-Oxazol-5-yl-pyridine (6) (Saikachi, H.; Kitagawa, T.; et al. Chem. Pharm. Bull. 1969, 27, 793-796). A solution of 2-pyridinecarboxaldehyde (2.3 g, 21.3 mmol) in anhydrous MeOH (70 mL) was treated with tosylmethyl isocyanide (4.4 g, 22.6 mmol) and K$_2$CO$_3$ (3.4 g, 24.4 mmol). After 2 h at reflux, the mixture was concentrated, diluted with saturated aqueous NaHCO$_3$ and extracted with CH$_2$Cl$_2$. The organic layers were combined, dried (Na$_2$SO$_4$) and concentrated. Chromatography (SiO$_2$, 40-50% EtOAc-hexanes gradient elution) provided 6 as a tan oil (3.10 g, 97%): $^1$H NMR (CDCl$_3$, 400 MHz) δ 8.55-8.53 (m, 1H), 7.90 (s, 1H), 7.66 (td, J=7.8, 1.8 Hz, 1H), 7.62 (s, 1H), 7.56 (d, J=7.8 Hz, 1H), 7.14 (ddd, J=7.8, 4.9, 1.2 Hz, 1H).

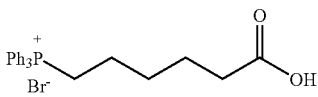

6-(Triphenylphosphonium bromide)-hexanoic acid (S1, (BrPh$_3$P(CH$_2$)$_5$CO$_2$H)). A solution of 6-bromohexanoic acid (3.9 g, 20.0 mmol, 1 equiv) in anhydrous acetonitrile (16 mL) was treated with triphenylphosphine (6.3 g, 24.0 mmol, 1.2 equiv) and warmed at reflux for 20 h. The reaction mixture was concentrated and the crude product was purified by column chromatography (SiO$_2$, 5.5×8 cm, 50-100% EtOAc-hexanes gradient and then 5% MeOH—CH$_2$Cl$_2$) to afford S1 (8.7 g, 19.0 mmol, 95%) as a white solid: $^1$H NMR (CDCl$_3$, 400 MHz) δ 7.78-7.67 (m, 15H), 3.58 (m, 2H), 2.33 (m, 2H), 1.63 (m, 4H).

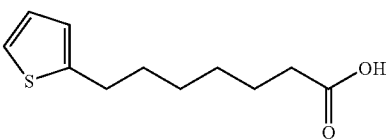

7-(Thien-2-yl)heptanoic acid (S2). The title compound was prepared from thiophene-2-carboxaldehyde and BrPh$_3$P(CH$_2$)$_5$CO$_2$H (S1) following general procedure A. Column chromatography (SiO$_2$, 3.5×7 cm, 30% EtOAc-hexanes) afforded S2 (440 mg, 2.1 mmol, 47%, 2 steps) as a white solid: $^1$H NMR (CDCl$_3$, 500 MHz) δ 7.24 (dd, 1H, J=4.8, 3.1 Hz), 6.94-6.92 (m, 2H), 2.63 (t, 2H, J=7.7 Hz), 2.36 (t, 2H, J=7.3 Hz), 1.68-1.61 (m, 4H), 1.42-1.33 (m, 4H); $^{13}$C NMR (CDCl$_3$, 125 MHz) δ 180.2, 145.5, 128.0, 126.6, 123.9, 34.0, 30.4, 30.0, 28.6 (2C), 24.4.

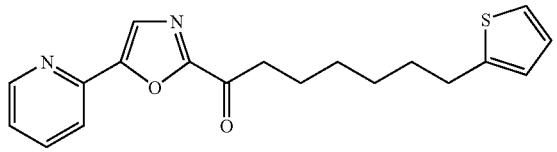

1-Oxo-1-[5-(2-pyridyl)oxazol-2-yl]-7-(2-thienyl)heptane (5a). The title compound was prepared from 5-(2-pyridyl)oxazole (6) and 7-(thien-2-yl)heptanoic (S2) following general procedure B. PTLC (SiO$_2$, 40% EtOAc-hexanes) afforded 5a (18 mg, 0.05 mmol, 16%) as a white solid: $^1$H NMR (CDCl$_3$, 500 MHz) δ 8.67 (m, 1H), 7.88-7.85 (m, 2H), 7.82 (td, 1H, J=7.8, 1.8 Hz), 7.34-7.31 (m, 1H), 7.10 (dd, 1H, J=5.2, 1.1 Hz), 6.91 (dd, 1H, J=5.2, 3.3 Hz), 6.79-6.77 (m, 1H), 3.12 (t, 2H, J=7.3 Hz), 2.84 (t, 2H, J=7.7 Hz), 1.80 (m, 2H), 1.71 (m, 2H), 1.47-1.41 (m, 4H); $^{13}$C NMR (CDCl$_3$, 125 MHz) δ 188.5, 157.3, 153.3, 150.1, 146.3, 145.5, 137.1, 126.8, 126.6, 124.1, 124.0, 122.8, 120.4, 39.0, 31.5, 29.8, 28.8, 28.7, 23.9; IR (film) ν$_{max}$ 2929, 2854, 1700, 1602, 1576, 1502, 1468, 1425, 1382, 1282, 1236, 1118, 1081, 1040, 989, 962, 849, 784, 694 cm$^{-1}$; ESI-TOF m/z 341.1324 (C$_{19}$H$_{20}$N$_2$O$_2$S+H$^+$ requires 341.1318).

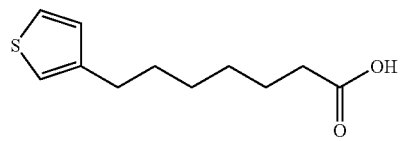

7-(Thien-3-yl)heptanoic acid (S3). The title compound was prepared from 3-thiophenecarboxaldehyde and BrPh$_3$P(CH$_2$)$_5$CO$_2$H (S1) following general procedure A. No further purification was required to yield S3 (430 mg, 2.0 mmol, 46%, 2 steps) as a white solid: $^1$H NMR (CDCl$_3$, 500 MHz) δ 7.24 (dd, 1H, J=4.8, 3.1 Hz), 6.94-6.92 (m, 2H), 2.63 (t, 2H, J=7.7 Hz), 2.36 (t, 2H, J=7.3 Hz), 1.68-1.61 (m, 4H), 1.42-1.33 (m, 4H); $^{13}$C NMR (CDCl$_3$, 125 MHz) δ 183.3, 142.9, 128.2, 125.1, 119.8, 34.0, 30.3, 30.1, 28.8 (2C), 24.5.

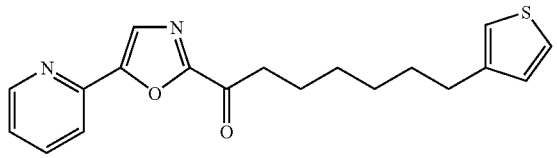

1-Oxo-1-[5-(2-pyridyl)oxazol-2-yl]-7-(3-thienyl)heptane (5b). The title compound was prepared from 5-(2-pyridyl)oxazole (6) and 7-(thien-3-yl)heptanoic (S3) acid using general procedure B. PTLC (SiO$_2$, 40% EtOAc-hexanes) afforded 5b (42 mg, 0.12 mmol, 26%) as a white solid: $^1$H NMR (CDCl$_3$, 500 MHz) δ 8.67 (m, 1H), 7.88 (s, 1H), 7.87-7.85 (m, 2H), 7.80 (td, 1H, J=7.8, 1.8 Hz), 7.35-7.31 (m, 1H), 7.23 (dd, 1H, J=4.9, 3.1 Hz), 7.01-6.99 (m, 2H), 3.11 (t, 2H, J=7.3 Hz), 2.64 (t, 2H, J=7.7 Hz), 1.79 (m, 2H), 1.65 (m, 2H), 1.48-1.37 (m, 4H); $^{13}$C NMR (CDCl$_3$, 125 MHz) δ 188.4, 157.3, 153.2, 150.1, 146.2, 142.9, 137.1, 128.2, 126.8, 125.1, 124.1, 120.3, 119.8, 39.0, 30.3, 30.1, 28.9 (2C), 23.9; IR (film) $v_{max}$ 2929, 2855, 1699, 1602, 1576, 1502, 1468, 1425, 1382, 1282, 1151, 1118, 1081, 1036, 989, 962, 852, 783 cm$^{-1}$; ESI-TOF m/z 341.1316 ($C_{19}H_{20}N_2O_2S+H^+$ requires 341.1318).

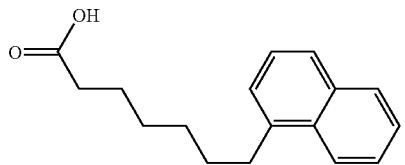

7-(1-Naphthyl)heptanoic acid (S4). The title compound was prepared from 1-naphthaldehyde and BrPh$_3$P(CH$_2$)$_5$CO$_2$H (S1) following general procedure A. No further purification was required to yield S4 (260 mg, 1.01 mmol, 33%, 2 steps) as a white solid: $^1$H NMR (CDCl$_3$, 500 MHz) δ 8.04 (d, 1H, J=8.0 Hz), 7.86 (d, 1H, J=8.0 Hz), 7.71 (d, 1H, J=8.0 Hz), 7.53-7.46 (m, 2H), 7.40 (t, 1H, J=7.7 Hz), 7.32 (d, 1H, J=6.6 Hz), 3.08 (t, 2H, J=7.3 Hz), 2.37 (t, 2H, J=7.3 Hz), 1.80-1.74 (m, 2H), 1.70-1.64 (m, 2H), 1.50-1.43 (m, 4H).

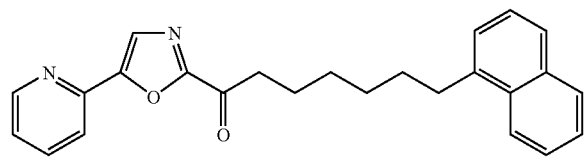

1-Oxo-1-[5-(2-pyridyl)oxazol-2-yl]-7-(1-naphthyl)heptane (5c). The title compound was prepared from 5-(2-pyridyl)oxazole (6) and 7-(naphthalen-1-yl)heptanoic acid (S4) using general procedure B. PTLC (SiO$_2$, 40% EtOAc-hexanes) afforded 5c (33 mg, 0.085 mmol, 21%) as a yellow oil: $^1$H NMR (CDCl$_3$, 500 MHz) δ 8.67 (m, 1H), 8.04 (d, 1H, J=8.5 Hz), 7.89 (s, 1H), 7.87-7.80 (m, 3H), 7.70 (d, 1H, J=8.1 Hz), 7.53-7.45 (m, 2H), 7.40 (t, 1H, J=7.5 Hz), 7.34-7.30 (m, 1H), 3.13 (t, 2H, J=7.4 Hz), 3.08 (t, 2H, J=7.7 Hz), 1.84-1.75 (m, 4H), 1.53-1.47 (m, 4H); $^{13}$C NMR (CDCl$_3$, 100 MHz) δ 188.4, 157.3, 153.2, 150.1, 146.2, 138.7, 137.0, 133.8, 131.8, 128.7, 126.8, 126.4, 125.8, 125.6, 125.5, 125.3, 124.1, 123.8, 120.3, 39.0, 32.9, 30.6, 29.4, 29.0, 23.9; IR (film) $v_{max}$ 3054, 2931, 2856, 1699, 1602, 1575, 1558, 1505, 1470, 1426, 1385, 1283, 1238, 1151, 1118, 1081, 1029, 990, 963, 936, 852, 782, 740, 712, 694 cm$^{-1}$; ESI-TOF m/z 385.1916 ($C_{25}H_{24}N_2O_2+H^+$ requires 385.1916).

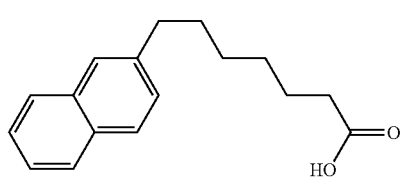

7-(2-Naphthyl)heptanoic acid (S5). This material was prepared from 2-naphthaldehyde and BrPh$_3$P(CH$_2$)$_5$CO$_2$H (S1) following general procedure A. No further purification was required to yield S5 (310 mg, 1.21 mmol, 34%, 2 steps) as a white solid: $^1$H NMR (CDCl$_3$, 500 MHz) δ 7.89-7.84 (m, 3H), 7.69 (s, 1H), 7.54-7.47 (m, 2H), 7.41 (dd, 1H, J=8.4, 1.8 Hz), 2.79 (t, 2H, J=7.3 Hz), 2.39 (t, 2H, J=7.3 Hz), 1.75-1.66 (m, 4H), 1.43-1.40 (m, 4H).

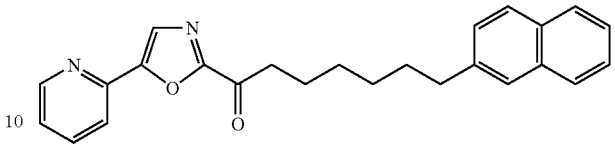

1-Oxo-1-[5-(2-pyridyl)oxazol-2-yl]-7-(2-naphthyl)heptane (5d). The title compound was prepared from 5-(2-pyridyl)oxazole (6) and 7-(2-naphthyl)heptanoic (S5) acid using general procedure B. PTLC (SiO$_2$, 40% EtOAc-hexanes) afforded 5d (33 mg, 0.085 mmol, 21%) as a yellow oil: $^1$H NMR (CDCl$_3$, 400 MHz) δ 8.67 (m, 1H), 7.88-7.75 (m, 6H), 7.60 (s, 1H), 7.47-7.39 (m, 2H), 7.35-7.30 (m, 2H), 3.12 (t, 2H, J=7.3 Hz), 2.78 (t, 2H, J=7.3 Hz), 1.82-1.72 (m, 4H), 1.47-1.43 (m, 4H); $^{13}$C NMR (CDCl$_3$, 100 MHz) δ 188.4, 163.9, 157.3, 153.2, 150.0, 146.2, 140.1, 137.0, 133.5, 131.8, 127.7, 127.5, 127.3, 126.8, 126.2, 125.7, 124.9, 124.0, 120.3, 39.0, 35.9, 31.0, 28.9 (2C), 23.8; IR (film) $v_{max}$ 3054, 2930, 2855, 1700, 1652, 1602, 1575, 1558, 1505, 1471, 1426, 1385, 1300, 1283, 1239, 1153, 1122, 1082, 1037, 990, 963, 852, 817, 784, 742 cm$^{-1}$; ESI-TOF m/z 385.1913 ($C_{25}H_{24}N_2O_2+H^+$ requires 385.1916).

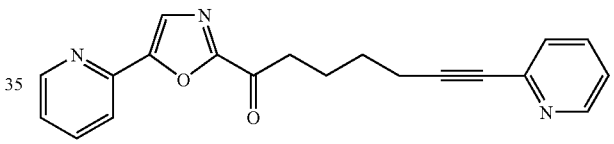

1-Oxo-1-[5-(2-pyridyl)oxazol-2-yl]-7-(2-pyridyl)hept-6-yne (4e). The title compound was prepared from 1-oxo-1-[5-(2-pyridyl)oxazol-2-yl]-hept-6-yne (3b (Boger, D. L.; Miyauchi, H.; et al. J. Med. Chem. 2005, 48, 1849-1856)) and 2-iodopyridine following general procedure E. PTLC (SiO$_2$, 50% EtOAc-hexanes +1% Et$_3$N) afforded 4e (21 mg, 0.06 mmol, 54%) as a pale yellow oil: $^1$H NMR (CDCl$_3$, 600 MHz) δ 8.67 (app d, 1H, J=4.4 Hz), 8.53 (d, 1H, J=4.9 Hz), 7.88-7.85 (m, 2H), 7.81 (td, 1H, J=7.5, 1.3 Hz), 7.60 (td, 1H, J=7.9, 1.7 Hz), 7.37 (d, 1H, J=7.9 Hz), 7.32 (dd, 1H, J=7.0, 4.9 Hz), 7.17 (dd, 1H, J=7.4, 4.9 Hz), 3.19 (t, 2H, J=7.2 Hz), 2.53 (t, 2H, J=7.0 Hz), 2.01-1.95 (m, 2H), 1.80-1.74 (m, 2H); $^{13}$C NMR (CDCl$_3$, 150 MHz) δ 187.9, 157.2, 153.2, 150.0, 149.7, 146.2, 143.6, 137.0, 136.0, 126.8 (2C), 124.1, 122.3, 120.3, 90.1, 80.7, 38.4, 27.6, 23.1, 19.1; IR (film) $v_{max}$ 2928, 2231, 1699, 1602, 1582, 1506, 1465, 1429, 1386, 1283, 1151, 1084, 1023, 989, 962, 782 cm$^{-1}$; ESI-TOF m/z 332.1396 ($C_{20}H_{17}N_3O_2+H^+$ requires 332.1393).

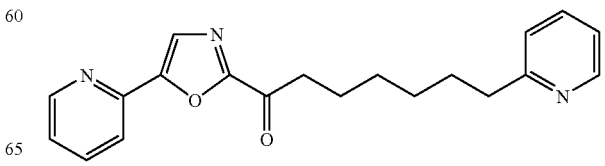

1-Oxo-1-[5-(2-pyridyl)oxazol-2-yl]-7-(2-pyridyl)heptane (5e). The title compound was prepared from 1-oxo-1-[5-(2-pyridyl)oxazol-2-yl]-7-(2-pyridyl)hept-6-yne (4e) following general procedure F. PTLC (SiO$_2$, 50% EtOAc-hexanes) afforded 5e (7 mg, 0.021 mmol, 78%) as a pale yellow solid: $^1$H NMR (CDCl$_3$, 500 MHz) δ 8.67 (app d, 1H, J=4.4 Hz), 8.52 (d, 1H, J=4.4 Hz), 7.87-7.83 (m, 2H), 7.81 (td, 1H, J=7.7, 1.5 Hz), 7.59 (td, 1H, J=7.7, 1.8 Hz), 7.33-7.30 (m, 1H), 7.14 (d, 2H, J=7.7 Hz), 7.10 (dd, 1H, J=6.4, 4.9 Hz), 3.11 (t, 2H, J=7.3 Hz), 2.79 (t, 2H, J=7.7 Hz), 1.82-1.73 (m, 4H), 1.49-1.41 (m, 4H); $^{13}$C NMR (CDCl$_3$, 125 MHz) δ 188.5, 162.2, 157.3, 153.2, 150.1, 149.1, 146.3, 137.1, 136.3, 126.8, 124.1, 122.7, 120.9, 120.4, 39.0, 38.2, 29.6, 29.0, 28.9, 23.9; IR (film) ν$_{max}$ 2930, 2856, 1699, 1501, 1470, 1425, 1283, 1119, 991, 962, 785 cm$^{-1}$; ESI-TOF m/z 336.1703 (C$_{20}$H$_{21}$N$_3$O$_2$+H$^+$ requires 336.1706).

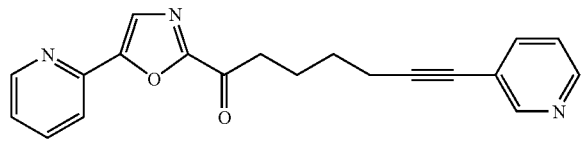

1-Oxo-1-[5-(2-pyridyl)oxazol-2-yl]-7-(3-pyridyl)hept-6-yne (4f). The title compound was prepared from 1-oxo-1-[5-(2-pyridyl)oxazol-2-yl]-7-(trimethylsilyl)hept-6-yne (3a (Boger, D. L.; Miyauchi, H.; et al. *J. Med. Chem.* 2005, 48, 1849-1856)) and 3-iodopyridine following general procedure E. PTLC (SiO$_2$, 50% EtOAc-hexanes +1% Et$_3$N) afforded 4f (20 mg, 0.06 mmol, 50%) as a pale yellow solid: $^1$H NMR (CDCl$_3$, 400 MHz) δ 8.66 (app d, 1H, J=4.7 Hz), 8.62 (br s, 1H), 8.48 (br s, 1H), 7.87-7.85 (m, 2H), 7.81 (td, 1H, J=7.6, 1.5 Hz), 7.66 (d, 1H, J=7.9 Hz), 7.33-7.30 (m, 1H), 7.20 (dd, 1H, J=7.8, 4.9 Hz), 3.19 (t, 2H, J=7.3 Hz), 2.51 (t, 2H, J=7.0 Hz), 2.00-1.93 (m, 2H), 1.78-1.70 (m, 2H); $^{13}$C NMR (CDCl$_3$, 100 MHz) δ 187.9, 157.2, 153.3, 152.2, 150.1, 147.9, 146.2, 138.5, 137.1, 126.8, 124.1, 122.9, 120.9, 120.4, 93.2, 77.8, 38.4, 27.8, 23.1, 19.2; IR (film) ν$_{max}$ 2932, 2233, 1699, 1602, 1573, 1503, 1469, 1425, 1407, 1386, 1283, 1119, 1083, 1023, 989, 962, 785, 707 cm$^{-1}$; ESI-TOF m/z 332.1403 (C$_{20}$H$_{17}$N$_3$O$_2$+H$^+$ requires 332.1393).

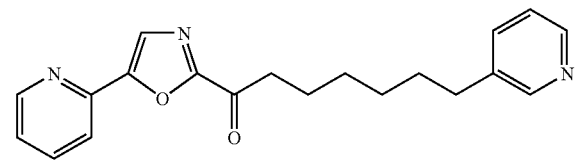

1-Oxo-1-[5-(2-pyridyl)oxazol-2-yl]-7-(3-pyridyl)heptane (5f). The title compound was prepared from 1-oxo-1-[5-(2-pyridyl)oxazol-2-yl]-7-(3-pyridyl)hept-6-yne (4f) following general procedure F. PTLC (SiO$_2$, 50% EtOAc-hexanes) afforded 5f (9.5 mg, 0.021 mmol, 95%) as a white solid: $^1$H NMR (CDCl$_3$, 500 MHz) δ 8.67-8.65 (m, 1H), 8.45-8.42 (m, 1H), 7.88-7.83 (m, 2H), 7.81 (td, 1H, J=7.7, 1.8 Hz), 7.50 (d, 1H, J=7.7 Hz), 7.33-7.30 (m, 1H), 7.21 (dd, 1H, J=7.7, 4.8 Hz), 3.11 (t, 2H, J=7.3 Hz), 2.62 (t, 2H, J=7.7 Hz), 1.81-1.75 (m, 2H), 1.68-1.62 (m, 2H), 1.47-1.37 (m, 4H); $^{13}$C NMR (CDCl$_3$, 125 MHz) δ 188.4, 157.3, 153.3, 150.1, 149.6, 147.0, 146.2, 137.8, 137.1, 136.0, 126.8, 124.1, 123.3, 120.4, 39.0, 32.9, 30.9, 28.8 (2C), 23.8; IR (film) ν$_{max}$ 2929, 2856, 1698, 1602, 1575, 1503, 1469, 1425, 1382, 1283, 1119, 1027, 990, 963, 785, 713 cm$^{-1}$; ESI-TOF m/z 336.1706 (C$_{20}$H$_{21}$N$_3$O$_2$+H$^+$ requires 336.1706).

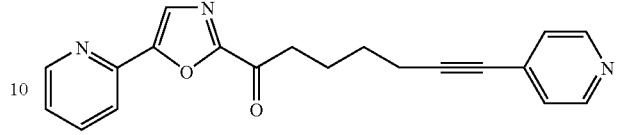

1-Oxo-1-[5-(2-pyridyl)oxazol-2-yl]-7-(4-pyridyl)hept-6-yne (4pp). The title compound was prepared from 1-oxo-1-[5-(2-pyridyl)oxazol-2-yl]-7-hept-6-yne (3b (Boger, D. L.; Miyauchi, H.; et al. *J. Med. Chem.* 2005, 48, 1849-1856)) and 4-iodopyridine following general procedure D. PTLC (SiO$_2$, 50% EtOAc-hexanes +1% Et$_3$N) afforded 4pp (31 mg, 0.09 mmol, 79%) as a yellow solid: $^1$H NMR (CDCl$_3$, 400 MHz) δ 8.68-8.66 (m, 1H), 8.54 (br s, 2H), 7.88-7.85 (m, 2H), 7.81 (td, 1H, J=7.9, 1.8 Hz), 7.34-7.30 (m, 1H), 7.25 (d, 2H, J=3.8 Hz), 3.19 (t, 2H, J=7.3 Hz), 2.51 (t, 2H, J=7.0 Hz), 2.00-1.92 (m, 2H), 1.78-1.71 (m, 2H); $^{13}$C NMR (CDCl$_3$, 100 MHz) δ 187.8, 157.2, 153.3, 150.1, 149.5, 146.1, 137.1, 132.0, 128.4, 126.8, 126.0, 124.1, 120.3, 95.0, 78.8, 38.4, 27.6, 23.0, 19.2; IR (film) ν$_{max}$ 2939, 2231, 1699, 1593, 1505, 1470, 1425, 1283, 1239, 1214, 1152, 1118, 1082, 1024, 990, 962, 824, 786, 695 cm$^{-1}$; ESI-TOF m/z 332.1396 (C$_{20}$H$_{17}$N$_3$O$_2$+H$^+$ requires 332.1393).

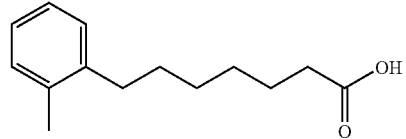

7-(o-Tolyl)heptanoic acid (S6). The title compound was prepared from o-tolualdehyde and BrPh$_3$P(CH$_2$)$_5$CO$_2$H (S1) following general procedure A. No further purification was required to yield S6 (365 mg, 1.66 mmol, 45%, 2 steps) as a tan oil: $^1$H NMR (CDCl$_3$, 400 MHz) δ 7.13-7.11 (m, 4H), 2.60 (t, 2H, J=7.6 Hz), 2.37 (t, 2H, J=7.4 Hz), 2.32 (s, 3H), 1.68-1.57 (m, 4H), 1.43-1.40 (m, 4H); $^{13}$C NMR (CDCl$_3$, 125 MHz) δ 180.0, 140.8, 135.8, 130.1, 128.7, 125.8, 125.7, 34.0, 33.2, 30.0, 29.2, 28.9, 24.6, 19.3.

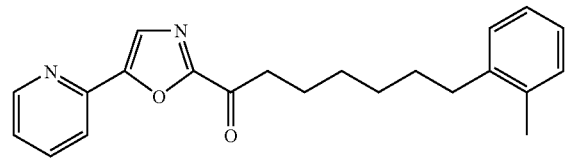

1-Oxo-1-[5-(2-pyridyl)oxazol-2-yl]-7-(o-tolyl)heptane (5g). The title compound was prepared from 5-(2-pyridyl)oxazole (6) and 7-(o-tolyl)heptanoic acid (S6) using general procedure B. Column chromatography (SiO$_2$, 2.5×6.5 cm, 20% EtOAc-hexanes) followed by PTLC (SiO$_2$, 50% EtOAc-hexanes) afforded 5g (65 mg, 0.19 mmol, 39%) as a white solid: $^1$H NMR (CDCl$_3$, 500 MHz) δ 8.68 (app d, 1H, J=4.8 Hz), 7.89-7.87 (m, 2H), 7.82 (td, 1H, J=7.7, 1.5 Hz), 7.34-7.31 (m, 1H), 7.14-7.08 (m, 4H), 3.13 (t, 2H, J=7.3 Hz), 2.60 (t, 2H, J=7.7 Hz), 2.31 (s, 3H), 1.84-1.78 (m, 2H), 1.63-1.57 (m, 2H), 1.47-1.44 (m, 4H); $^{13}$C NMR (CDCl$_3$, 125 MHz) δ 188.4, 157.5, 153.2, 150.0, 146.2, 137.0, 135.7, 130.0, 128.7, 126.8, 125.8, 125.6, 124.0, 120.3, 39.0, 34.9, 33.1, 30.0, 29.3, 29.0, 23.9, 19.2; IR (film) ν$_{max}$ 2931, 2857, 1699, 1602, 1575, 1558, 1505, 1470, 1426, 1381, 1237, 1151, 1118, 1082, 1033, 990, 963, 936, 851, 785, 741 cm$^{-1}$; ESI-TOF m/z 349.1926 (C$_{22}$H$_{24}$N$_2$O$_3$+H$^+$ requires 349.1916).

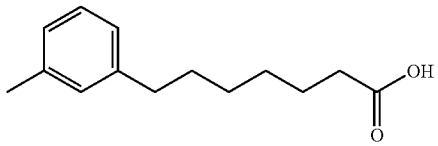

7-(m-Tolyl)heptanoic acid (S7). The title compound was prepared from m-tolualdehyde and BrPh$_3$P(CH$_2$)$_5$CO$_2$H (S1) following general procedure A. No further purification was required to yield S7 (315 mg, 1.43 mmol, 37%, 2 steps) as a colorless oil: $^1$H NMR (CDCl$_3$, 400 MHz) δ 7.17 (t, 1H, J=3.8 Hz), 7.01-6.99 (m, 3H), 2.58 (t, 2H, J=7.6 Hz), 2.38 (t, 2H, J=7.4 Hz), 2.35 (s, 3H), 1.70-1.59 (m, 4H), 1.40-1.36 (m, 4H); $^{13}$C NMR (CDCl$_3$, 100 MHz) δ 180.1, 142.6, 137.6, 129.2, 128.1, 126.3, 125.4, 35.8, 34.1, 31.3, 28.9, 24.6, 21.4.

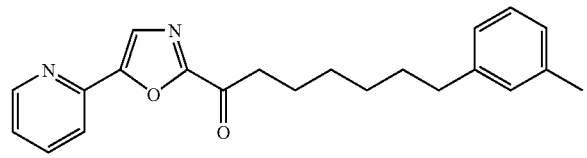

1-Oxo-1-[5-(2-pyridyl)oxazol-2-yl]-7-(m-tolyl)heptane (5h). The title compound was prepared from 5-(2-pyridyl)oxazole (6) and 7-(m-tolyl)heptanoic acid (S7) using general procedure B. Column chromatography (SiO$_2$, 2.5×4.5 cm, 20% EtOAc-hexanes) followed by PTLC (SiO$_2$, 50% EtOAc-hexanes) afforded 5h (60 mg, 0.17 mmol, 36%) as a white solid: $^1$H NMR (CDCl$_3$, 500 MHz) δ 8.68 (app d, 1H, J=4.4 Hz), 7.89-7.87 (m, 2H), 7.82 (td, 1H, J=7.7, 1.5 Hz), 7.34-7.31 (m, 1H), 7.17 (t, 1H, J=7.4 Hz), 7.00-6.96 (m, 3H), 3.12 (t, 2H, J=7.3 Hz), 2.59 (t, 2H, J=7.7 Hz), 2.33 (s, 3H), 1.84-1.76 (m, 2H), 1.67-1.61 (m, 2H), 1.47-1.37 (m, 4H); $^{13}$C NMR (CDCl$_3$, 100 MHz) δ 188.4, 157.7, 153.1, 150.0, 146.2, 142.5, 137.6, 137.0, 129.1, 128.0, 126.8, 126.2, 125.3, 124.0, 120.3, 39.0, 35.7, 31.2, 28.9 (2C), 23.8, 21.3; IR (film) ν$_{max}$ 2930, 2856, 1700, 1605, 1575, 1505, 1470, 1426, 1382, 1283, 1151, 1118, 1082, 1037, 990, 963, 936, 851, 784, 740, 700 cm$^{-1}$; ESI-TOF m/z 349.1910 (C$_{22}$H$_{24}$N$_2$O$_3$+H$^+$ requires 349.1916).

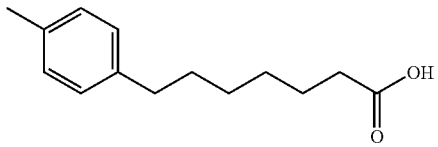

7-(p-Tolyl)heptanoic acid (S8). The title compound was prepared from p-tolualdehyde and BrPh$_3$P(CH$_2$)$_5$CO$_2$H (S1) following general procedure A. No further purification was required to yield S8 (285 mg, 1.30 mmol, 32%, 2 steps) as a white solid: $^1$H NMR (CDCl$_3$, 400 MHz) δ 7.11-7.06 (m, 4H), 2.58 (t, 2H, J=7.6 Hz), 2.37 (t, 2H, J=7.4 Hz), 2.34 (s, 3H), 1.68-1.60 (m, 4H), 1.39-1.36 (m, 4H); $^{13}$C NMR (CDCl$_3$, 125 MHz) δ 179.8, 139.5, 135.0, 128.9, 128.2, 35.4, 33.9, 31.4, 28.9, 28.8, 24.6, 21.0.

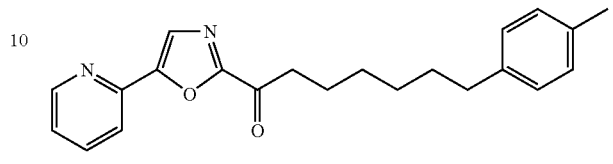

1-Oxo-1-[5-(2-pyridyl)oxazol-2-yl]-7-(p-tolyl)heptane (5i). The title compound was prepared from 5-(2-pyridyl)oxazole (6) and 7-(p-tolyl)heptanoic acid (S8) using general procedure B. Column chromatography (SiO$_2$, 2.5×5 cm, 20% EtOAc-hexanes) followed by PTLC (SiO$_2$, 50% EtOAc-hexanes) afforded 5i (58 mg, 0.17 mmol, 35%) as a white solid: $^1$H NMR (CDCl$_3$, 400 MHz) δ 8.68 (m, 1H), 7.89-7.85 (m, 2H), 7.82 (t, 1H, J=7.4 Hz), 7.34-7.31 (m, 1H), 7.06 (s, 4H), 3.11 (t, 2H, J=7.3 Hz), 2.58 (t, 2H, J=7.3 Hz), 2.32 (s, 3H), 1.83-1.75 (m, 2H), 1.67-1.61 (m, 2H), 1.46-1.37 (m, 4H); $^{13}$C NMR (CDCl$_3$, 100 MHz) δ 188.5, 157.3, 150.1, 146.3, 139.5, 137.6, 137.1, 135.0, 128.9, 128.2, 126.8, 124.1, 120.4, 39.1, 35.4, 31.4, 28.9 (2C), 23.9, 21.0; IR (film) ν$_{max}$ 2921, 2849, 1698, 1604, 1575, 1558, 1515, 1471, 1427, 1404, 1386, 1260, 1235, 1129, 1094, 1078, 1035, 990, 961, 933, 809, 784, 742 cm$^{-1}$; ESI-TOF m/z 349.1912 (C$_{22}$H$_{24}$N$_2$O$_3$+H$^+$ requires 349.1916).

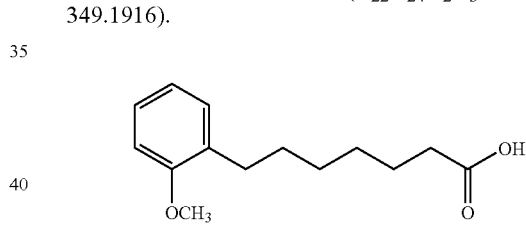

7-(2-Methoxyphenyl)heptanoic acid (S10). The title compound was prepared from o-anisaldehyde and BrPh$_3$P(CH$_2$)$_5$CO$_2$H (S1) following general procedure A. No further purification was needed to afford S10 (370 mg, 1.30 mmol, 59%, 2 steps) as a white solid: $^1$H NMR (CDCl$_3$, 400 MHz) δ 7.20-7.13 (m, 2H), 6.91-6.85 (m, 2H), 3.83 (s, 3H), 2.62 (t, 2H, J=7.4 Hz), 2.37 (t, 2H, J=7.6 Hz), 1.66-1.60 (m, 4H), 1.40-1.37 (m, 4H); $^{13}$C NMR (CDCl$_3$, 100 MHz) δ 180.4, 157.4, 131.0, 129.7, 126.8, 120.3, 110.2, 55.2, 34.1, 30.0, 29.5, 29.1, 28.9, 24.6.

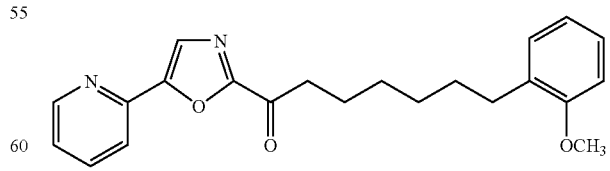

1-Oxo-1-[5-(2-pyridyl)oxazol-2-yl]-7-(2-methoxyphenyl) heptane (5j). The title compound was prepared from 5-(2-pyridyl)oxazole (6) and 7-(2-methoxyphenyl)heptanoic acid (S10) using general procedure B. Column chromatography (SiO$_2$, 2.5×6 cm, 15-25% EtOAc-hexanes gradient)

followed by PTLC (SiO$_2$, 50% EtOAc-hexanes) afforded 5j (65 mg, 0.18 mmol, 37%) as a pale yellow solid: $^1$H NMR (CDCl$_3$, 500 MHz) δ 8.67 (app d, 1H, J=4.4 Hz), 7.89-7.86 (m, 2H), 7.81 (td, 1H, J=7.4, 1.8 Hz), 7.34-7.30 (m, 1H), 7.19-7.11 (m, 2H), 6.88 (t, 1H, J=7.4 Hz), 6.84 (d, 1H, J=8.2 Hz), 3.82 (s, 3H), 3.12 (t, 2H, J=7.4 Hz), 2.61 (t, 2H, J=7.6 Hz), 1.83-1.75 (m, 2H), 1.64-1.56 (m, 2H), 1.49-1.40 (m, 4H); $^{13}$C NMR (100 MHz, CDCl$_3$) δ 188.5, 157.3, 153.1, 150.0, 146.2, 137.0, 131.0, 129.7, 126.8, 126.7, 124.0, 120.3, 120.2, 55.1, 39.1, 30.0, 29.5, 29.2, 28.9, 23.9; IR (film) $v_{max}$ 3053, 2931, 2856, 1699, 1601, 1575, 1494, 1455, 1427, 1382, 1288, 1242, 1177, 1151, 1119, 1082, 1049, 1029, 990, 963, 936, 851, 785, 753 cm$^{-1}$; ESI-TOF m/z 365.1877 (C$_{22}$H$_{24}$N$_2$O$_3$+H$^+$ requires 365.1865).

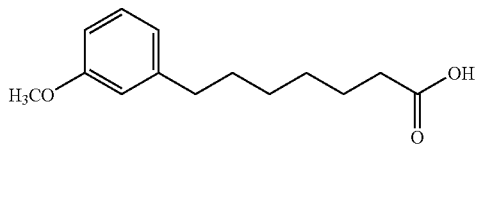

7-(3-Methoxyphenyl)heptanoic acid (S11). The title compound was prepared from m-anisaldehyde and BrPh$_3$P(CH$_2$)$_5$CO$_2$H (S1) following general procedure A. No further purification was needed to afford S11 (415 mg, 1.76 mmol, 67%, 2 steps) as a colorless oil: $^1$H NMR (CDCl$_3$, 500 MHz) δ 7.22-7.15 (m, 1H), 6.77 (d, 1H, J=7.6 Hz), 6.75-6.72 (m, 2H), 3.80 (s, 3H), 2.59 (t, 2H, J=7.7 Hz), 2.37 (t, 2H, J=7.4 Hz), 1.68-1.60 (m, 4H), 1.40-1.36 (m, 4H); $^{13}$C NMR (CDCl$_3$, 100 MHz) δ 180.5, 159.5, 144.3, 129.1, 120.8, 114.1, 110.8, 55.0, 35.8, 34.0, 31.1, 28.8 (2C), 24.5.

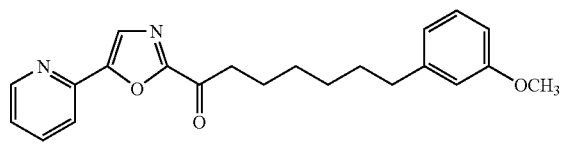

1-Oxo-1-[5-(2-pyridyl)oxazol-2-yl]-7-(3-methoxyphenyl)heptane (5k). The title compound was prepared from 5-(2-pyridyl)oxazole (6) and 7-(3-methoxyphenyl)heptanoic acid (S11) using procedure B. Column chromatography (SiO$_2$, 2×6 cm, 10-25% EtOAc-hexanes gradient) followed by PTLC (SiO$_2$, 50% EtOAc-hexanes) afforded 5k (80 mg, 0.22 mmol, 46%) as a white solid: $^1$H NMR (CDCl$_3$, 400 MHz) δ 8.67 (d, 1H, J=4.7 Hz), 7.89-7.86 (m, 2H), 7.82 (td, 1H, J=7.6, 1.6 Hz), 7.34-7.30 (m, 1H), 7.21-7.17 (m, 1H), 6.77 (d, 1H, J=7.6 Hz), 6.72-6.70 (m, 3H), 3.80 (s, 3H), 3.11 (t, 2H, J=7.4 Hz), 2.59 (t, 2H, J=7.6 Hz), 1.83-1.75 (m, 2H), 1.67-1.60 (m, 2H), 1.47-1.40 (m, 4H); $^{13}$C NMR (CDCl$_3$, 100 MHz) δ 188.5, 157.3, 153.1, 150.0, 146.2, 137.0, 131.0, 129.7, 126.8, 126.7, 124.0, 120.3, 120.2, 55.1, 39.1, 30.0, 29.5, 29.2, 28.9, 23.9; IR (film) $v_{max}$ 3052, 2932, 2855, 1699, 1601, 1505, 1471, 1455, 1427, 1283, 1259, 1152, 1118, 1082, 1045, 990, 963, 936, 851, 784, 740, 696 cm$^{-1}$; ESI-TOF m/z 365.1868 (C$_{22}$H$_{24}$N$_2$O$_3$+H$^+$ requires 365.1865).

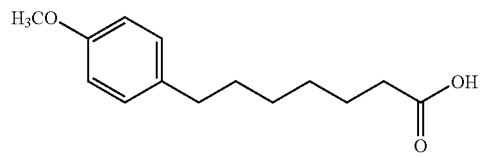

7-(4-Methoxyphenyl)heptanoic acid (S12). The title compound was prepared from p-anisaldehyde and BrPh$_3$P(CH$_2$)$_5$CO$_2$H (S1) following general procedure A. No further purification was required to yield S12 (471 mg, 2.0 mmol, 75%, 2 steps) as a white solid: $^1$H NMR (CDCl$_3$, 500 MHz) δ 7.09 (d, 2H, J=8.4 Hz), 6.83 (d, 2H, J=8.4 Hz), 3.80 (s, 3H), 2.56 (t, 2H, J=7.3 Hz), 2.36 (t, 2H, J=7.3 Hz), 1.68-1.58 (m, 4H), 1.39-1.36 (m, 4H); $^{13}$C NMR (CDCl$_3$, 100 MHz) δ 180.4, 157.5, 134.7, 129.2, 113.5, 55.0, 34.9, 34.0, 31.4, 28.8 (2C), 24.6.

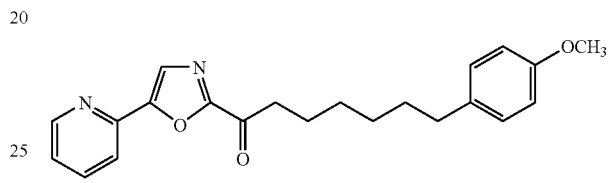

1-Oxo-1-[5-(2-pyridyl)oxazol-2-yl]-7-(4-methoxyphenyl)heptane (5l). The title compound was prepared from 5-(2-pyridyl)oxazole (6) and 7-(4-methoxyphenyl)heptanoic acid (S12) using general procedure B. Column chromatography (SiO$_2$, 2×6 cm, 10-25% EtOAc-hexanes gradient) followed by PTLC (SiO$_2$, 50% EtOAc-hexanes) afforded 5l (55 mg, 0.15 mmol, 32%) as a white solid: $^1$H NMR (CDCl$_3$, 400 MHz) δ 8.67 (app d, 1H, J=4.1 Hz), 7.88-7.86 (m, 2H), 7.81 (td, 1H, J=7.4, 1.8 Hz), 7.34-7.30 (m, 1H), 7.08 (d, 2H, J=8.5 Hz), 6.81 (d, 2H, J=8.7 Hz), 3.78 (s, 3H), 3.11 (t, 2H, J=7.4 Hz), 2.59 (t, 2H, J=7.4 Hz), 1.82-1.75 (m, 2H), 1.64-1.57 (m, 2H), 1.44-1.37 (m, 4H); $^{13}$C NMR (CDCl$_3$, 100 MHz) δ 188.4, 157.5, 157.3, 153.2, 150.1, 146.2, 137.1, 134.7, 129.2, 126.8, 124.1, 120.3, 113.6, 55.2, 39.0, 34.9, 31.4, 28.9, 28.8, 23.9; IR (film) $v_{max}$ 2926, 2851, 1696, 1652, 1506, 1470, 1456, 1428, 1236, 1035, 984, 961, 927 cm$^{-1}$; ESI-TOF m/z 365.1852 (C$_{22}$H$_{24}$N$_2$O$_3$+H$^+$ requires 365.1865).

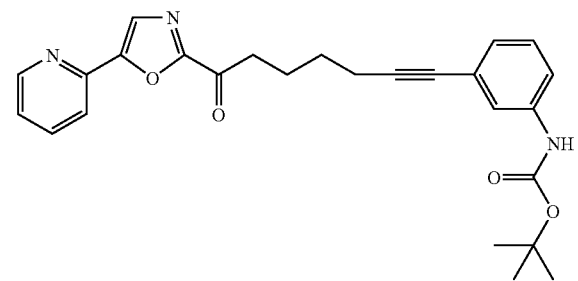

1-Oxo-1-[5-(2-pyridyl)oxazol-2-yl]-7-(3-(tert-butyloxycarbonyl)aminophenyl)hept-6-yne (4o). The title compound was prepared from 1-oxo-1-[5-(2-pyridyl)oxazol-2-yl]-hept-6-yne (3b (Boger, D. L.; Miyauchi, H.; et al. *J. Med. Chem.* 2005, 48, 1849-1856)) and iodo-3-(tert-butyloxycarbonyl)aminobenzene following general procedure E. Column chromatography (SiO$_2$, 2.5×3.5 cm, 25-50% EtOAc-hexanes gradient) afforded 4o (28 mg, 0.063 mmol, 40%) as a yellow oil: ¹H NMR (CDCl₃, 600 MHz) δ 8.67 (app d, 1H, J=4.8 Hz), 7.89 (s, 1H), 7.87 (d, 1H, J=7.9 Hz), 7.82 (td, 1H, J=7.8, 1.8 Hz), 7.39 (br s, 1H), 7.33-7.29 (m, 2H), 7.18 (t, 1H, J=7.9 Hz), 7.06 (d, 1H, J=7.4 Hz), 6.48 (br s, 1H), 3.19 (t, 2H, J=7.3 Hz), 2.47 (t, 2H, J=7.0 Hz), 1.99-1.94 (m, 2H), 1.75-1.70 (m, 2H), 1.51 (s, 9H); ¹³C NMR (CDCl₃, 150 MHz) δ 188.0, 163.1, 157.3, 153.2, 152.6, 150.1, 146.2, 138.2, 137.1, 128.8, 126.8, 126.2, 124.5, 124.1, 121.3, 120.4, 117.8, 89.6, 80.8, 38.5, 29.6, 28.3, 28.0, 23.1, 19.1; IR (film) ν$_{max}$ 3344, 3054, 2930, 2230, 1731, 1698, 1605, 1584, 1538, 1470, 1427, 1367, 1276, 1236, 1160, 1050, 991, 962, 851, 785, 740, 690 cm⁻¹.

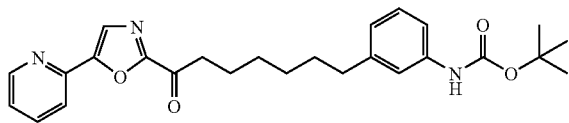

1-Oxo-1-[5-(2-Pyridyl)oxazol-2-yl]-7-(3-(tert-butyloxycarbonyl)aminophenyl)-heptane (5o). The title compound was prepared from 1-oxo-1-[5-(2-pyridyl)oxazol-2-yl]-7-(3-(tert-butyloxycarbonyl)aminophenyl)hept-6-yne (4o) following procedure I. PTLC (SiO₂, 50% EtOAc-hexanes) afforded 5o (9 mg, 0.020 mmol, 55%) as a white solid: ¹H NMR (CDCl₃, 500 MHz) δ 8.68 (app d, 1H, J=4.0 Hz), 7.89-7.87 (m, 2H), 7.82 (td, 1H, J=7.5, 1.7 Hz), 7.34-7.31 (m, 1H), 7.23 (br s, 1H), 7.18 (t, 1H, J=7.9 Hz), 7.14-7.12 (m, 1H), 6.85 (d, 1H, J=7.3 Hz), 6.48 (br s, 1H), 3.11 (t, 2H, J=7.3 Hz), 2.58 (t, 2H, J=7.7 Hz), 1.81-1.75 (m, 2H), 1.66-1.59 (m, 2H), 1.52 (s, 9H), 1.45-1.35 (m, 4H).

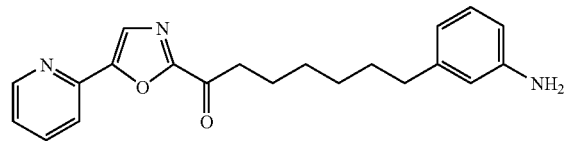

1-Oxo-1-[5-(2-pyridyl)oxazol-2-yl]-7-(3-aminophenyl)heptane (5m). The title compound was prepared from 1-oxo-1-[5-(2-pyridyl)oxazol-2-yl]-7-(3-(tert-butyloxycarbonyl) aminophenyl)heptane (5o) following procedure J. PTLC (SiO₂, pretreated with 1% Et₃N-hexanes, 20% EtOAc-hexanes) afforded 5m (2 mg, 0.0057 mmol, 67%) as a tan film: ¹H NMR (CDCl₃, 400 MHz) δ 8.77 (m, 1H), 7.99-7.95 (m, 3H), 7.48-7.45 (m, 1H), 7.26-7.12 (m, 4H), 3.08 (t, 2H, J=7.3 Hz), 2.58 (t, 2H, J=7.3 Hz), 1.79-1.72 (m, 2H), 1.63-1.56 (m, 2H), 1.40-1.28 (m, 4H); ESI-TOF m/z 350.1865 (C₂₁H₂₃N₃O₂+H⁺ requires 350.1863).

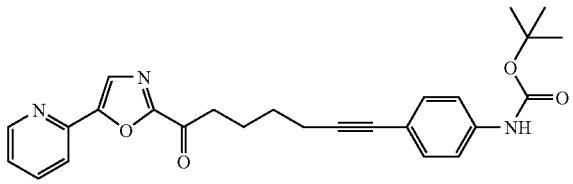

1-Oxo-1-[5-(2-pyridyl)oxazol-2-yl]-7-(4-(tert-butyloxycarbonyl)aminophenyl)hept-6-yne (4p). The title compound was prepared from 1-oxo-1-[5-(2-pyridyl)oxazol-2-yl]-hept-6-yne (3b (Boger, D. L.; Miyauchi, H.; et al. *J. Med. Chem.* 2005, 48, 1849-1856)) and iodo-(4-tert-butyloxycarbonyl)aminobenzene following general procedure E. Column chromatography (SiO₂, 3×5 cm, 10-40% EtOAc-hexanes gradient) afforded 4p (70 mg, 0.157 mmol, 67%) as a yellow solid: ¹H NMR (CDCl₃, 500 MHz) δ 8.67 (d, 1H, J=4.4 Hz), 7.88 (s, 1H), 7.85 (d, 1H, J=7.7 Hz), 7.81 (td, 1H, J=7.7, 1.8 Hz), 7.33-7.26 (m, 5H), 6.55 (s, 1H), 3.19 (t, 2H, J=7.5 Hz), 2.47 (t, 2H, J=7.0 Hz), 2.00-1.97 (m, 2H), 1.95-1.93 (m, 2H), 1.51 (s, 9H); ¹³C NMR (CDCl₃, 125 MHz) δ 188.0, 157.2, 153.2, 152.4, 150.0, 146.1, 137.8, 137.1, 132.2, 126.8, 124.1, 120.3, 118.1, 117.9, 88.5, 80.7, 80.6, 38.5, 28.2, 28.0, 23.1, 19.1; IR (film) ν$_{max}$ 3332, 2932, 2271, 1732, 1699, 1588, 1520, 1505, 1471, 1456, 1427, 1367, 1312, 1232, 1159, 1052, 1027, 838, 784, 738 cm⁻¹; ESI-TOF m/z 446.2073 (C₂₆H₂₇N₃O₄+H⁺ requires 446.2074).

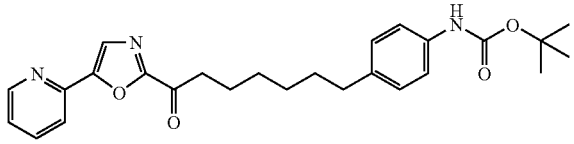

1-Oxo-1-[5-(2-pyridyl)oxazol-2-yl]-7-(4-(tert-butyloxycarbonyl)aminophenyl)-heptane (5p). The title compound was prepared from 1-oxo-1-[5-(2-pyridyl)oxazol-2-yl]-7-(4-(tert-butyloxycarbonyl)aminophenyl)hept-6-yne (4p) following general procedure I. Column chromatography (SiO₂, 2.5×4.5 cm, 20-40% EtOAc-hexanes gradient) afforded 5p (49 mg, 0.109 mmol, 87%) as a pale yellow solid: ¹H NMR (CDCl₃, 500 MHz) δ 8.67 (app d, 1H, J=4.8 Hz), 7.89-7.86 (m, 2H), 7.82 (t, 1H, J=7.7 Hz), 7.34-7.31 (m, 1H), 7.25 (d, 2H, J=8.4 Hz), 7.09 (d, 2H, J=8.4 Hz), 6.45 (s, 1H), 3.11 (t, 2H, J=7.7 Hz), 2.55 (t, 2H, J=7.7 Hz), 1.81-1.75 (m, 2H), 1.63-1.57 (m, 2H), 1.51 (s, 9H), 1.43-1.37 (m, 4H); ¹³C NMR (CDCl₃, 125 MHz) δ 188.5, 157.3, 153.1, 152.9, 150.0, 146.2, 137.4, 137.2, 135.9, 128.8, 126.9, 124.1, 120.4, 118.6, 80.2, 39.0, 35.1, 31.3, 28.9, 28.8, 28.3, 23.9; IR (film) ν$_{max}$ 3343, 2931, 2856, 2252, 1732, 1694, 1593, 1470, 1427, 1366, 1311, 1237, 1159, 1051, 991, 963, 910, 836, 784, 727 cm⁻¹; ESI-TOF m/z 472.2205 (C₂₆H₃₁N₃O₄+Na⁺ requires 472.2207).

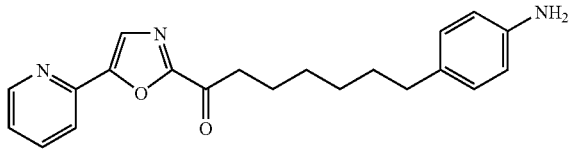

1-Oxo-1-[5-(2-pyridyl)oxazol-2-yl]-7-(4-aminophenyl)heptane (5n). The title compound was prepared from 1-oxo-1-[5-(2-pyridyl)oxazol-2-yl]-7-(4-(tert-butyloxycarbonyl) aminophenyl)heptane (5p) following general procedure J. Chromatography (SiO₂ pretreated with 1% Et₃N-hexanes, 20% EtOAc-hexanes) afforded 5n (10 mg, 0.029 mmol, 66%) as a tan solid: ¹H NMR (CDCl₃, 400 MHz) δ 8.67 (app d, 1H, J=3.8 Hz), 7.89-7.86 (m, 2H), 7.82 (t, 1H, J=7.6 Hz), 7.34-7.31 (m, 3H), 6.97 (d, 2H, J=7.9 Hz), 6.65 (d, 2H, J=7.7 Hz), 3.11 (t, 2H, J=7.3 Hz), 2.51 (t, 2H, J=7.6 Hz), 1.80-1.75 (m, 2H), 1.61-1.56 (m, 2H), 1.43-1.36 (m, 4H); ¹³C NMR (CDCl₃, 150 MHz) δ 188.5, 157.4, 153.2, 150.1, 149.9, 146.3, 137.1, 136.9, 129.2, 126.8, 124.1, 120.4, 39.1, 35.0, 31.5, 29.7, 28.9, 23.9; IR (film) ν$_{max}$ 3372, 3053, 2930, 2856, 1699, 1615, 1576, 1516, 1471, 1426, 1373, 1265, 1194, 1152, 1122, 964, 785, 741 cm$^{-1}$; ESI-TOF m/z 350.1871 ($C_{21}H_{23}N_3O_2$+H$^+$ requires 350.1863).

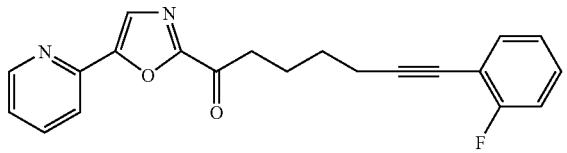

1-Oxo-1-[5-(2-pyridyl)oxazol-2-yl]-7-(2-fluorophenyl)hept-6-yne (4q). The title compound was prepared from 1-oxo-1-[5-(2-pyridyl)oxazol-2-yl]-7-(trimethylsilyl)hept-6-yne (3a (Boger, D. L.; Miyauchi, H.; et al. *J. Med. Chem.* 2005, 48, 1849-1856)) and 1-fluoro-2-iodobenzene following general procedure D. PTLC (SiO$_2$, 50% EtOAc-hexanes) afforded 4q (20 mg, 0.057 mmol, 38%) as a yellow oil: $^1$H NMR (CDCl$_3$, 400 MHz) δ 8.68-8.66 (m, 1H), 7.88-7.85 (m, 2H), 7.81 (td, 1H, J=7.7, 1.8 Hz), 7.38 (t, 1H, J=7.0 Hz), 7.33-7.30 (m, 1H), 7.26-7.20 (m, 1H), 7.06-7.00 (m, 2H), 3.20 (t, 2H, J=7.4 Hz), 2.53 (t, 2H, J=7.0 Hz), 2.02-1.95 (m, 2H), 1.79-1.72 (m, 2H); $^{13}$C NMR (CDCl$_3$, 100 MHz) δ 188.0, 162.7 (d, J=248.7 Hz), 157.3, 153.3, 150.1, 146.2, 137.1, 133.5, 129.1 (d, J=7.6 Hz), 126.8, 124.1, 123.7 (d, J=3.0 Hz), 120.4, 115.2 (d, J=21.2 Hz), 112.2 (d, J=16.7 Hz), 94.9 (d, J=4.6 Hz), 74.4, 38.5, 27.9, 23.0, 19.4; IR (film) ν$_{max}$ 2931, 2233, 1705, 1603, 1575, 1558, 1505, 1492, 1471, 1455, 1425, 1385, 1255, 1214, 1104, 1024, 785, 759 cm$^{-1}$; ESI-TOF m/z 349.1343 ($C_{21}H_{17}FN_2O_4$+H$^+$ requires 349.1347).

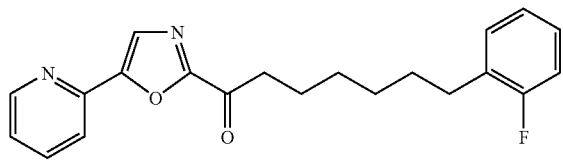

1-Oxo-1-[5-(2-pyridyl)oxazol-2-yl]-7-(2-fluorophenyl)heptane (5q). The title compound was prepared from 1-oxo-1-[5-(2-pyridyl)oxazol-2-yl]-7-(2-fluorophenyl)hept-6-yne (4q) following general procedure F. No further purification was required to yield 5q (9 mg, 0.025 mmol, 90%) as a pale yellow solid: $^1$H NMR (CDCl$_3$, 500 MHz) δ 8.69-8.66 (m, 1H), 7.89-7.86 (m, 2H), 7.82 (td, 1H, J=7.7, 1.8 Hz), 7.34-7.31 (m, 1H), 7.19-7.13 (m, 2H), 7.05 (td, 1H, J=7.5, 1.2 Hz), 7.01-6.97 (m, 1H), 3.12 (t, 2H, J=7.4 Hz), 2.65 (t, 2H, J=7.7 Hz), 1.82-1.76 (m, 2H), 1.67-1.60 (m, 2H), 1.49-1.38 (m, 4H); $^{13}$C NMR (CDCl$_3$, 150 MHz) δ 188.5, 161.1 (d, J=242.7 Hz), 157.4, 153.2, 150.1, 146.3, 137.1, 130.6 (d, J=5.7 Hz), 129.4 (d, J=16.0 Hz), 127.3 (d, J=32.0 Hz), 126.8, 124.1, 123.8 (d, J=3.4 Hz), 120.4, 115.1 (d, J=21.8 Hz), 39.1, 29.9, 29.0, 28.9, 28.8, 23.9; IR (film) ν$_{max}$ 2930, 2858, 1699, 1652, 1602, 1575, 1558, 1506, 1490, 1470, 1456, 1425, 1385, 1282, 1228, 1181, 1151, 1036 cm$^{-1}$; ESI-TOF m/z 353.1664 ($C_{21}H_{21}FN_2O_2$+H$^+$ requires 353.1665).

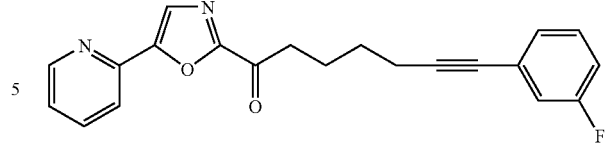

1-Oxo-1-[5-(2-pyridyl)oxazol-2-yl]-7-(3-fluorophenyl)hept-6-yne (4r). The title compound was prepared from 1-oxo-1-[5-(2-pyridyl)oxazol-2-yl]-7-(trimethylsilyl)hept-6-yne (3a (Boger, D. L.; Miyauchi, H.; et al. *J. Med. Chem.* 2005, 48, 1849-1856)) and 1-fluoro-3-iodobenzene following general procedure D. PTLC (SiO$_2$, 50% EtOAc-hexanes) afforded 4r (22 mg, 0.063 mmol, 52%) as a yellow solid: $^1$H NMR (CDCl$_3$, 500 MHz) δ 8.68-8.66 (m, 1H), 7.88-7.86 (m, 2H), 7.81 (td, 1H, J=7.8, 1.8 Hz), 7.34-7.31 (m, 1H), 7.25-7.20 (m, 1H), 7.18-7.15 (m, 1H), 7.10-7.06 (m, 1H), 3.19 (t, 2H, J=7.3 Hz), 2.49 (t, 2H, J=7.0 Hz), 2.00-1.94 (m, 2H), 1.77-1.70 (m, 2H); $^{13}$C NMR (CDCl$_3$, 125 MHz) δ 188.0, 162.3 (d, J=244.2 Hz), 157.2, 153.3, 150.1, 146.2, 137.1, 129.6 (d, J=8.6 Hz), 127.4 (d, J=2.9 Hz), 126.8, 125.6 (d, J=9.6 Hz), 124.1, 120.4, 118.3 (d, J=22.9 Hz), 114.8 (d, J=21.0 Hz), 90.6, 80.0, 38.5, 27.9, 23.1, 19.1; IR (film) ν$_{max}$ 2931, 2222, 1699, 1609, 1579, 1505, 1470, 1426, 1280, 1171, 1151, 1082, 1024, 870, 784 cm$^{-1}$; ESI-TOF m/z 349.1348 ($C_{21}H_{17}FN_2O_4$+H$^+$ requires 349.1347).

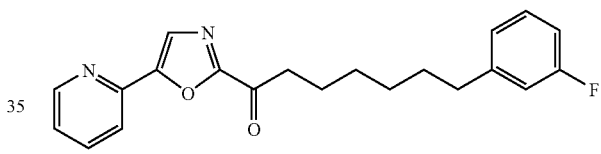

1-Oxo-1-[5-(2-pyridyl)oxazol-2-yl]-7-(3-fluorophenyl)heptane (5r). The title compound was prepared from 1-oxo-1-[5-(2-pyridyl)oxazol-2-yl]-7-(3-fluorophenyl)hept-6-yne (4r) following general procedure F. No further purification was required to yield 5r (9 mg, 0.025 mmol, 90%) as a yellow oil: $^1$H NMR (CDCl$_3$, 600 MHz) δ 8.68-8.66 (m, 1H), 7.89-7.86 (m, 2H), 7.82 (td, 1H, J=7.6, 1.8 Hz), 7.34-7.31 (m, 1H), 7.24-7.20 (m, 1H), 6.94 (d, 1H, J=7.9 Hz), 6.89-6.84 (m, 2H), 3.11 (t, 2H, J=7.6 Hz), 2.61 (t, 2H, J=7.9 Hz), 1.81-1.76 (m, 2H), 1.66-1.61 (m, 2H), 1.47-1.36 (m, 4H); $^{13}$C NMR (CDCl$_3$, 150 MHz) δ 188.4, 162.9 (d, J=243.8 Hz), 157.4, 153.3, 150.1, 146.3, 145.2 (d, J=6.9 Hz), 137.1, 129.5 (d, J=8.0 Hz), 126.8, 124.1, 120.0 (d, J=2.3 Hz), 115.1 (d, J=20.6 Hz), 112.4 (d, J=20.6 Hz), 39.0, 35.6, 30.9, 28.9, 28.8, 23.9; IR (film) ν$_{max}$ 2930, 2856, 1699, 1615, 1589, 1506, 1470, 1425, 1251, 1139, 1037, 962, 787, 742, 692 cm$^{-1}$; ESI-TOF m/z 353.1663 ($C_{21}H_{21}FN_2O_2$+H$^+$ requires 353.1665).

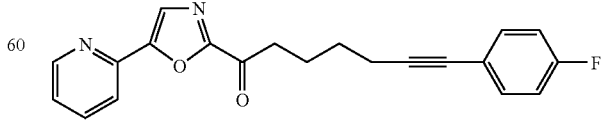

1-Oxo-1-[5-(2-pyridyl)oxazol-2-yl]-7-(4-fluorophenyl)hept-6-yne (4s). The title compound was prepared from 1-oxo-1-[5-(2-pyridyl)oxazol-2-yl]-7-(trimethylsilyl)

hept-6-yne (3a (Boger, D. L.; Miyauchi, H.; et al. *J. Med. Chem.* 2005, 48, 1849-1856)) and 1-fluoro-4-iodobenzene following general procedure D. PTLC (SiO$_2$, 50% EtOAc-hexanes) afforded 4s (16 mg, 0.046 mmol, 30%) as a pale yellow solid: $^1$H NMR (CDCl$_3$, 400 MHz) δ 8.68-8.66 (m, 1H), 7.88-7.85 (m, 2H), 7.81 (td, 1H, J=7.7, 1.8 Hz), 7.38-7.31 (m, 3H), 6.95 (t, 2H, J=8.8 Hz), 3.19 (t, 2H, J=7.3 Hz), 2.47 (t, 2H, J=7.0 Hz), 2.01-1.93 (m, 2H), 1.76-1.69 (m, 2H); $^{13}$C NMR (CDCl$_3$, 100 MHz) δ 188.0, 162.5 (d, J=247.2 Hz), 157.3, 153.3, 150.1, 146.2, 137.1, 133.3 (d, J=7.6 Hz), 126.8, 124.2, 120.4, 119.9, 115.3 (d, J=22.8 Hz), 89.1, 80.0, 38.5, 28.0, 23.1, 19.1; IR (film) ν$_{max}$ 2940, 2357, 1699, 1652, 1601, 1558, 1506, 1470, 1424, 1219, 1156, 1093, 838, 785 cm$^{-1}$; ESI-TOF m/z 349.1343 (C$_{21}$H$_{17}$FN$_2$O$_4$+H$^+$ requires 349.1347).

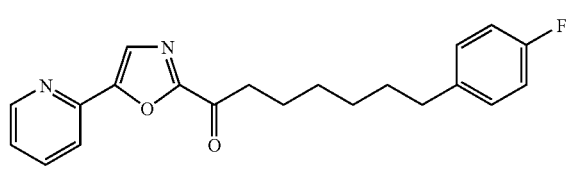

1-Oxo-1-[5-(2-pyridyl)oxazol-2-yl]-7-(4-fluorophenyl)heptane (5s). The title compound was prepared from 1-oxo-1-[5-(2-pyridyl)oxazol-2-yl]-7-(4-fluorophenyl)hept-6-yne (4s) following general procedure F. No further purification was required to yield 5s (9 mg, 0.025 mmol, 90%) as a white solid: $^1$H NMR (CDCl$_3$, 600 MHz) δ 8.68-8.66 (m, 1H), 7.89-7.86 (m, 2H), 7.82 (td, 1H, J=7.9, 1.8 Hz), 7.34-7.31 (m, 1H), 7.13-7.10 (m, 2H), 6.97-6.93 (m, 2H), 3.11 (t, 2H, J=7.4 Hz), 2.58 (t, 2H, J=7.9 Hz), 1.82-1.76 (m, 2H), 1.64-1.58 (m, 2H), 1.46-1.36 (m, 4H); $^{13}$C NMR (CDCl$_3$, 150 MHz) δ 188.4, 161.1 (d, J=246.0 Hz), 157.4, 153.2, 150.1, 146.3, 138.2 (d, J=2.3 Hz), 137.1, 129.6 (d, J=8.0 Hz), 126.8, 124.1, 120.4, 114.9 (d, J=20.6 Hz), 39.0, 35.0, 31.3, 28.9, 28.8, 23.9; IR (film) ν$_{max}$ 2924, 2855, 1703, 1601, 1510, 1463, 1422, 1216, 1160, 1117, 1079, 962, 934, 831, 790, 744, 694 cm$^{-1}$; ESI-TOF m/z 353.1662 (C$_{21}$H$_{21}$FN$_2$O$_2$+H$^+$ requires 353.1665).

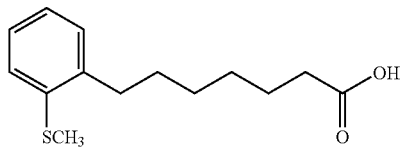

7-(2-(Methylthio)phenyl)heptanoic acid (S13). The title compound was prepared from 2-methylthiobenzaldehyde and BrPh$_3$P(CH$_2$)$_5$CO$_2$H (S1) following general procedure A. No further purification was required to yield S13 (600 mg, 2.40 mmol, 38%, 2 steps) as a white solid: $^1$H NMR (CDCl$_3$, 500 MHz) δ 7.20 (d, 2H, J=3.7 Hz), 7.15 (d, 1H, J=7.3 Hz), 7.12-7.08 (m, 1H), 2.71 (t, 2H, J=7.7 Hz), 2.47 (s, 3H), 2.37 (t, 2H, J=7.7 Hz), 1.68-1.63 (m, 4H), 1.43-1.40 (m, 4H); $^{13}$C NMR (CDCl$_3$, 125 MHz) δ 180.3, 140.3, 137.0, 128.9, 126.5, 125.3, 124.7, 34.0, 33.5, 29.6, 29.1, 28.8, 24.6, 15.6.

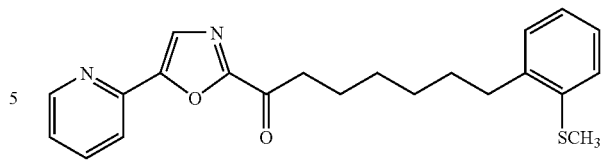

1-Oxo-1-[5-(2-pyridyl)oxazol-2-yl]-7-(2-(methylthio)phenyl)heptane (5t). The title compound was prepared from 5-(2-pyridyl)oxazole (6) and 7-(2-(methylthio)phenyl)heptanoic acid (S13) using general procedure B. Column chromatography (SiO$_2$, 2.5×6 cm, 20% EtOAc-hexanes) afforded 5t (240 mg, 0.66 mmol, 79%) as a yellow oil: $^1$H NMR (CDCl$_3$, 400 MHz) δ 8.69-8.66 (m, 1H), 7.89-7.86 (m, 2H), 7.81 (td, 1H, J=7.7, 1.8 Hz), 7.34-7.30 (m, 1H), 7.19 (d, 1H, J=3.3 Hz), 7.14 (d, 1H, J=7.3 Hz), 7.11-7.07 (m, 1H), 3.13 (t, 2H, J=7.3 Hz), 2.71 (t, 2H, J=7.9 Hz), 2.46 (s, 3H), 1.84-1.77 (m, 2H), 1.68-1.62 (m, 2H), 1.47-1.44 (m, 4H); $^{13}$C NMR (CDCl$_3$, 100 MHz) δ 188.5, 157.3, 153.2, 150.1, 146.2, 140.3, 137.1, 128.9, 126.8, 126.4, 125.2, 124.7, 124.1, 120.3, 39.1, 33.5, 29.6, 29.2, 28.9, 23.9, 15.6; IR (film) ν$_{max}$ 3055, 2926, 2856, 1704, 1602, 1557, 1505, 1471, 1427, 1385, 1283, 1119, 1045, 990, 963, 935, 850, 784, 742 cm$^{-1}$; ESI-TOF m/z 381.1631 (C$_{22}$H$_{24}$N$_2$O$_2$S+H$^+$ requires 381.1631).

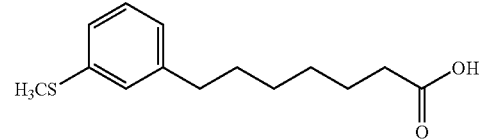

7-(3-(Methylthio)phenyl)heptanoic acid (S14). The title compound was prepared from 3-methylthiobenzaldehyde and BrPh$_3$P(CH$_2$)$_5$CO$_2$H (S1) following general procedure A. No further purification was required to yield S14 (300 mg, 1.19 mmol, 31%, 2 steps) as a yellow oil: $^1$H NMR (CDCl$_3$, 500 MHz) δ 7.23-7.19 (m, 1H), 7.10-7.08 (m, 2H), 6.96 (d, 1H, J=8.0 Hz), 2.59 (t, 2H, J=7.8 Hz), 2.49 (s, 3H), 2.37 (t, 2H, J=7.3 Hz), 1.69-1.60 (m, 4H), 1.40-1.37 (m, 4H); $^{13}$C NMR (CDCl$_3$, 125 MHz) δ 180.3, 143.3, 138.1, 128.7, 126.6, 125.3, 123.8, 35.8, 34.0, 31.1, 28.8 (2C), 24.5, 15.8.

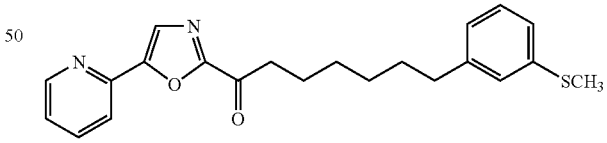

1-Oxo-1-[5-(2-pyridyl)oxazol-2-yl]-7-(3-(methylthio)phenyl)heptane (5u). The title compound was prepared from 5-(2-pyridyl)oxazole (6) and 7-(3-(methylthio)phenyl)heptanoic acid (S14) using general procedure B. Column chromatography (SiO$_2$, 2×5 cm, 10-20% EtOAc-hexanes gradient) afforded 5u (80 mg, 0.21 mmol, 56%) as a yellow oil: $^1$H NMR (CDCl$_3$, 500 MHz) δ 8.68-8.66 (m, 1H), 7.89-7.86 (m, 2H), 7.82 (td, 1H, J=7.8, 1.8 Hz), 7.33-7.30 (m, 1H), 7.20 (t, 1H, J=7.4 Hz), 7.08-7.06 (m, 2H), 6.95 (d, 1H, J=7.7 Hz), 3.11 (t, 2H, J=7.4 Hz), 2.58 (t, 2H, J=7.7 Hz), 2.48 (s, 3H), 1.82-1.76 (m, 2H), 1.66-1.60 (m, 2H), 1.47-1.36 (m, 4H); $^{13}$C NMR (CDCl$_3$, 125 MHz) δ 188.4, 157.3, 153.2, 150.1, 146.2, 143.2, 138.0, 137.0, 128.6, 126.8, 126.5, 125.2, 124.1, 123.8, 120.3, 39.0, 35.7, 31.1, 28.9, 28.8, 15.8, 16.4; IR (film) $v_{max}$ 2928, 2855, 1699, 1591, 1574, 1558, 1506, 1471, 1424, 1152, 1118, 1086, 990, 963, 936, 783, 741, 697 cm$^{-1}$; ESI-TOF m/z 381.1637 ($C_{22}H_{24}N_2O_2S+H^+$ requires 381.1631).

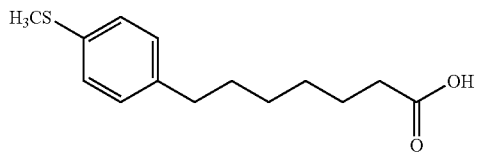

7-(4-(Methylthio)phenyl)heptanoic acid (S15). The title compound was prepared from 4-methylthiobenzaldehyde and BrPh$_3$P(CH$_2$)$_5$CO$_2$H (S1) following general procedure A. No further purification was required to yield S15 (400 mg, 1.59 mmol, 25%, 2 steps) as a white solid: $^1$H NMR (CDCl$_3$, 600 MHz) δ 7.21 (d, 2H, J=7.9 Hz), 7.11 (d, 2H, J=7.9 Hz), 2.58 (t, 2H, J=7.6 Hz), 2.48 (s, 3H), 2.37 (t, 2H, J=7.4 Hz), 1.68-1.58 (m, 4H), 1.39-1.35 (m, 4H); $^{13}$C NMR (CDCl$_3$, 100 MHz) δ 180.1, 139.8, 134.5, 128.9, 127.1, 35.2, 34.0, 31.2, 28.8 (2C), 24.5, 16.3.

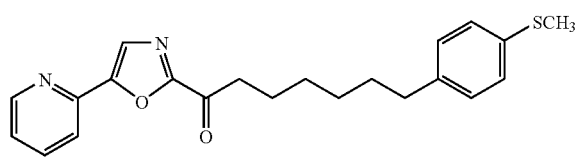

1-Oxo-1-[5-(2-pyridyl)oxazol-2-yl]-7-(4-(methylthio)phenyl)heptane (5v). The title compound was prepared from 5-(2-pyridyl)oxazole (6) and 7-(4-(methylthio)phenyl) heptanoic acid (S15) using general procedure B. Column chromatography (SiO$_2$, 3×8 cm, 20% EtOAc-hexanes) afforded 5v (195 mg, 0.51 mmol, 76%) as a yellow oil: $^1$H NMR (CDCl$_3$, 500 MHz) δ 8.68-8.66 (m, 1H), 7.88-7.85 (m, 2H), 7.81 (td, 1H, J=7.7, 1.8 Hz), 7.33-7.30 (m, 1H), 7.19 (d, 2H, J=8.1 Hz), 7.10 (d, 2H, J=8.1 Hz), 3.11 (t, 2H, J=7.3 Hz), 2.57 (t, 2H, J=7.7 Hz), 2.46 (s, 3H), 1.81-1.75 (m, 2H), 1.64-1.58 (m, 2H), 1.47-1.35 (m, 4H); $^{13}$C NMR (CDCl$_3$, 150 MHz) δ 188.4, 157.3, 153.2, 150.1, 146.3, 139.8, 137.1, 134.9, 128.9, 127.1, 124.1, 120.4, 39.0, 35.2, 31.2, 28.9, 28.8, 23.9, 16.4; IR (film) $v_{max}$ 3097, 2927, 2855, 1694, 1603, 1557, 1505, 1495, 1471, 1429, 1236, 1124, 1093, 962, 935, 786, 743, 697 cm$^{-1}$; ESI-TOF m/z 381.1635 ($C_{22}H_{24}N_2O_2S+H^+$ requires 381.1631).

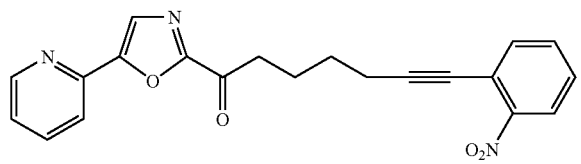

1-Oxo-1-[5-(2-pyridyl)oxazol-2-yl]-7-(2-nitrophenyl)hept-6-yne (4rr). The title compound was prepared from 1-oxo-1-[5-(2-pyridyl)oxazol-2-yl]-hept-6-yne (3b (Boger, D. L.; Miyauchi, H.; et al. *J. Med. Chem.* 2005, 48, 1849-1856)) and 1-iodo-2-nitrobenzene following general procedure E. PTLC (SiO$_2$, 50% EtOAc-hexanes) afforded 4rr (39 mg, 0.104 mmol, 59%) as a yellow solid: $^1$H NMR (CDCl$_3$, 600 MHz) δ 8.67-8.65 (m, 1H), 7.95 (d, 1H, J=7.7 Hz), 7.86 (s, 1H), 7.85 (d, 1H, J=7.4 Hz), 7.80 (td, 1H, J=7.8, 1.8 Hz), 7.58 (dd, 1H, J=7.8, 1.3 Hz), 7.51 (td, 1H, J=7.4, 1.3 Hz), 7.39 (td, 1H, J=7.4, 1.3 Hz) 7.33-7.30 (m, 1H), 3.20 (t, 2H, J=7.3 Hz), 2.56 (t, 2H, J=7.0 Hz), 2.02-1.97 (m, 2H), 1.80-1.74 (m, 2H); $^{13}$C NMR (CDCl$_3$, 150 MHz) δ 187.9, 157.3, 153.2, 150.1, 150.0, 146.2, 137.1, 134.8, 132.5, 127.9, 126.8, 124.3, 124.1, 120.4, 119.1, 98.4, 76.4, 38.5, 27.6, 23.0, 19.6; IR (film) $v_{max}$ 2931, 2231, 1705, 1607, 1568, 1520, 1505, 1470, 1425, 1343, 1287, 1152, 1084, 1023, 990, 963, 852, 785, 745, 694 cm$^{-1}$; ESI-TOF m/z 376.1298 ($C_{21}H_{17}N_3O_4+H^+$ requires 376.1292).

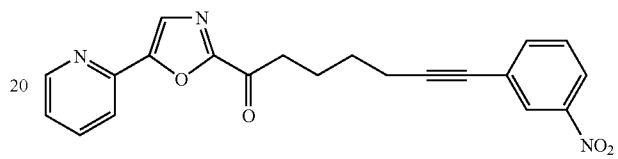

1-Oxo-1-[5-(2-pyridyl)oxazol-2-yl]-7-(3-nitrophenyl)hept-6-yne (4ss). The title compound was prepared from 1-oxo-1-[5-(2-pyridyl)oxazol-2-yl]-hept-6-yne (3b (Boger, D. L.; Miyauchi, H.; et al. *J. Med. Chem.* 2005, 48, 1849-1856)) and 1-iodo-3-nitrobenzene following general procedure E. PTLC (SiO$_2$, 50% EtOAc-hexanes) afforded 4ss (48 mg, 0.128 mmol, 71%) as a tan solid: $^1$H NMR (CDCl$_3$, 600 MHz) δ 8.67-8.65 (m, 1H), 8.22 (s, 1H), 8.11-8.09 (m, 1H), 7.88 (s, 1H), 7.86 (dd, 1H, J=7.8, 1.3 Hz), 7.83-7.80 (m, 1H), 7.68 (dd, 1H, J=7.8, 1.2 Hz), 7.44 (t, 1H, J=7.8 Hz), 7.34-7.31 (m, 1H), 3.21 (t, 2H, J=7.5 Hz), 2.52 (t, 2H, J=7.0 Hz), 2.01-1.96 (m, 2H), 1.78-1.73 (m, 2H); $^{13}$C NMR (CDCl$_3$, 150 MHz) δ 187.9, 157.2, 153.3, 150.1, 148.0, 146.2, 137.3, 137.1, 129.1, 126.8, 126.3, 125.6, 124.1, 122.3, 120.4, 92.6, 79.0, 38.4, 27.7, 23.1, 19.1; IR (film) $v_{max}$ 2933, 2232, 1699, 1602, 1575, 1558, 1532, 1506, 1471, 1425, 1349, 1282, 1082, 1024, 990, 963, 785, 737, 675 cm$^{-1}$; ESI-TOF m/z 376.1295 ($C_{21}H_{17}N_3O_4+H^+$ requires 376.1292).

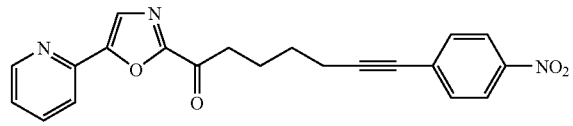

1-Oxo-1-[5-(2-pyridyl)oxazol-2-yl]-7-(4-nitrophenyl)hept-6-yne (4w). The title compound was prepared from 1-oxo-1-[5-(2-pyridyl)oxazol-2-yl]-hept-6-yne (3b (Boger, D. L.; Miyauchi, H.; et al. *J. Med. Chem.* 2005, 48, 1849-1856)) and 1-iodo-4-nitrobenzene following general procedure E. PTLC (SiO$_2$, 50% EtOAc-hexanes) afforded 4w (10 mg, 0.027 mmol, 67%) as a tan solid: $^1$H NMR (CDCl$_3$, 500 MHz) δ 8.68-8.66 (m, 1H), 8.13 (d, 2H, J=8.8 Hz), 7.87-7.85 (m, 2H), 7.81 (td, 1H, J=7.7, 1.8 Hz), 7.51 (d, 2H, J=8.8 Hz), 7.34-7.31 (m, 1H), 3.21 (t, 2H, J=7.4 Hz), 2.54 (t, 2H, J=7.0 Hz), 2.01-1.95 (m, 2H), 1.79-1.73 (m, 2H); $^{13}$C NMR (CDCl$_3$, 125 MHz) δ 187.8, 157.2, 153.3, 150.1, 146.6, 146.1, 137.1, 132.2, 130.6, 126.8, 124.1, 124.2, 123.4, 120.3, 95.7, 79.7, 38.4, 27.7, 23.0, 19.3; IR (film) $v_{max}$ 2943, 2231, 1704, 1593, 1515, 1467, 1425, 1342, 1284, 1107, 1082, 1025, 989, 963, 933, 854, 790, 750, 691 cm$^{-1}$; ESI-TOF m/z 376.1300 (C$_{21}$H$_{17}$N$_3$O$_4$+H$^+$ requires 376.1292).

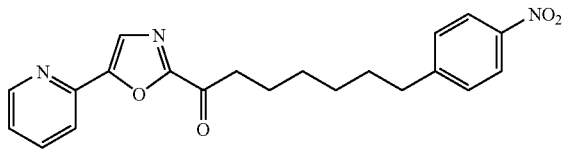

1-Oxo-1-[5-(2-pyridyl)oxazol-2-yl]-7-(4-nitrophenyl)heptane (5w). A solution of 1-oxo-1-[5-(2-pyridyl)oxazol-2-yl]-7-(4-nitrophenyl)hept-6-yne (4w, 10 mg, 0.027 mmol) in THF/t-BuOH (1/1, 0.8 mL) was treated with 0.05 equiv of Wilkinson's catalyst (Rh(PPh$_3$)$_3$Cl). The solution was purged with H$_2$ and stirred for 20 h at 25° C. The reaction mixture was filtered through Celite and concentrated. PTLC (SiO$_2$, 50% EtOAc-hexanes +1% Et$_3$N) afforded 5w (6 mg, 0.015 mmol, 79%) as a tan solid: $^1$H NMR (CDCl$_3$, 400 MHz) δ 8.69-8.67 (m, 1H), 8.14 (d, 2H, J=8.8 Hz), 7.89-7.86 (m, 2H), 7.82 (td, 1H, J=7.8, 1.8 Hz), 7.35-7.31 (m, 3H), 3.12 (t, 2H, J=7.3 Hz), 2.72 (t, 2H, J=7.7 Hz), 1.81-1.75 (m, 2H), 1.71-1.64 (m, 2H), 1.49-1.39 (m, 4H); $^{13}$C NMR (CDCl$_3$, 125 MHz) δ 188.3, 157.3, 153.3, 150.5, 150.1, 146.2, 137.1, 135.0, 129.1, 127.7, 124.2, 123.6, 120.4, 38.9, 35.7, 30.7, 28.8 (2C), 23.8; IR (film) ν$_{max}$ 2926, 2857, 1705, 1601, 1557, 1515, 1466, 1424, 1344, 797 cm$^{-1}$; ESI-TOF m/z 380.1614 (C$_{21}$H$_{21}$N$_3$O$_2$+H$^+$ requires 380.1610).

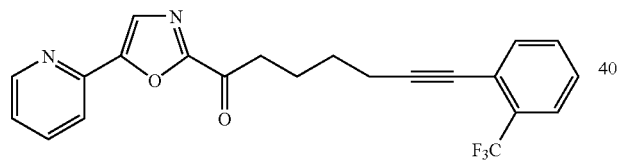

1-Oxo-1-[5-(2-pyridyl)oxazol-2-yl]-7-(2-(trifluoromethyl)phenyl)hept-6-yne (4x). The title compound was prepared from 1-oxo-1-[5-(2-pyridyl)oxazol-2-yl]-7-(trimethylsilyl)hept-6-yne (3a (Boger, D. L.; Miyauchi, H.; et al. *J. Med. Chem.* 2005, 48, 1849-1856)) and 2-iodo-trifluoromethylbenzene following general procedure D. PTLC (SiO$_2$, 50% EtOAc-hexanes) afforded 4x (13 mg, 0.032 mmol, 28%) as a white solid: $^1$H NMR (CDCl$_3$, 500 MHz) δ 8.67 (app d, 1H, J=4.8 Hz), 7.88-7.85 (m, 2H), 7.81 (td, 1H, J=7.4, 1.5 Hz), 7.60 (d, 1H, J=7.7 Hz), 7.53 (d, 1H, J=7.7 Hz), 7.44 (t, 1H, J=7.5 Hz), 7.36-7.31 (m, 2H), 3.20 (t, 2H, J=7.4 Hz), 2.54 (t, 2H, J=7.0 Hz), 2.02-1.96 (m, 2H), 1.79-1.72 (m, 2H); $^{13}$C NMR (CDCl$_3$, 125 MHz) δ 188.0, 157.3, 153.3, 150.1, 146.2, 137.1, 133.9, 131.4 (d, J=30.5 Hz), 131.2, 127.2, 126.9, 125.6 (q, J=4.8 Hz), 124.1, 123.6 (d, J=271.9 Hz), 122.2 (d, J=1.9 Hz), 120.4, 95.7, 77.3, 38.5, 27.3, 22.9, 19.3; IR (film) ν$_{max}$ 2929, 2864, 2234, 1703, 1603, 1575, 1504, 1490, 1469, 1426, 1318, 1169, 1133, 1111, 1062, 1033, 963, 844, 784, 766 cm$^{-1}$; ESI-TOF m/z 399.1326 (C$_{22}$H$_{17}$F$_3$N$_2$O$_2$+H$^+$ requires 399.1320).

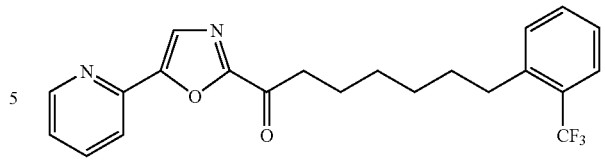

1-Oxo-1-[5-(2-pyridyl)oxazol-2-yl]-7-(2-(trifluoromethyl)phenyl)heptane (5x). The title compound was prepared from 1-oxo-1-[5-(2-pyridyl)oxazol-2-yl]-7-(2-(trifluoromethyl)phenyl)hept-6-yne (4x) following general procedure F. No further purification was required to yield 5x (8 mg, 0.02 mmol, 80%) as a yellow oil: $^1$H NMR (CDCl$_3$, 400 MHz) δ 8.69-8.67 (m, 1H), 7.89-7.86 (m, 2H), 7.82 (td, 1H, J=7.9, 1.8 Hz), 7.44-7.31 (m, 5H), 3.12 (t, 2H, J=7.3 Hz), 2.67 (t, 2H, J=7.6 Hz), 1.83-1.76 (m, 2H), 1.70-1.62 (m, 2H), 1.47-1.37 (m, 4H); $^{13}$C NMR (CDCl$_3$, 125 MHz) δ 188.4, 157.3, 153.3, 150.1, 146.3, 143.8, 137.1, 131.8, 130.5 (d, J=31.5 Hz), 128.6, 126.8, 125.0 (q, J=3.8 Hz), 124.1, 122.5 (t, J=3.8 Hz), 120.4, 39.0, 35.7, 31.1, 28.9 (2C), 23.8; IR (film) ν$_{max}$ 2929, 2857, 1699, 1606, 1575, 1505, 1470, 1426, 1313, 1165, 1119, 1059, 1034, 963, 784, 769, 741 cm$^{-1}$; ESI-TOF m/z 403.1629 (C$_{22}$H$_{21}$F$_3$N$_2$O$_2$+H$^+$ requires 403.1628).

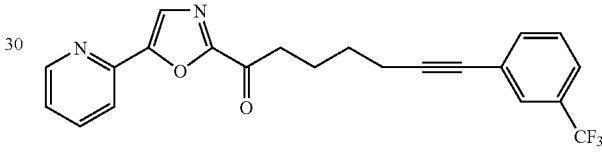

1-Oxo-1-[5-(2-pyridyl)oxazol-2-yl]-7-(3-(trifluoromethyl)phenyl)hept-6-yne (4y). The title compound was prepared from 1-oxo-1-[5-(2-pyridyl)oxazol-2-yl]-7-(trimethylsilyl)hept-6-yne (3a) and 3-iodo-trifluoromethylbenzene following general procedure D. PTLC (SiO$_2$, 50% EtOAc-hexanes) afforded 4y (31 mg, 0.078 mmol, 64%) as a yellow solid: $^1$H NMR (CDCl$_3$, 500 MHz) δ 8.67 (app d, 1H, J=4.4 Hz), 7.89-7.86 (m, 2H), 7.81 (td, 1H, J=7.7, 1.5 Hz), 7.65 (s, 1H), 7.55 (d, 1H, J=7.7 Hz), 7.50 (d, 1H, J=8.1 Hz), 7.39 (t, 1H, J=7.7 Hz), 7.34-7.31 (m, 1H), 3.21 (t, 2H, J=7.4 Hz), 2.51 (t, 2H, J=7.0 Hz), 2.01-1.95 (m, 2H), 1.78-1.72 (m, 2H); $^{13}$C NMR (CDCl$_3$, 100 MHz) δ 188.0, 157.2, 153.3, 150.1, 146.2, 137.1, 134.6, 128.6, 128.3 (q, J=4.5 Hz), 126.8, 125.1, 124.1, 124.0, 122.3, 120.4, 91.4, 79.7, 38.5, 27.8, 23.1, 19.1; IR (film) ν$_{max}$ 2934, 2866, 2233, 1699, 1603, 1576, 1504, 1469, 1426, 1335, 1237, 1166, 1127, 1072, 1024, 801, 784, 696 cm$^{-1}$; ESI-TOF m/z 399.1323 (C$_{22}$H$_{17}$F$_3$N$_2$O$_2$+H$^+$ requires 399.1320).

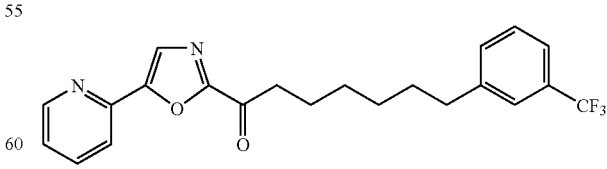

1-Oxo-1-[5-(2-pyridyl)oxazol-2-yl]-7-(3-(trifluoromethyl)phenyl)heptane (5y). The title compound was prepared from 1-oxo-1-[5-(2-pyridyl)oxazol-2-yl]-7-(3-(trifluoromethyl)phenyl)hept-6-yne (4y) following general procedure F. No further purification was required to yield 5y (7 mg, 0.017 mmol, 89%) as a pale yellow oil: $^1$H NMR (CDCl$_3$, 400 MHz) δ 8.69-8.67 (m, 1H), 7.89-7.86 (m, 2H), 7.82 (td, 1H, J=7.9, 1.8 Hz), 7.44-7.31 (m, 5H), 3.12 (t, 2H, J=7.3 Hz), 2.67 (t, 2H, J=7.6 Hz), 1.83-1.76 (m, 2H), 1.70-1.62 (m, 2H), 1.47-1.37 (m, 4H); $^{13}$C NMR (CDCl$_3$, 125 MHz) δ 188.4, 157.3, 153.3, 150.1, 146.3, 143.8, 137.1, 131.8, 130.5 (d, J=31.5 Hz), 128.6, 126.8, 125.0 (q, J=3.8 Hz), 124.1, 122.5 (t, J=3.8 Hz), 120.4, 39.0, 35.7, 31.1, 28.9 (2C), 23.8; IR (film) $v_{max}$ 2929, 2859, 1699, 1603, 1576, 1505, 1469, 1426, 1329, 1163, 1122, 1074, 784, 702 cm$^{-1}$; ESI-TOF m/z 403.1641 (C$_{22}$H$_{21}$F$_3$N$_2$O$_2$+ H$^+$ requires 403.1628).

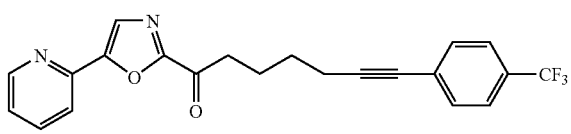

b 1-Oxo-1-[5-(2-pyridyl)oxazol-2-yl]-7-(4-(trifluoromethyl) phenyl)hept-6-yne (4z). The title compound was prepared from 1-oxo-1-[5-(2-pyridyl)oxazol-2-yl]-7-(trimethylsilyl)hept-6-yne (3a (Boger, D. L.; Miyauchi, H.; et al. *J. Med. Chem.* 2005, 48, 1849-1856)) and 4-iodo-trifluoromethylbenzene following general procedure D. PTLC (SiO$_2$, 50% EtOAc-hexanes) afforded 4z (28 mg, 0.070 mmol, 60%) as a yellow solid: $^1$H NMR (CDCl$_3$, 500 MHz) δ 8.67 (app d, 1H, J=4.4 Hz), 7.88-7.85 (m, 2H), 7.81 (td, 1H, J=7.7, 1.8 Hz), 7.52 (d, 2H, J=8.4 Hz), 7.48 (d, 2H, J=8.1 Hz), 7.34-7.31 (m, 1H), 3.20 (t, 2H, J=7.4 Hz), 2.51 (t, 2H, J=7.0 Hz), 2.01-1.95 (m, 2H), 1.78-1.71 (m, 2H); $^{13}$C NMR (CDCl$_3$, 100 MHz) δ 188.0, 157.2, 153.3, 150.1, 146.2, 137.1, 131.7, 129.2 (d, J=33.3 Hz), 127.7, 126.8, 125.1 (q, J=3.1 Hz), 124.1, 124.0 (d, J=270.0 Hz), 120.4, 91.4, 79.7, 38.5, 27.8, 23.1, 19.1; IR (film) $v_{max}$ 2934, 2866, 2232, 1698, 1614, 1577, 1503, 1469, 1426, 1323, 1166, 1125, 1067, 1017, 963, 843, 784 cm$^{-1}$; ESI-TOF m/z 399.1326 (C$_{22}$H$_{17}$F$_3$N$_2$O$_2$+H$^+$ requires 399.1320).

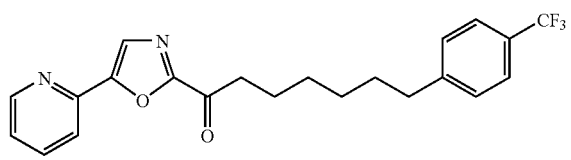

1-Oxo-1-[5-(2-pyridyl)oxazol-2-yl]-7-(4-(trifluoromethyl) phenyl)heptane (5z). The title compound was prepared from 1-oxo-1-[5-(2-pyridyl)oxazol-2-yl]-7-(4-(trifluoromethyl)phenyl)hept-6-yne (4z) following general procedure F. No further purification was required to yield 5z (12 mg, 0.03 mmol, 93%) as a white solid: $^1$H NMR (CDCl$_3$, 400 MHz) δ 8.68-8.66 (m, 1H), 7.89-7.86 (m, 2H), 7.81 (td, 1H, J=7.7, 1.8 Hz), 7.52 (d, 2H, J=8.2 Hz), 7.34-7.31 (m, 1H), 7.28 (d, 2H, J=8.0 Hz), 3.12 (t, 2H, J=7.3 Hz), 2.67 (t, 2H, J=7.6 Hz), 1.83-1.75 (m, 2H), 1.69-1.62 (m, 2H), 1.48-1.39 (m, 4H); $^{13}$C NMR (CDCl$_3$, 150 MHz) δ 188.4, 157.3, 153.3, 150.1, 146.7, 137.1, 128.6, 128.1, 127.9, 126.8, 125.1 (q, J=3.4 Hz), 124.1, 120.4, 39.0, 35.6, 30.9, 28.9 (2C), 23.8; IR (film) $v_{max}$ 3104, 2933, 2855, 1698, 1604, 1503, 1468, 1428, 1385, 1327, 1237, 1162, 1109, 1068, 962, 845, 821, 783 cm$^{-1}$; ESI-TOF m/z 403.1640 (C$_{22}$H$_{21}$F$_3$N$_2$O$_2$+H$^+$ requires 403.1628).

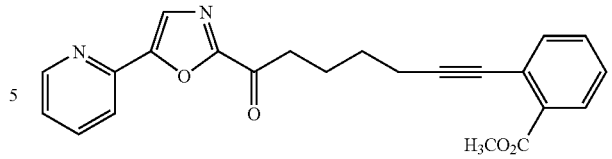

1-Oxo-1-[5-(2-pyridyl)oxazol-2-yl]-7-(2-(methoxycarbonyl)phenyl)hept-6-yne (4aa). The title compound was prepared from 1-oxo-1-[5-(2-pyridyl)oxazol-2-yl]-7-(trimethylsilyl)hept-6-yne (3a (Boger, D. L.; Miyauchi, H.; et al. *J. Med. Chem.* 2005, 48, 1849-1856)) and methyl 2-iodobenzoate following general procedure D. PTLC (SiO$_2$, 50% EtOAc-hexanes) afforded 4aa (10 mg, 0.026 mmol, 29%) as a yellow oil: $^1$H NMR (CDCl$_3$, 500 MHz) δ 8.67 (app d, 1H, J=4.8 Hz), 7.89-7.85 (m, 3H), 7.81 (td, 1H, J=7.4, 1.5 Hz), 7.51 (d, 1H, J=7.7 Hz), 7.42 (td, 1H, J=7.4, 1.3 Hz), 7.33-7.28 (m, 2H), 3.91 (s, 3H), 3.21 (t, 2H, J=7.4 Hz), 2.57 (t, 2H, J=7.0 Hz), 2.04-1.97 (m, 2H), 1.79-1.75 (m, 2H); $^{13}$C NMR (CDCl$_3$, 100 MHz) δ 188.1, 166.9, 157.3, 153.2, 150.1, 146.2, 137.1, 134.3, 131.8, 131.5, 130.1, 127.2, 126.8, 124.2, 124.1, 120.4, 95.0, 79.7, 52.1, 38.6, 28.0, 23.1, 19.6; IR (film) $v_{max}$ 2948, 2313, 1728, 1693, 1600, 1503, 1468, 1426, 1294, 1251, 1129, 1083, 785, 760 cm$^{-1}$; ESI-TOF m/z 389.1507 (C$_{23}$H$_{20}$N$_2$O$_4$+H$^+$ requires 389.1496).

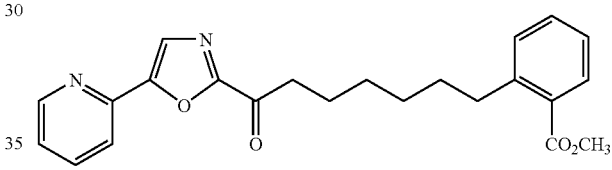

1-Oxo-1-[5-(2-pyridyl)oxazol-2-yl]-7-(2-(methoxycarbonyl)phenyl)heptane (5aa). The title compound was prepared from 1-oxo-1-[5-(2-pyridyl)oxazol-2-yl]-7-(2-(methoxycarbonyl)phenyl)hept-6-yne (4aa) following general procedure F. No further purification was required to yield 5aa (4 mg, 0.010 mmol, 57%) as a colorless film: $^1$H NMR (CDCl$_3$, 500 MHz) δ 8.68 (app d, 1H J=4.8 Hz), 7.89 (s, 1H), 7.87-7.84 (m, 2H), 7.82 (td, 1H, J=7.6, 1.8 Hz), 7.41 (td, 1H, J=7.7, 1.5 Hz), 7.26-7.22 (m, 2H), 3.90 (s, 3H), 3.12 (t, 2H, J=7.3 Hz), 2.95 (t, 2H, J=7.7 Hz), 1.81-1.76 (m, 2H), 1.63-1.57 (m, 2H), 1.48-1.43 (m, 4H); $^{13}$C NMR (CDCl$_3$, 125 MHz) δ 188.5, 169.9, 153.0, 144.0, 137.9, 134.7, 133.3, 127.1, 120.7, 118.6, 117.6, 116.3, 113.2, 45.4, 41.5, 39.1, 37.3, 37.0, 32.8; IR (film) $v_{max}$ 2927, 2855, 1722, 1699, 1602, 1575, 1504, 1469, 1426, 1259, 1094, 963, 785, 753, 711 cm$^{-1}$; ESI-TOF m/z 393.1813 (C$_{23}$H$_{24}$N$_2$O$_4$+H$^+$ requires 393.1809).

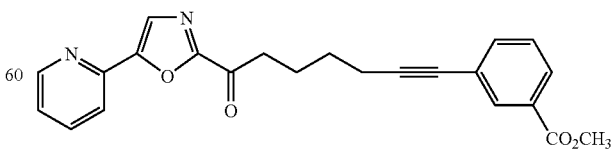

1-Oxo-1-[5-(2-pyridyl)oxazol-2-yl]-7-(3-(methoxycarbonyl)phenyl)hept-6-yne (4bb). The title compound was prepared from 1-oxo-1-[5-(2-pyridyl)oxazol-2-yl]-7-(trimethylsilyl)hept-6-yne (3a (Boger, D. L.; Miyauchi, H.; et al. *J. Med. Chem.* 2005, 48, 1849-1856)) and methyl 3-iodobenzoate following general procedure D. PTLC (SiO$_2$, 50% EtOAc-hexanes) afforded 4bb (12 mg, 0.031 mmol, 34%) as a pale yellow solid: $^1$H NMR (CDCl$_3$, 500 MHz) δ 8.67 (app d, 1H, J=4.8 Hz), 8.06 (d, 1H, J=1.5 Hz), 7.92 (dt, 1H, J=9.1, 1.4 Hz), 7.89-7.85 (m, 2H), 7.81 (td, 1H, J=7.7, 1.8 Hz), 7.56 (dt, 1H, J=7.7, 1.4 Hz), 7.35 (t, 1H, J=7.7 Hz), 7.33-7.30 (m, 1H), 3.91 (s, 3H), 3.20 (t, 2H, J=7.7 Hz), 2.50 (t, 2H, J=7.3 Hz), 2.02-1.96 (m, 2H), 1.78-1.72 (m, 2H); $^{13}$C NMR (CDCl$_3$, 100 MHz) δ 188.0, 166.5, 157.3, 153.2, 150.0, 146.2, 137.2, 135.8, 132.7, 130.2, 128.6, 128.3, 126.9, 124.3, 124.2, 124.2, 120.4, 90.6, 80.1, 52.2, 38.5, 27.9, 23.1, 19.2; IR (film) ν$_{max}$ 2949, 2353, 1722, 1698, 1601, 1573, 1503, 1469, 1426, 1298, 1230, 1107, 1083, 1024, 785, 755 cm$^{-1}$; ESI-TOF m/z 389.1510 (C$_{23}$H$_{20}$N$_2$O$_4$+H$^+$ requires 389.1496).

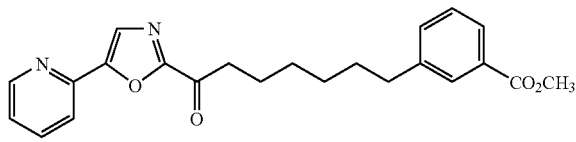

1-Oxo-1-[5-(2-pyridyl)oxazol-2-yl]-7-(3-(methoxycarbonyl)phenyl)heptane (5bb). The title compound was prepared from 1-oxo-1-[5-(2-pyridyl)oxazol-2-yl]-7-(3-(methoxycarbonyl)phenyl)hept-6-yne (4bb) following general procedure F. PTLC (SiO$_2$, 50% EtOAc-hexanes) afforded 5bb (6 mg, 0.015 mmol, 79%) as a pale yellow film: $^1$H NMR (CDCl$_3$, 500 MHz) δ 8.68 (app d, 1H, J=4.8 Hz), 7.89 (s, 1H), 7.87-7.84 (m, 3H), 7.82 (td, 1H, J=7.7, 1.5 Hz), 7.40-7.31 (m, 3H), 3.92 (s, 3H), 3.12 (t, 2H, J=7.4 Hz), 2.66 (t, 2H, J=7.7 Hz), 1.82-1.76 (m, 2H), 1.70-1.63 (m, 2H), 1.47-1.39 (m, 4H); $^{13}$C NMR (CDCl$_3$, 150 MHz) δ 188.5, 169.8, 153.0, 150.1, 143.0, 137.1, 133.1, 130.1, 129.5, 128.3, 127.0, 126.8, 120.4, 52.1, 39.0, 35.6, 31.1, 29.7, 28.9, 23.9; IR (film) ν$_{max}$ 2927, 2855, 1716, 1699, 1602, 1575, 1505, 1470, 1425, 1283, 1201, 1108, 1035, 785, 752 cm$^{-1}$; ESI-TOF m/z 393.1816 (C$_{23}$H$_{24}$N$_2$O+H$^+$ requires 393.1809).

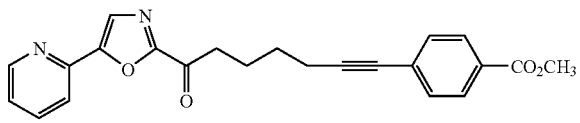

1-Oxo-1-[5-(2-pyridyl)oxazol-2-yl]-7-(4-(methoxycarbonyl)phenyl)hept-6-yne (4 cc). The title compound was prepared from 1-oxo-1-[5-(2-pyridyl)oxazol-2-yl]-7-(trimethylsilyl)hept-6-yne (3a (Boger, D. L.; Miyauchi, H.; et al. *J. Med. Chem.* 2005, 48, 1849-1856)) and methyl 4-iodobenzoate following general procedure D. PTLC (SiO$_2$, 50% EtOAc-hexanes) afforded 4 cc (12 mg, 0.031 mmol, 34%) as a pale yellow solid: $^1$H NMR (CDCl$_3$, 500 MHz) δ 8.68 (br s, 1H), 7.94 (d, 1H, J=8.4 Hz), 7.88-7.80 (m, 3H), 7.44 (d, 1H, J=8.4 Hz), 7.33 (m, 1H), 3.91 (s, 3H), 3.21 (t, 2H, J=7.4 Hz), 2.50 (t, 2H, J=7.0 Hz), 2.02-1.96 (m, 2H), 1.78-1.72 (m, 2H); $^{13}$C NMR (CDCl$_3$, 100 MHz) δ 188.0, 166.6, 157.3, 153.2, 150.0, 146.2, 137.1, 131.5, 129.4, 128.8, 128.6, 126.9, 124.1, 120.4, 93.0, 80.6, 52.1, 38.5, 27.8, 23.1, 19.3; IR (film) ν$_{max}$ 3097, 2949, 2224, 1715, 1691, 1604, 1573, 1501, 1470, 1427, 1277, 1177, 1109, 1019, 963, 856, 784, 769 cm$^{-1}$; ESI-TOF m/z 389.1495 (C$_{23}$H$_{20}$N$_2$O$_4$+H$^+$ requires 389.1496).

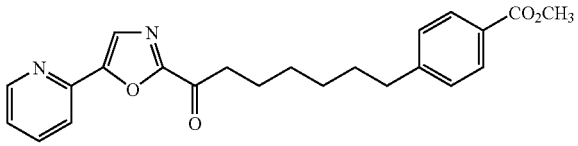

1-Oxo-1-[5-(2-pyridyl)oxazol-2-yl]-7-(4-(methoxycarbonyl)phenyl)heptane (5 cc). The title compound was prepared from 1-oxo-1-[5-(2-pyridyl)oxazol-2-yl]-7-(4-(methoxycarbonyl)phenyl)hept-6-yne (4 cc) following general procedure F. No further purification was required to yield 5 cc (7 mg, 0.018 mmol, 88%) as a white solid: $^1$H NMR (CDCl$_3$, 500 MHz) δ 8.68-8.66 (m, 1H), 7.95 (d, 2H, J=8.5 Hz), 7.89 (s, 1H), 7.86 (m, 1H), 7.82 (td, 1H, J=7.8, 1.8 Hz), 7.34-7.31 (m, 1H), 7.24 (d, 2H, J=8.5 Hz), 3.90 (s, 3H), 3.11 (t, 2H, J=7.3 Hz), 2.67 (t, 2H, J=7.6 Hz), 1.82-1.75 (m, 2H), 1.69-1.62 (m, 2H), 1.47-1.38 (m, 4H); $^{13}$C NMR (CDCl$_3$, 125 MHz) δ 188.4, 167.1, 157.3, 153.2, 150.1, 148.2, 146.2, 137.1, 129.6, 128.4, 127.6, 126.8, 124.1, 120.4, 51.9, 39.0, 35.8, 30.9, 28.9 (2C), 23.8; IR (film) ν$_{max}$ 2928, 2855, 1716, 1694, 1602, 1502, 1469, 1432, 1383, 1281, 1180, 1112, 1037, 989, 962, 937, 791, 759 cm$^{-1}$; ESI-TOF m/z 393.1808 (C$_{23}$H$_{24}$N$_2$O$_4$+H$^+$ requires 393.1809).

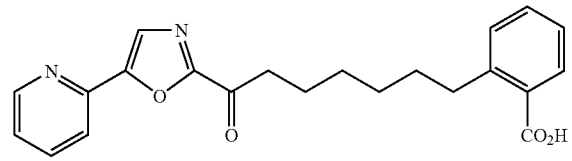

2-(7-Oxo-7-(5-(pyridin-2-yl)oxazol-2-yl)heptyl)benzoic acid (5dd). The title compound was prepared from 1-oxo-1-[5-(2-pyridyl)oxazol-2-yl]-7-(2-(methoxycarbonyl)phenyl)heptane (5aa) following general procedure L. PTLC (SiO$_2$, 50% EtOAc-hexanes) afforded 5dd (8 mg, 21%) as a white solid: $^1$H NMR (CDCl$_3$, 600 MHz) δ 8.72 (br s), 8.01 (app d, J=8.4 Hz, 1H), 7.81-7.91 (m, 3H), 7.44 (app t, J=7.8 Hz, 1H), 7.34 (app s, 1H), 7.25-7.27 (m, 3H), 3.12 (t, J=7.2 Hz, 2H), 3.02 (t, J=7.8 Hz, 2H), 1.79-1.81 (m, 2H), 1.64-1.67 (m, 2H), 1.43-1.50 (m, 4H); $^{13}$C NMR (CDCl$_3$, 100 MHz) δ 188.6, 171.1, 157.4, 153.0, 150.0, 146.0, 145.4, 137.4, 132.5, 131.4, 131.1, 128.4, 127.0, 125.8, 124.3, 120.6, 39.1, 34.3, 31.3, 29.0, 28.6, 23.9; ESI-TOF m/z 379.1659 (C$_{22}$H$_{22}$N$_2$O$_4$+H$^+$ requires 379.1652).

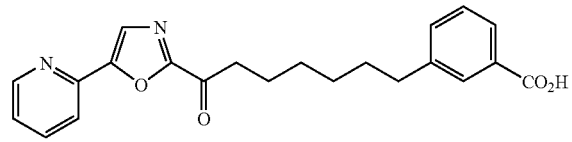

3-(7-Oxo-7-(5-(pyridin-2-yl)oxazol-2-yl)heptyl)benzoic acid (5ee). The title compound was prepared from 1-oxo-1-[5-(2-pyridyl)oxazol-2-yl]-7-(3-(methoxycarbonyl)phenyl)heptane (5bb) following general procedure L. PTLC (SiO$_2$, 50% EtOAc-hexanes) afforded 5ee (5 mg, 15%) as a white solid: $^1$H NMR (CDCl$_3$, 600 MHz) δ 8.72 (app d, J=4.2 Hz, 1H), 7.86-7.93 (m, 4H), 7.83 (t, J=5.0 Hz, 1H), 7.36-7.42 (m, 2H), 7.34 (app t, J=6.0 Hz, 1H), 3.13 (t, J=7.8 Hz, 2H), 2.69 (t, J=7.8 Hz, 2H), 1.80 (quint, J=7.2 Hz, 2H), 1.68 (quint, J=7.2 Hz, 2H), 1.38-1.49 (m, 4H). $^{13}$C NMR (CDCl$_3$, 100 MHz) δ 188.4, 170.6, 157.4, 153.0, 150.1, 146.1, 143.0, 137.3, 133.8, 130.1, 129.3, 128.4, 127.6, 127.0, 124.2, 120.6, 39.0, 35.4, 31.0, 28.7, 28.5, 23.8; ESI-TOF m/z 379.1654 (C$_{22}$H$_{22}$N$_2$O$_4$+H$^+$ requires 379.1652).

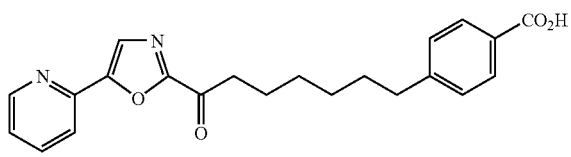

4-(7-Oxo-7-(5-(pyridin-2-yl)oxazol-2-yl)heptyl)benzoic acid (5 ft). The title compound was prepared from 1-oxo-1-[5-(2-pyridyl)oxazol-2-yl]-7-(4-(methoxycarbonyl)-phenyl)heptane (5 cc) following general procedure L. PTLC (SiO$_2$, 50% EtOAc-hexanes) afforded 5ff (6 mg, 33%) as a white solid: $^1$H NMR (CDCl$_3$, 600 MHz) δ 8.69 (app d, J=4.2 Hz, 1H), 8.02 (app d, J=7.8 Hz, 2H), 7.87-7.90 (m, 2H), 7.82 (app t, J=7.8 Hz, 1H), 7.33 (app t, J=5.4 Hz, 1H), 7.26-7.28 (m, 2H), 3.11 (t, J=7.2 Hz, 2H), 2.69 (t, J=7.8 Hz, 2H), 1.79 (quint, J=7.2 Hz, 2H), 1.67 (quint, J=7.8 Hz, 2H), 1.41-1.47 (m, 4H); $^{13}$C NMR (CDCl$_3$, 150 MHz) δ 188.4, 171.1, 157.4, 153.2, 150.1, 149.1, 146.2, 137.2, 130.3, 128.5, 126.9, 125.9, 124.2, 120.5, 39.0, 36.0, 30.8, 28.9, 23.9; ESI-TOF m/z 379.1652 (C$_{22}$H$_{22}$N$_2$O$_4$+H$^+$ requires 379.1652).

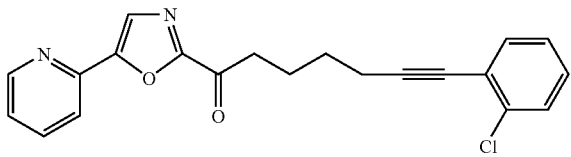

1-Oxo-1-[5-(2-pyridyl)oxazol-2-yl]-7-(2-chlorophenyl)hept-6-yne (4gg). The title compound was prepared from 1-oxo-1-[5-(2-pyridyl)oxazol-2-yl]-hept-6-yne (3b (Boger, D. L.; Miyauchi, H.; et al. J. Med. Chem. 2005, 48, 1849-1856)) and 1-chloro-2-iodobenzene following general procedure E. PTLC (SiO$_2$, 50% EtOAc-hexanes) afforded 4gg (27 mg, 0.074 mmol, 63%) as a yellow solid: $^1$H NMR (CDCl$_3$, 500 MHz) δ 8.68-8.66 (m, 1H), 7.89-7.86 (m, 2H), 7.82 (td, 1H, J=7.7, 1.8 Hz), 7.44-7.42 (m, 1H), 7.37-7.31 (m, 2H), 7.21-7.15 (m, 2H), 3.21 (t, 2H, J=7.4 Hz), 2.56 (t, 2H, J=7.0 Hz), 2.05-1.99 (m, 2H), 1.80-1.74 (m, 2H); $^{13}$C NMR (CDCl$_3$, 125 MHz) δ 188.0, 157.3, 153.2, 150.1, 146.2, 137.1, 135.7, 133.2, 129.1, 128.5, 126.8, 126.3, 124.1, 123.6, 120.4, 95.2, 78.0, 38.5, 27.9, 23.0, 19.3; IR (film) ν$_{max}$ 3055, 2931, 2865, 2232, 1699, 1602, 1575, 1558, 1505, 1471, 1429, 1385, 1283, 1152, 1118, 1083, 1065, 1032, 990, 962, 784, 756 cm$^{-1}$; ESI-TOF m/z 365.1053 (C$_{21}$H$_{17}$ClN$_2$O$_4$+H$^+$ requires 365.1051).

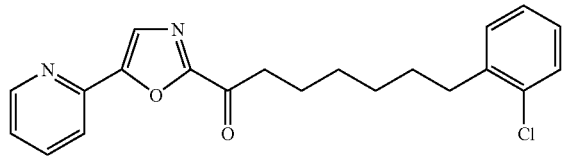

1-Oxo-1-[5-(2-pyridyl)oxazol-2-yl]-7-(2-chlorophenyl)heptane (5gg). The title compound was prepared from 1-oxo-1-[5-(2-pyridyl)oxazol-2-yl]-7-(2-chlorophenyl)hept-6-yne (4gg) following general procedure G. PTLC (SiO$_2$, 43% EtOAc-hexanes) afforded 5gg (11 mg, 0.030 mmol, 78%) as a white solid: $^1$H NMR (CDCl$_3$, 500 MHz) δ 8.68-8.66 (m, 1H), 7.89-7.86 (m, 2H), 7.82 (td, 1H, J=7.7, 1.5 Hz), 7.34-7.31 (m, 2H), 7.22-7.15 (m, 2H), 7.12 (td, 1H, J=7.3, 1.8 Hz), 3.12 (t, 2H, J=7.4 Hz), 2.73 (t, 2H, J=7.8 Hz), 1.83-1.77 (m, 2H), 1.67-1.61 (m, 2H), 1.50-1.40 (m, 4H); $^{13}$C NMR (CDCl$_3$, 125 MHz) δ 188.5, 157.3, 153.2, 150.1, 146.3, 140.2, 137.1, 133.8, 130.3, 129.4, 127.1, 126.8, 126.6, 124.1, 120.4, 39.1, 33.5, 29.5, 29.1, 28.9, 23.9; IR (film) ν$_{max}$ 3056, 2929, 2857, 1694, 1602, 1575, 1505, 1470, 1425, 1382, 1283, 1151, 1118, 1081, 1050, 989, 962, 935, 784, 752 cm$^{-1}$; ESI-TOF m/z 369.1366 (C$_{21}$H$_{21}$ClN$_2$O$_2$+H$^+$ requires 369.1364).

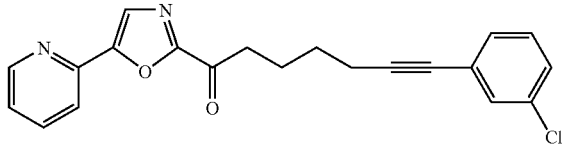

1-Oxo-1-[5-(2-pyridyl)oxazol-2-yl]-7-(3-chlorophenyl)hept-6-yne (4hh). The title compound was prepared from 1-oxo-1-[5-(2-pyridyl)oxazol-2-yl]-hept-6-yne (3b (Boger, D. L.; Miyauchi, H.; et al. J. Med. Chem. 2005, 98, 1849-1856)) and 1-chloro-3-iodobenzene following general procedure E. PTLC (SiO$_2$, 50% EtOAc-hexanes) afforded 4hh (24 mg, 0.066 mmol, 56%) as a yellow solid: $^1$H NMR (CDCl$_3$, 500 MHz) δ 8.68-8.66 (m, 1H), 7.89-7.86 (m, 2H), 7.82 (td, 1H, J=7.7, 1.8 Hz), 7.38 (m, 1H), 7.34-7.31 (m, 1H), 7.27-7.18 (m, 3H), 3.20 (t, 2H, J=7.4 Hz), 2.49 (t 2H, J=7.0 Hz), 2.00-1.95 (m, 2H), 1.77-1.71 (m, 2H); $^{13}$C NMR (CDCl$_3$, 125 MHz) δ 187.9, 157.2, 153.3, 150.1, 146.2, 137.1, 133.9, 131.4, 129.6, 129.3, 127.8, 126.8, 125.5, 124.1, 120.3, 90.9, 79.8, 38.5, 27.8, 23.1, 19.1; IR (film) ν$_{max}$ 3061, 2932, 2865, 2230, 1703, 1592, 1575, 1558, 1505, 1471, 1426, 1385, 1283, 1243, 1152, 1081, 1065, 1023, 990, 962, 930, 880, 784, 740, 683 cm$^{-1}$; ESI-TOF m/z 365.1058 (C$_{21}$H$_{17}$ClN$_2$O$_4$+H$^+$ requires 365.1051).

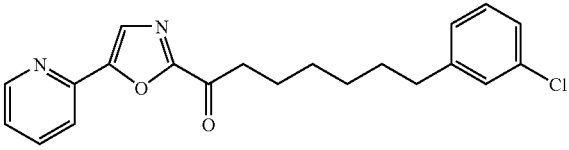

1-Oxo-1-[5-(2-pyridyl)oxazol-2-yl]-7-(3-chlorophenyl)heptane (5hh). The title compound was prepared from 1-oxo-1-[5-(2-pyridyl)oxazol-2-yl]-7-(3-chlorophenyl)hept-6-yne (4hh) following general procedure G. PTLC (SiO$_2$, 40% EtOAc-hexanes) afforded 5hh (10 mg, 0.027 mmol, 67%) as a white solid: $^1$H NMR (CDCl$_3$, 600 MHz) δ 8.68-8.66 (m, 1H), 7.89-7.86 (m, 2H), 7.82 (td, 1H, J=7.8, 1.4 Hz), 7.34-7.31 (m, 1H), 7.21-7.14 (m, 3H), 7.04 (d, 1H, J=7.5 Hz), 3.11 (t, 2H, J=7.4 Hz), 2.59 (t, 2H, J=7.4 Hz), 1.81-1.76 (m, 2H), 1.65-1.60 (m, 2H), 1.46-1.36 (m, 4H); $^{13}$C NMR (CDCl$_3$, 125 MHz) δ 188.4, 157.3, 153.2, 150.1, 146.3, 144.7, 137.1, 133.9, 129.5, 128.5, 126.8, 126.6, 124.1, 120.4, 39.0, 35.5, 31.0, 28.9, 28.8, 23.8; IR (film) $v_{max}$ 2930, 2856, 1698, 1601, 1575, 1505, 1470, 1426, 1385, 1285, 1081, 1035, 990, 962, 935, 783, 741, 696 cm$^{-1}$; ESI-TOF m/z 369.1363 (C$_{21}$H$_{21}$ClN$_2$O$_2$+H$^+$ requires 369.1364).

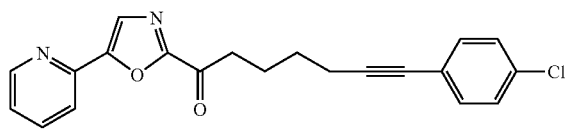

1-Oxo-1-[5-(2-pyridyl)oxazol-2-yl]-7-(4-chlorophenyl) hept-6-yne (4ii). The title compound was prepared from 1-oxo-1-[5-(2-pyridyl)oxazol-2-yl]-hept-6-yne (3b (Boger, D. L.; Miyauchi, H.; et al. *J. Med. Chem.* 2005, 48, 1849-1856)) and 1-chloro-4-iodobenzene following general procedure E. PTLC (SiO$_2$, 50% EtOAc-hexanes) afforded 4ii (21 mg, 0.058 mmol, 50%) as a yellow solid: $^1$H NMR (CDCl$_3$, 400 MHz) δ 8.68 (app d, 1H, J=4.7 Hz), 7.88-7.86 (m, 2H), 7.81 (td, 1H, J=7.7, 1.7 Hz), 7.34-7.30 (m, 3H), 7.23 (d, 2H, J=12.3 Hz), 3.20 (t, 2H, J=7.4 Hz), 2.48 (t, 2H, J=7.0 Hz), 2.01-1.93 (m, 2H), 1.77-1.69 (m, 2H); $^{13}$C NMR (CDCl$_3$, 125 MHz) δ 188.0, 157.2, 153.3, 150.1, 146.2, 137.1, 133.4, 132.7, 128.4, 126.8, 124.1, 122.3, 120.3, 90.6, 80.0, 38.5, 27.9, 23.1, 19.2; IR (film) $v_{max}$ 3097, 2941, 2350, 1698, 1604, 1488, 1471, 1426, 1285, 1243, 1193, 1088, 1025, 1012, 959, 933, 824, 785 cm$^{-1}$; ESI-TOF m/z 365.1049 (C$_{21}$H$_{17}$ClN$_2$O$_4$+H$^+$ requires 365.1051).

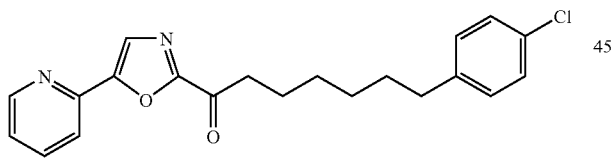

1-Oxo-1-[5-(2-pyridyl)oxazol-2-yl]-7-(4-chlorophenyl)heptane (5ii). The title compound was prepared from 1-oxo-1-[5-(2-pyridyl)oxazol-2-yl]-7-(4-chlorophenyl)hept-6-yne (4ii) following general procedure G. PTLC (SiO$_2$, 50% EtOAc-hexanes) afforded 5ii (6 mg, 0.016 mmol, 60%) as a white solid: $^1$H NMR (CDCl$_3$, 400 MHz) δ 8.69-8.67 (m, 1H), 7.89-7.86 (m, 2H), 7.82 (td, 1H, J=7.8, 1.8 Hz), 7.34-7.31 (m, 2H), 7.24 (d, 2H, J=8.2 Hz), 7.09 (d, 2H, J=8.2 Hz), 3.11 (t, 2H, J=7.3 Hz), 2.58 (t, 2H, J=7.7 Hz), 1.82-1.75 (m, 2H), 1.65-1.57 (m, 2H), 1.47-1.35 (m, 4H); $^{13}$C NMR (CDCl$_3$, 125 MHz) δ 188.4, 157.3, 153.3, 150.1, 146.3, 141.0, 137.1, 131.2, 129.7, 128.3, 126.8, 124.1, 120.4, 39.0, 35.1, 31.1, 28.9, 28.8, 23.8; IR (film) $v_{max}$ 2933, 2858, 1698, 1602, 1574, 1505, 1470, 1426, 1094, 817, 787, 741, 693 cm$^{-1}$; ESI-TOF m/z 369.1367 (C$_{21}$H$_{21}$ClN$_2$O$_2$+H$^+$ requires 369.1364).

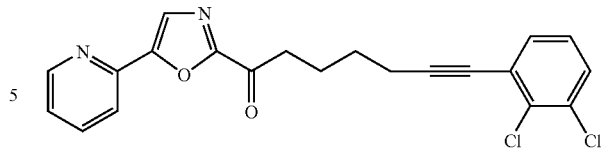

1-Oxo-1-[5-(2-pyridyl)oxazol-2-yl]-7-(2,3-dichlorophenyl) hept-6-yne (4jj). The title compound was prepared from 1-oxo-1-[5-(2-pyridyl)oxazol-2-yl]-hept-6-yne (3b (Boger, D. L.; Miyauchi, H.; et al. *J. Med. Chem.* 2005, 48, 1849-1856)) and 1,2-dichloro-3-iodobenzene following general procedure E. PTLC (SiO$_2$, 50% EtOAc-hexanes) afforded 4jj (59 mg, 0.148 mmol, 63%) as a yellow solid: $^1$H NMR (CDCl$_3$, 400 MHz) δ 8.67 (app d, 1H, J=4.4 Hz), 7.88-7.86 (m, 2H), 7.82 (td, 1H, J=7.8, 1.8 Hz), 7.36-7.31 (m, 3H), 7.10 (t, 1H, J=7.9 Hz), 3.21 (t, 2H, J=7.3 Hz), 2.57 (t, 2H, J=7.0 Hz), 2.05-1.97 (m, 2H), 1.81-1.73 (m, 2H); $^{13}$C NMR (CDCl$_3$, 150 MHz) δ 187.9, 157.2, 153.3, 150.1, 146.2, 137.1, 134.1, 133.0, 131.4, 129.4, 126.8, 125.7, 124.1, 120.3, 96.2, 77.8, 38.4, 27.7, 23.0, 19.6; IR (film) $v_{max}$ 2931, 2864, 2232, 1708, 1604, 1579, 1503, 1469, 1426, 1408, 1383, 1238, 1191, 1154, 1084, 1024, 991, 963, 913, 783, 741 cm$^{-1}$; ESI-TOF m/z 399.0668 (C$_{21}$H$_{16}$Cl$_2$N$_2$O$_2$+H$^+$ requires 399.0662).

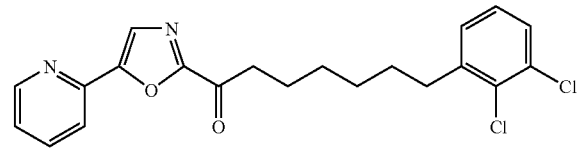

1-Oxo-1-[5-(2-pyridyl)oxazol-2-yl]-7-(2,3-dichlorophenyl) heptane (5jj). The title compound was prepared from 1-oxo-1-[5-(2-pyridyl)oxazol-2-yl]-7-(2,3-dichlorophenyl)hept-6-yne (4jj) following general procedure G. PTLC (SiO$_2$, 50% EtOAc-hexanes) afforded 5jj (8 mg, 0.020 mmol, 36%) as a pale yellow solid: $^1$H NMR (CDCl$_3$, 600 MHz) δ 8.68 (app d, 1H, J=4.4 Hz), 7.89-7.87 (m, 2H), 7.82 (td, 1H, J=7.8, 1.8 Hz), 7.34-7.29 (m, 2H), 7.12-7.10 (m, 2H), 3.13 (t, 2H, J=7.4 Hz), 2.77 (t, 2H, J=7.8 Hz), 1.83-1.78 (m, 2H), 1.67-1.62 (m, 2H), 1.49-1.42 (m, 4H); $^{13}$C NMR (CDCl$_3$, 150 MHz) δ 188.4, 157.3, 153.3, 150.1, 146.3, 142.6, 137.1, 133.0, 132.1, 128.4, 128.0, 127.0, 126.8, 124.1, 120.4, 39.0, 34.5, 29.3, 29.0, 28.9, 23.9; IR (film) $v_{max}$ 2928, 2857, 1698, 1602, 1575, 1504, 1469, 1426, 1382, 1282, 1237, 1186, 1152, 1118, 1081, 1044, 990, 963, 936, 853, 783, 740 cm$^{-1}$; ESI-TOF m/z 403.0964 (C$_{21}$H$_{20}$Cl$_2$N$_2$O$_2$+H$^+$ requires 403.0975).

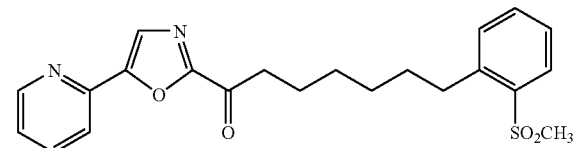
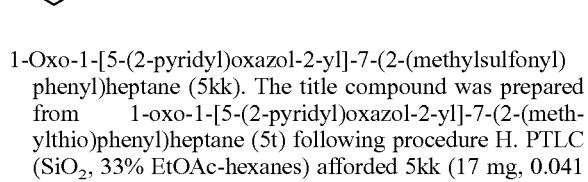

1-Oxo-1-[5-(2-pyridyl)oxazol-2-yl]-7-(2-(methylsulfonyl) phenyl)heptane (5kk). The title compound was prepared from 1-oxo-1-[5-(2-pyridyl)oxazol-2-yl]-7-(2-(methylthio)phenyl)heptane (5t) following procedure H. PTLC (SiO$_2$, 33% EtOAc-hexanes) afforded 5kk (17 mg, 0.041 mmol, 83%) as a white solid: $^1$H NMR (CDCl$_3$, 400 MHz) δ 8.68 (app d, 1H, J=4.4 Hz), 8.02 (dd, 1H, J=7.9, 1.2 Hz), 7.89-7.86 (m, 2H), 7.82 (td, 1H, J=7.7, 1.8 Hz), 7.55 (td, 1H, J=7.6, 1.2 Hz), 7.39-7.31 (m, 3H), 3.12 (t, 2H, J=7.3 Hz), 3.08 (s, 3H), 3.02 (t, 2H, J=7.9 Hz), 1.84-1.69 (m, 4H), 1.54-1.44 (m, 4H); $^{13}$C NMR (CDCl$_3$, 150 MHz) δ 188.4, 157.3, 153.1, 150.0, 146.1, 142.6, 138.3, 137.2, 133.6, 131.6, 129.4, 126.9, 126.6, 124.2, 120.4, 44.7, 39.0, 32.9, 31.8, 29.4, 28.8, 23.7; IR (film) ν$_{max}$ 2931, 2857, 1699, 1602, 1575, 1505, 1470, 1427, 1306, 1247, 1151, 1082, 962, 914, 785, 753 cm$^{-1}$; ESI-TOF m/z 413.1524 (C$_{22}$H$_{24}$N$_2$O$_4$S+H$^+$ requires 413.1529).

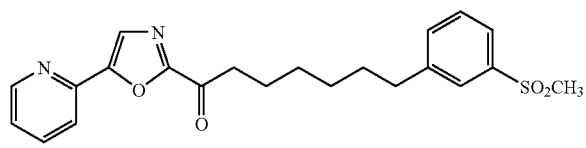

1-Oxo-1-[5-(2-pyridyl)oxazol-2-yl]-7-(3-(methylsulfonyl) phenyl)heptane (5ll). The title compound was prepared from 1-oxo-1-[5-(2-pyridyl)oxazol-2-yl]-7-(3-(methylthio)phenyl)heptane (5u) following procedure H. PTLC (SiO$_2$, 50% EtOAc-hexanes) afforded 5ll (18 mg, 0.043 mmol, 64%) as a white solid: $^1$H NMR (CDCl$_3$, 500 MHz) δ 8.69 (app d, 1H, J=4.7 Hz), 7.90 (s, 1H), 7.88 (d, 1H, J=8.0 Hz), 7.83 (td, 1H, J=7.7, 1.8 Hz), 7.78-7.76 (m, 2H), 7.49-7.47 (m, 2H), 7.35-7.32 (m, 1H), 7.19 (d, 2H, J=8.1 Hz), 7.10 (d, 2H, J=8.1 Hz), 3.12 (t, 2H, J=7.3 Hz), 3.07 (s, 3H), 2.71 (t, 2H, J=7.7 Hz), 1.83-1.77 (m, 2H), 1.71-1.65 (m, 2H), 1.48-1.39 (m, 4H); $^{13}$C NMR (CDCl$_3$, 150 MHz) δ 188.3, 157.3, 153.0, 150.0, 146.0, 144.4, 140.4, 137.3, 133.8, 129.2, 126.9 (2C), 124.7, 124.2, 120.5, 44.5, 38.9, 35.6, 30.9, 28.8 (2C), 23.7; IR (film) λ$_{max}$ 2930, 2857, 1699, 1602, 1575, 1558, 1505, 1470, 1455, 1428, 1300, 1251, 1144, 1085, 963, 914, 786, 758, 697 cm$^{-1}$; ESI-TOF m/z 413.1529 (C$_{22}$H$_{24}$N$_2$O$_4$S+H$^+$ requires 413.1529).

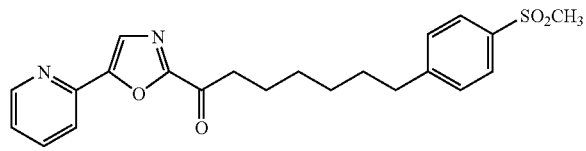

1-Oxo-1-[5-(2-pyridyl)oxazol-2-yl]-7-(4-(methylsulfonyl) phenyl)heptane (5 mm). The title compound was prepared from 1-oxo-1-[5-(2-pyridyl)oxazol-2-yl]-7-(4-(methylthio)phenyl)heptane (5v) following procedure H. PTLC (SiO$_2$, 40% EtOAc-hexanes) afforded 5 mm (20 mg, 0.049 mmol, 68%) as a white solid: $^1$H NMR (CDCl$_3$, 400 MHz) δ 8.68 (app d, 1H, J=4.7 Hz), 7.89-7.86 (m, 2H), 7.84 (d, 2H, J=8.2 Hz), 7.82 (td, 1H, J=7.7, 1.8 Hz), 7.37 (d, 2H, J=8.2 Hz), 7.35-7.31 (m, 1H), 3.12 (t, 2H, J=7.3 Hz), 3.05 (s, 3H), 2.71 (t, 2H, J=7.3 Hz), 1.82-1.75 (m, 2H), 1.70-1.63 (m, 2H), 1.48-1.39 (m, 4H); $^{13}$C NMR (CDCl$_3$, 100 MHz) δ 188.3, 157.3, 153.1, 150.0, 149.2, 146.1, 137.8, 137.2, 129.3, 127.4, 126.8, 124.2, 120.4, 44.5, 38.9, 35.7, 30.8, 28.8 (2C), 23.7; IR (film) ν$_{max}$ 2930, 2856, 1699, 1651, 1600, 1575, 1505, 1470, 1427, 1304, 1148, 1090, 962, 787 cm$^{-1}$; ESI-TOF m/z 413.1516 (C$_{22}$H$_{24}$N$_2$O$_4$S+ H$^+$ requires 413.1529).

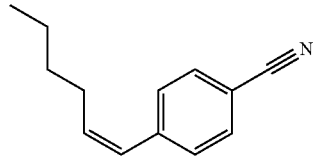

4-((Z)-Hex-1-enyl)benzonitrile (S16). A suspension of BrPh$_3$P(CH$_2$)$_4$CH$_3$ (4.69 g, 11.3 mmol, 1.6 equiv) in anhydrous THF (40 mL) at −78° C. was treated with n-BuLi (2.5 M in hexanes, 4.3 mL, 10.8 mmol, 1.5 equiv) and the mixture was stirred for 5 min. The reaction mixture was allowed to warm slowly at 25° C. and was then cooled to −78° C. A solution of 4-cyanobenzaldehyde (920 mg, 7.0 mmol, 1.0 equiv) in anhydrous THF (35 mL) was added dropwise over 1 h and the reaction was quenched with the addition of saturated aqueous NH$_4$Cl and extracted with EtOAc. The organic layer was dried over anhydrous Na$_2$SO$_4$, filtered and concentrated. Chromatography (SiO$_2$, 0-5% EtOAc-hexanes) afforded S16 (1.20 g, 92%) as a pale yellow oil: $^1$H NMR (CDCl$_3$, 400 MHz) δ 7.60 (d, 2H, J=8.3 Hz), 7.34 (d, 2H, J=8.0 Hz), 6.37 (d, 1H, J=13.2 Hz), 5.83-5.79 (m, 1H), 2.32-2.27 (m, 2H), 1.47-1.31 (m, 4H), 0.89 (t, 3H, J=7.4 Hz).

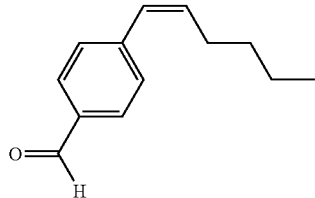

4-((Z)-Hex-1-enyl)benzaldehyde (S17). A solution of 4-((Z)-hex-1-enyl)benzonitrile (S16, 625 mg, 3.38 mmol) in anhydrous toluene (20 mL) at 0° C. was treated with DIBAL-H (1 M in toluene, 4.8 mL, 4.8 mmol, 1.4 equiv) and stirred for 15 min. The reaction mixture was quenched with the addition of aqueous 1 N HCl and extracted with EtOAc. The organic layer was dried over anhydrous Na$_2$SO$_4$, filtered and concentrated. Chromatography (SiO$_2$, 0-5% EtOAc-hexanes) afforded S17 (540 mg, 85%) as a pale yellow oil: $^1$H NMR (CDCl$_3$, 500 MHz) δ 10.0 (s, 1H), 7.85 (d, 2H, J=8.1 Hz), 7.43 (d, 2H, J=8.1 Hz), 6.44 (d, 1H, J=13.2 Hz), 5.96-5.80 (m, 1H), 2.38-2.33 (m, 2H), 1.51-1.33 (m, 4H), 0.90 (t, 3H, J=7.0 Hz).

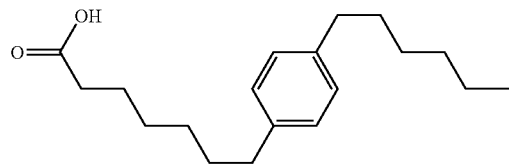

7-(4-Hexylphenyl)heptanoic acid (S18). A solution of 4-((Z)-hex-1-enyl)benzaldehyde (S17, 400 mg, 2.13 mmol) and BrPh$_3$P(CH$_2$)$_5$CO$_2$H (2.40 g, 5.25 mmol, 2.4 equiv) in anhydrous THF (10 mL) at −78° C. was treated with a suspension of t-BuOK (1.4 equiv) in anhydrous THF (8 mL). After 1 h, the reaction mixture was allowed to warm at 0° C. and was stirred for 16 h. The reaction was quenched with the addition of saturated aqueous NH$_4$Cl and extracted with EtOAc. The organic layer was dried over anhydrous Na$_2$SO$_4$, filtered and concentrated. Chromatography (SiO$_2$, 25-40% EtOAc-hexanes) afforded the diene (480 mg, 1.68 mmol, 79%). The material (400 mg, 1.40 mmol) was dissolved in EtOH (15 mL) and was treated with 10% Pd/C (120 mg). The suspension was purged with H$_2$ and was stirred overnight at 25° C. The reaction mixture was filtered through Celite and concentrated. Chromatography (SiO$_2$, 25% EtOAc-hexanes) afforded S18 (540 mg, 2.87 mmol, 85%) as a white solid: $^1$H NMR (CDCl$_3$, 500 MHz) δ 7.17 (s, 4H), 2.66 (t, 4H, J=7.7 Hz), 2.44 (t, 2H, J=7.3 Hz), 1.75-1.67 (m, 6H), 1.46-1.39 (m, 12H), 0.97 (t, 3H, J=7.0 Hz).

0-5% EtOAc-hexanes) afforded S19 (1.20 g, 6.48 mmol, 86%) as a pale yellow oil: $^1$H NMR (CDCl$_3$, 400 MHz) δ 7.61-7.34 (m, 4H), 6.37 (d, 1H, J=11.7 Hz), 5.83-5.76 (m, 1H), 2.32-2.26 (m, 2H), 1.48-1.32 (m, 4H), 0.90 (t, 3H, J=7.3 Hz).

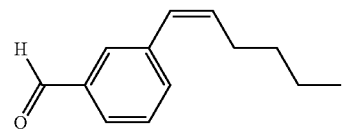

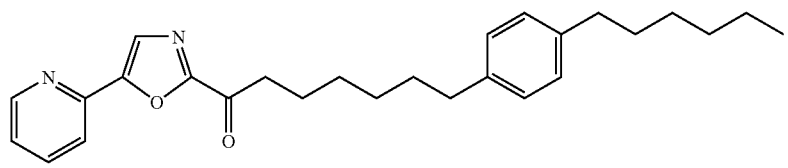

1-Oxo-1-[5-(2-pyridyl)oxazol-2-yl]-7-(4-hexylphenyl)heptane (5nn). The title compound was prepared from 5-(2-pyridyl)oxazole (6) and 7-(4-hexylphenyl)heptanoic acid (S18) using general procedure B. Column chromatography (SiO$_2$, 2.5×7 cm, 20-50% Et$_2$O-hexanes gradient) afforded 5nn (95 mg, 0.22 mmol, 61%) as a white solid: $^1$H NMR (CDCl$_3$, 400 MHz) δ 8.68 (app d, 1H, J=4.1 Hz), 7.90-7.86 (m, 2H), 7.82 (td, 1H, J=7.9, 1.7 Hz), 7.34-7.31 (m, 1H), 7.09 (s, 4H), 3.12 (t, 2H, J=7.2 Hz), 2.58 (t, 2H, J=7.3 Hz), 2.56 (t, 2H, J=7.3 Hz), 1.83-1.75 (m, 2H), 1.67-1.56 (m, 4H), 1.45-1.39 (m, 4H), 1.35-1.29 (m, 6H), 0.88 (t, 3H, J=6.6 Hz); $^{13}$C NMR (CDCl$_3$, 100 MHz) δ 188.5, 157.3, 153.1, 150.1, 146.2, 140.1, 139.8, 137.1, 128.2, 128.1, 126.9, 124.1, 120.4, 39.1, 35.5, 35.4, 31.7, 31.5, 31.3, 29.0 (2C), 23.9, 22.6, 14.1; IR (film) $v_{max}$ 2927, 2855, 1699, 1603, 1576, 1504, 1468, 1425, 1380, 1151, 1117, 1035, 989, 963, 784 cm$^{-1}$; ESI-TOF m/z 441.2510 (M+Na$^+$, C$_{27}$H$_{34}$N$_2$O$_2$ requires 441.2512).

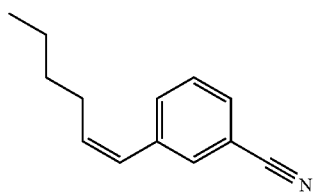

3-((Z)-Hex-1-enyl)benzonitrile (S19). The title compound was prepared from 3-cyanobenzaldehyde and BrPh$_3$P(CH$_2$)$_4$CH$_3$ following the procedure described for 4-((Z)-hex-1-enyl)benzonitrile (S16). Chromatography (SiO$_2$, 3-((Z)-Hex-1-enyl)benzaldehyde (S20). The title compound was prepared from 3-((Z)-hex-1-enyl)benzonitrile (S19) following the procedure described for 4-((Z)-hex-1-enyl)benzaldehyde (S17). Chromatography (SiO$_2$, 0-5% EtOAc-hexanes) afforded S20 (270 mg, 53%) as a pale yellow oil: $^1$H NMR (CDCl$_3$, 400 MHz) δ 10.0 (s, 1H), 7.78-7.74 (m, 2H), 7.55-7.48 (m, 2H), 6.45 (d, 1H, J=11.7 Hz), 5.82-5.75 (m, 1H), 2.37-2.31 (m, 2H), 1.50-1.33 (m, 4H), 0.90 (t, 3H, J=7.1 Hz).

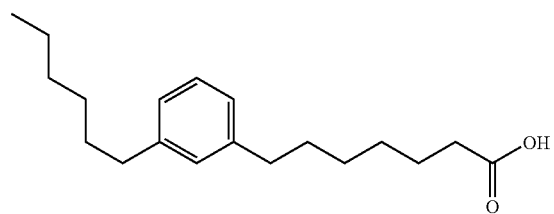

7-(3-Hexylphenyl)heptanoic acid (S21). The title compound was prepared from 3-((Z)-hex-1-enyl)benzaldehyde (S20) following the procedure described for 7-(4-hexylphenyl)heptanoic acid (S18). Chromatography (SiO$_2$, 0-5% EtOAc-hexanes) afforded S21 (300 mg, 78%) as a white solid: $^1$H NMR (CDCl$_3$, 500 MHz) δ 7.19 (t, 1H, J=7.6 Hz), 7.01-6.98 (m, 3H), 7.01-6.98 (m, 3H), 2.58 (t, 4H, J=7.7 Hz), 2.37 (t, 2H, J=7.4 Hz), 1.66-1.59 (m, 6H), 1.39-1.31 (m, 12H), 0.89 (t, 3H, J=7.0 Hz).

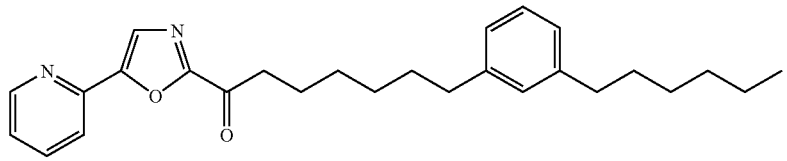

1-Oxo-1-[5-(2-pyridyl)oxazol-2-yl]-7-(3-hexylphenyl)heptane (5oo). The title compound was prepared from 5-(2-pyridyl)oxazole (6) and 7-(3-hexylphenyl)heptanoic acid (S21) using general procedure B. Column chromatography (SiO$_2$, 2.5×7 cm, 20-50% Et$_2$O-hexanes gradient) afforded 5oo (85 mg, 0.20 mmol, 51%) as a white solid: $^1$H NMR (CDCl$_3$, 500 MHz) δ 8.68 (app d, J=4.4 Hz, 1H), 7.90 (s, 1H), 7.88 (d, 1H, J=8.0 Hz), 7.82 (td, 1H, J=7.8, 1.8 Hz), 7.34-7.31 (m, 1H), 7.18 (t, 1H, J=7.9 Hz), 7.00-6.96 (m, 3H), 3.12 (t, 2H, J=7.3 Hz), 2.60-2.56 (m, 4H), 1.82-1.76 (m, 2H), 1.67-1.57 (m, 4H), 1.47-1.30 (m, 10H), 0.88 (t, 3H, J=6.4 Hz); $^{13}$C NMR (CDCl$_3$, 100 MHz) δ 188.5, 157.4, 153.1, 150.0, 146.2, 142.9, 142.6, 137.2, 128.5, 128.1, 127.0, 125.7, 125.6, 124.1, 120.4, 39.1, 36.0, 35.9, 31.7, 31.5, 31.3, 29.1, 29.0, 23.9, 22.6, 14.1; IR (film) ν$_{max}$ 2928, 2855, 1699, 1673, 1604, 1576, 1505, 1468, 1425, 1361, 1261, 1082, 1023, 785 cm$^{-1}$; ESI-TOF m/z 419.2695 (M+H$^+$, C$_{27}$H$_{34}$N$_2$O$_2$ requires 419.2693).

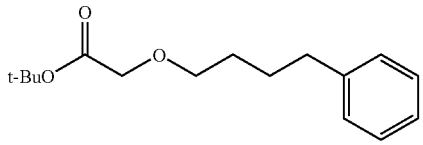

tert-Butyl 2-(4-phenylbutoxy)acetate (S52). A solution of 1-phenyl-4-butanol (900 mg, 6.0 mmol) in toluene (25 mL) was treated with tert-butyl 2-bromoacetate (2.7 mL, 18.3 mmol), tert-butylammonium bromide (100 mg, 0.27 mmol) and aqueous 50% NaOH (10 mL). After stirring at 25° C. for 30 h, the reaction mixture was quenched with aqueous 1 N HCl and extracted with EtOAc. The organic layer was dried over anhydrous Na$_2$SO$_4$, filtered and concentrated. Column chromatography (SiO$_2$, 4×6 cm, 0-2% EtOAc-hexanes gradient) afforded S52 (1.50 g, 5.68 mmol, 95%) as a yellow oil: $^1$H NMR (CDCl$_3$, 500 MHz) δ 7.29-7.26 (m, 2H), 7.20-7.16 (m, 3H), 3.95 (s, 2H), 3.54 (t, 2H, J=6.3 Hz), 2.65 (t, 2H, J=7.4 Hz), 1.75-1.65 (m, 4H), 1.49 (s, 3H).

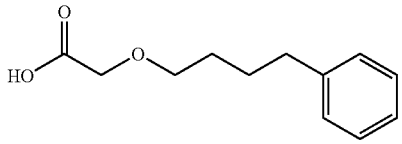

2-(4-Phenylbutoxy)acetic acid (S53). A solution of tert-butyl 2-(4-phenylbutoxy)acetate (S52, 1.40 g, 5.30 mmol) in anhydrous CH$_2$Cl$_2$ (40 mL) was treated with TFA (18 mL) and was stirred at 25° C. for 3 h. The reaction mixture was concentrated, treated with aqueous 1 N HCl and extracted with EtOAc. The organic layer was dried over anhydrous Na$_2$SO$_4$, filtered and concentrated. Column chromatography (SiO$_2$, 4×5 cm, 30% EtOAc-hexanes) afforded S53 (1.01 g, 4.86 mmol, 92%) as a white solid: $^1$H NMR (CDCl$_3$, 400 MHz) δ 7.30-7.26 (m, 2H), 7.19-7.16 (m, 3H), 4.12 (s, 2H), 3.58 (t, 2H, J=6.2 Hz), 2.65 (t, 2H, J=7.4 Hz), 1.75-1.66 (m, 4H); $^{13}$C NMR (CDCl$_3$, 125 MHz) δ 175.6, 142.1, 128.3, 128.2, 125.7, 71.8, 67.6, 35.5, 28.9, 27.6.

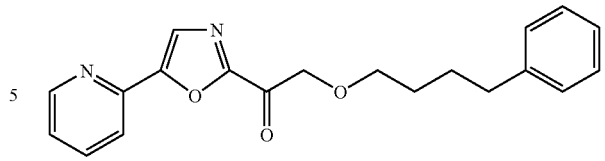

2-(4-Phenylbutoxy)-1-(5-(pyridin-2-yl)oxazol-2-yl)ethanone (12a). The title compound was prepared from 5-(2-pyridyl)oxazole (6) and 2-(4-phenylbutoxy)acetic acid (S53) following general procedure B. PTLC (SiO$_2$, 50% EtOAc-hexanes) afforded 12a (4 mg, 0.012 mmol, 1.2%) as a pale yellow oil: $^1$H NMR (CDCl$_3$, 400 MHz) δ 8.68 (d, 1H, J=4.4 Hz), 7.89-7.86 (m, 2H), 7.82 (td, 1H, J=7.8, 1.8 Hz), 7.34-7.31 (m, 2H), 7.22-7.18 (m, 5H), 4.90 (s, 2H), 3.65 (t, 2H, J=6.3 Hz), 2.66 (t, 2H, J=7.7 Hz), 1.77-1.69 (m, 4H); $^{13}$C NMR (CDCl$_3$, 150 MHz) δ 188.4, 157.3, 153.3, 150.1, 146.1, 137.2, 128.4, 128.3, 128.2, 126.8, 125.7, 124.3, 120.5, 73.1, 72.0, 35.6, 29.1, 27.8; IR (film) ν$_{max}$ 2925, 2859, 1712, 1603, 1573, 1502, 1469, 1426, 1282, 1150, 1020, 961, 784, 743, 700 cm$^{-1}$; ESI-TOF m/z 337.1550 (C$_{20}$H$_{20}$N$_2$O$_3$+H$^+$ requires 337.1547).

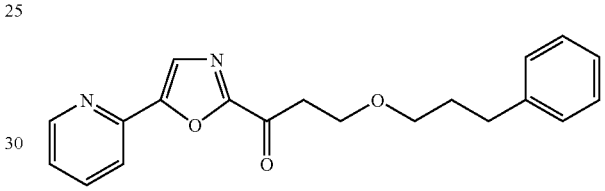

3-(3-Phenylpropoxy)-1-(5-(pyridin-2-yl)oxazol-2-yl)propan-1-one (12e). The title compound was prepared from 5-(2-pyridyl)oxazole (6) and 3-(3-phenylpropoxy)propanoic acid (Shaikh, A. A.; Thaker, K. Indian Journal of Chemistry 1967, 5, 585-586) using general procedure B. Column chromatography (SiO$_2$, 0-2% MeOH—CH$_2$Cl$_2$) followed by PTLC (1% MeOH—CH$_2$Cl$_2$) afforded 12e (65 mg, 17%) as a white solid: $^1$H NMR (400 MHz, CDCl$_3$) δ 8.57 (app d, J=4.8 Hz, 1H), 7.81 (s, 1H), 7.78-7.68 (m, 2H), 7.24-7.05 (m, 6H), 3.81 (t, J=6.4 Hz, 2H), 3.38 (t, J=6.4 Hz, 2H), 3.30 (t, J=6.4 Hz, 2H), 2.55 (t, J=6.6 Hz, 2H), 1.78 (quint, J=6.4 Hz, 2H); $^{13}$C NMR (100 MHz, CDCl$_3$) δ 186.2, 157.2, 153.3, 150.0, 146.1, 141.8, 137.0, 128.4, 128.2, 126.9, 125.6, 124.1, 120.3, 70.1, 65.4, 39.4, 32.1, 31.0; ESI-TOF m/z 337.1540 (C$_{20}$H$_{20}$N$_2$O$_3$+H$^+$ requires 337.1547).

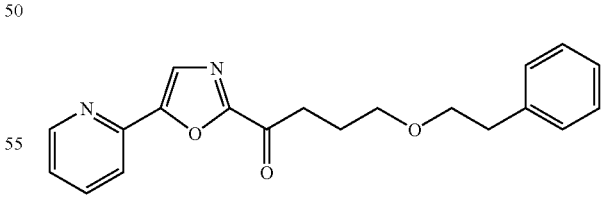

4-Phenethoxy-1-(5-(pyridin-2-yl)oxazol-2-yl)butan-1-one (12g). 4-Bromobutanoic acid (9.76 g, 58.4 mmol) and concentrated H$_2$SO$_4$ (3 drops) were dissolved in CH$_2$Cl$_2$ (20 mL) and the mixture was cooled to −78° C. Isobutylene was bubbled into the solution until the volume doubled. The reaction mixture was stirred for 3 days at room temperature before it was cooled to −78° C. and N$_2$ was bubbled into the reaction mixture to remove excess isobutylene. The reaction mixture was diluted with CH$_2$Cl$_2$ and washed with aqueous 2 N KOH and saturated aqueous NaCl, and concentrated to yield tert-butyl 4-bromobutanoate (4.13 g, 32%) which required no further purification. tert-Butyl 4-bromobutanoate (2.29 g, 10.2 mmol) was dissolved in acetone (40 mL) and NaI (3.08 g, 20.5 mmol) was added. The reaction mixture was warmed to reflux for 3 h under an Ar atmosphere. The acetone was removed in vacuo and the resulting residue was dissolved in EtOAc. The solution was washed with saturated aqueous NaCl, dried over $Na_2SO_4$ and concentrated to yield tert-butyl 4-iodobutanoate (2.29 g, 83%) which required no further purification. To a solution of tert-butyl 4-iodobutanoate (1.30 g, 4.82 mmol) and phenethyl alcohol (2.94 g, 24.1 mmol) in benzene (10 mL) was added aqueous 50% NaOH (6 mL) and $Bu_4HSO_4$ (1.64 g, 4.82 mmol). The reaction mixture was stirred vigorously at room temperature for 3 h. The reaction mixture was diluted with ether and water. The aqueous layer was extracted with ether and the combined organic layers were washed with saturated aqueous NaCl, dried over $Na_2SO_4$ and concentrated to yield the crude ester. Column chromatography (20% EtOAc-hexanes) afforded tert-butyl 4-phenethoxybutanoate (332 mg, 26%). tert-Butyl 4-phenethoxybutanoate (332 mg, 1.26 mmol) was dissolved in TFA (5 mL) and the reaction mixture was stirred at room temperature for 45 min. The solution was concentrated and the resulting residue was dissolved in ether and washed with aqueous 2 N KOH. The aqueous layer was acidified with concentrated HCl and extracted with ether. The combined organic layers were washed with saturated aqueous NaCl, dried over $Na_2SO_4$ and concentrated to yield the crude acid. Column chromatography (SiO$_2$, 10% EtOAc-hexanes) afforded 4-phenethoxybutanoic acid (210 mg, 80%). The title compound was prepared from 5-(2-pyridyl)oxazole (6) and 4-phenethoxybutanoic acid using general procedure B. PTLC (1% MeOH—CH$_2$Cl$_2$) afforded 12g (40 mg, 23%) as colorless oil: NMR (CDCl$_3$, 300 MHz) δ 8.67 (app d, J=4.8 Hz, 1H), 7.89 (s, 1H), 7.88-7.78 (m, 2H), 7.33-7.16 (m, 6H), 3.60 (t, J=7.2 Hz, 2H), 3.54 (t, J=6.0 Hz, 2H), 3.19 (t, J=7.2 Hz), 2.82 (t, J=7.2 Hz, 2H), 2.07 (quint, J=6.4 Hz, 2H); $^{13}$C NMR (CDCl$_3$, 75 MHz) δ 188.0, 157.4, 153.1, 150.1, 146.3, 138.9, 137.0, 128.8, 128.2, 126.8, 126.1, 124.0, 120.3, 71.7, 69.6, 36.2, 36.0, 24.2; ESI-TOF m/z 337.1542 (C$_{20}$H$_{20}$N$_2$O$_3$+H$^+$ requires 337.1547).

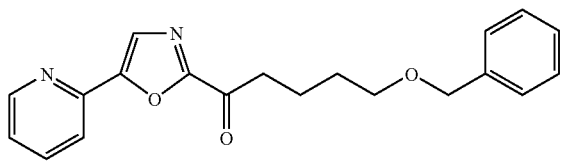

5-(Benzyloxy)-1-(5-(pyridin-2-yl)oxazol-2-yl)pentan-1-one (12i). The title compound was prepared from 5-(2-pyridyl)oxazole (6) and 5-(benzyloxy)pentanoic acid (Lermer, L. L.; Neeland, E. G.; et al. Can. J. Chem. 1992, 70, 1427-1445) using general procedure B. Column chromatography (SiO$_2$, 3×7 cm, 10-50% EtOAc-hexanes gradient) followed by PTLC (50% EtOAc-hexanes) afforded 12i (67 mg, 19%) as a pale white solid: $^1$H NMR (CDCl$_3$, 400 MHz) δ 8.66 (app d, J=4.4 Hz, 1H), 7.87 (s, 1H), 7.86-7.76 (m, 2H), 7.34-7.23 (m, 6H), 4.50 (s, 2H), 3.53 (t, J=6.4 Hz, 2H), 3.15 (t, J=7.6 Hz, 2H), 1.94-1.86 (m, 2H), 1.76-1.71 (m, 2H); $^{13}$C NMR (CDCl$_3$, 100 MHz) δ 188.1, 157.2, 153.1, 150.0, 146.2, 138.4, 137.0, 128.3, 127.5, 127.4, 126.8, 124.0, 120.3, 72.8, 69.8, 38.7, 29.0, 20.6; ESI-TOF m/z 337.1540 (C$_{20}$H$_{20}$N$_2$O$_3$+H$^+$ requires 337.1547).

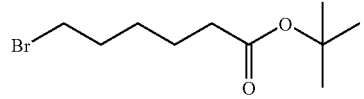

tert-Butyl 6-bromohexanoate (S54). 6-Bromohexanoic acid (6.0 g, 0.03 mmol) and concentrated H$_2$SO$_4$ (1 drop) was dissolved in a mixture of CHCl$_3$:1,4-dioxane (3:1, 30 mL) and the mixture was cooled to −78° C. Isobutylene was bubbled into the solution until the volume doubled. The reaction mixture was stirred for 30 days at room temperature before it was cooled to −78° C. and N$_2$ was bubbled into the reaction mixture to remove excess isobutylene. The reaction mixture was diluted with CH$_2$Cl$_2$ and washed with aqueous 2 N KOH and saturated aqueous NaCl, and concentrated to yield S54 (5.2 g, 68%) which required no further purification: $^1$H NMR (CDCl$_3$, 500 MHz) δ 3.41 (t, 2H, J=6.6 Hz), 2.23 (t, 2H, J=7.3 Hz), 1.90-1.85 (m, 2H), 1.65-1.59 (m, 2H), 1.50-1.45 (m, 11H).

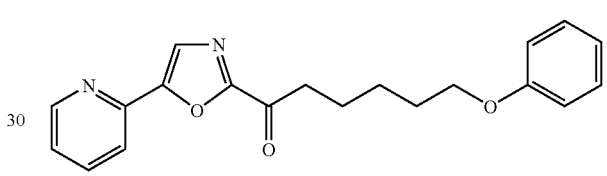

6-Phenoxy-1-(5-(pyridin-2-yl)oxazol-2-yl)hexan-1-one (12n). tert-Butyl 6-bromohexanoate (S54, 1.03 g, 4.09 mmol) was dissolved in acetone (30 mL) and NaI (1.23 g, 8.19 mmol) was added. The reaction mixture was warmed at reflux for 3 h under an Ar atmosphere. The acetone was removed in vacuo and the resulting residue was dissolved in EtOAc. The solution was washed with saturated aqueous NaCl, dried over Na$_2$SO$_4$ and concentrated to yield tert-butyl 6-iodohexanoate (1.16 g, 94%) which required no further purification. tert-Butyl 6-iodohexanoate (1.16 g, 3.86 mmol) and phenol (726 mg, 7.72 mmol) were dissolved in DMF (20 mL) and K$_2$CO$_3$ (2.67 g, 19.3 mmol) was added. The reaction mixture was stirred overnight at room temperature. The solvent was removed in vacuo and the resulting residue was dissolved in ether. The solution was washed with aqueous 2 N KOH and saturated aqueous NaCl, dried over Na$_2$SO$_4$ and concentrated to yield tert-butyl 6-phenoxyhexanoate (953 mg, 93%) as a light yellow crystalline solid that required no further purification. tert-Butyl 6-phenoxyhexanoate (871 mg, 3.30 mmol) was dissolved in TFA (10 mL) and the reaction mixture was stirred at room temperature for 45 min. The solution was concentrated and the resulting residue was dissolved in ether and washed with aqueous 2 N KOH. The aqueous layer was acidified with concentrated HCl and extracted with ether. The combined organic layers were washed with saturated aqueous NaCl, dried over Na$_2$SO$_4$ and concentrated to yield the crude acid. Column chromatography (SiO$_2$, 10-100% EtOAc-hexanes) afforded 6-phenoxyhexanoic acid (634 mg, 92%). The title compound was prepared from 5-(2-pyridyl)oxazole (6) and 6-phenoxyhexanoic acid using general procedure B. Column chromatography (SiO$_2$, 10-50% EtOAc-hexanes gradient) followed by PTLC (1% MeOH—CH$_2$Cl$_2$) afforded 12n (93 mg, 27%)

as colorless oil: $^1$H NMR (CDCl$_3$, 400 MHz) δ 8.57 (app d, J=4.8 Hz, 1H), 7.79 (s, 1H), 7.60 (d, J=7.8 Hz, 1H), 7.71 (dd, J=7.4, 1.2 Hz, 1H), 7.23-7.16 (m, 3H), 6.85-6.79 (m, 3H), 3.88 (t, J=6.4 Hz, 2H), 3.07 (t, J=7.6 Hz, 2H), 1.81-1.72 (m, 4H), 1.54-1.47 (m, 2H); $^{13}$C NMR (CDCl$_3$, 100 MHz) δ 188.1, 158.9, 157.2, 153.2, 150.0, 146.1, 137.00, 129.3, 126.8, 124.0, 120.4, 120.3, 114.3, 67.3, 38.9, 28.9, 25.6, 23.6; ESI-TOF m/z 337.1540 (C$_{20}$H$_{20}$N$_2$O$_3$+H$^+$ requires 337.1547).

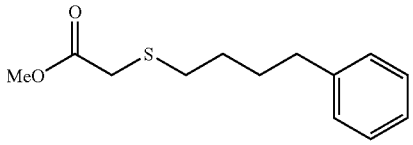

Methyl 2-(4-phenylbutylthio)acetate (S55). A solution of 1-phenyl-4-butanol (1.05 g, 7.0 mmol) in anhydrous CH$_2$Cl$_2$ (20 mL) was treated with CBr$_4$ (2.55 g, 7.6 mmol) and was stirred for 5 min at 25° C. PPh$_3$ (2.02 g, 7.7 mmol) in anhydrous CH$_2$Cl$_2$ (6 mL) was added dropwise and was stirred for 1 h at 25° C. The reaction mixture was quenched with saturated aqueous NaHCO$_3$ and extracted with CH$_2$Cl$_2$. The organic layer was dried over anhydrous Na$_2$SO$_4$, filtered and concentrated. Column chromatography (SiO$_2$, 5.5×9 cm, 3% EtOAc-hexanes) afforded 1-phenyl-4-bromobutane (1.41 g, 6.65 mmol, 95%) as a pale yellow oil. A solution of 1-phenyl-4-bromobutane (1.30 g, 6.13 mmol) in a mixture of acetone/DMSO (4/1, 20 mL) was treated with K$_2$CO$_3$ (2.57 g, 18.6 mmol) and methyl thioglycolate (0.66 mL, 7.4 mmol). After stirring for 30 h at 25° C., the reaction mixture was quenched with an aqueous 1 N HCl solution and extracted with EtOAc. The organic layer was dried over anhydrous Na$_2$SO$_4$, filtered and concentrated. Column chromatography (SiO$_2$, 4×10 cm, 25% EtOAc-hexanes) afforded S55 (1.31 g, 5.50 mmol, 90%) as a yellow oil: $^1$H NMR (CDCl$_3$, 500 MHz) δ 7.37-7.34 (m, 2H), 7.28-7.24 (m, 3H), 3.81 (s, 3H), 3.29 (s, 2H), 2.70-2.75 (m, 4H), 1.85-1.69 (m, 4H).

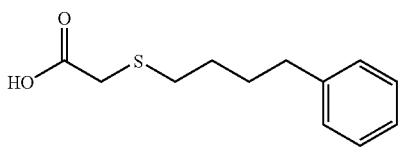

2-(4-Phenylbutylthio)acetic acid (S56). A solution of methyl 2-(4-phenylbutylthio)acetate (S55, 715 mg, 3.0 mmol) in a mixture of THF/MeOH (1/1, 6 mL) was treated with aqueous 1 N NaOH (2 mL) and was stirred overnight at 25° C. The reaction mixture was concentrated, treated with aqueous 1 N HCl and extracted with CH$_2$Cl$_2$. The organic layer was dried over anhydrous Na$_2$SO$_4$, filtered and concentrated to afford S56 (630 mg, 2.81 mmol, 94%) as a pale yellow oil: $^1$H NMR (CDCl$_3$, 500 MHz) δ 7.30-7.28 (m, 2H), 7.21-7.18 (m, 3H), 3.24 (s, 2H), 2.70 (t, 2H, J=7.7 Hz), 1.78-1.65 (m, 4H).

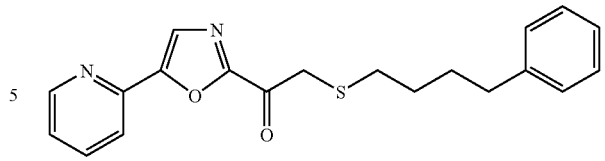

2-(4-Phenylbutylthio)-1-(5-(pyridin-2-yl)oxazol-2-yl)etha-none (12b). The title compound was prepared from 5-(2-pyridyl)oxazole (6) and 2-(4-phenylbutylthio)acetic acid (S56) using general procedure B. PTLC (SiO$_2$, 40% EtOAc-hexanes) afforded 12b (10 mg, 0.028 mmol, 6%) as a tan oil: $^1$H NMR (CDCl$_3$, 500 MHz) δ 8.73 (d, 1H, J=3.7 Hz), 8.34 (d, 1H, J=9.2 Hz), 7.85-7.81 (m, 1H), 7.37-7.34 (m, 1H), 7.19-7.10 (m, 4H), 4.82 (s, 2H), 3.29 (t, 2H, J=8.8 Hz), 2.60 (t, 2H, J=8.8 Hz), 1.76-1.62 (m, 4H); $^{13}$C NMR (CDCl$_3$, 125 MHz) δ 169.7, 159.2, 152.8, 150.2, 149.8, 141.9, 136.4, 128.3 (2C), 127.8, 125.8, 124.8, 124.6, 47.9, 35.2, 31.6, 30.1, 29.8; ESI-TOF m/z 353.1322 (C$_{20}$H$_{20}$N$_2$O$_2$S+H$^+$ requires 353.1318).

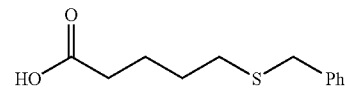

5-(Benzylthio)pentanoic acid (S57). A solution of α-mercaptotoluene (9.3 g, 75 mmol) and 5-bromovaleric acid (4.5 g, 24.8 mmol) in 30 mL of absolute EtOH was treated with a 4 N aqueous solution of NaOH (30 mL) and was warmed at reflux for 44 h. The mixture was concentrated, treated with 15 mL of aqueous 4 N NaOH and 50 mL of aqueous 1 N K$_3$FeCN$_6$. After stirring for 30 min at 25° C., the mixture was extracted with Et$_2$O. The aqueous solution was treated with aqueous 6 N HCl and stirred for 10 min. The precipitate was collected by filtration, washed with H$_2$O and dried. The solid was recrystallized in hexane to give S57 as white crystals (1.72 g, 7.7 mmol). The mother liquor and washings were concentrated and column chromatography (SiO$_2$, 4.5×10 cm, 10-25% EtOAc-hexanes gradient) afforded additional amounts of S57 (1.17 g, 5.2 mmol, 52% combined yields) as a pale yellow solid: $^1$H NMR (CDCl$_3$, 400 MHz) δ 7.32-7.30 (m, 4H), 7.26-7.23 (m, 1H), 3.71 (s, 2H), 2.43 (t, 2H, J=7.3 Hz), 2.34 (t, 2H, J=7.3 Hz), 1.74-1.57 (m, 4H); $^{13}$C NMR (CDCl$_3$, 100 MHz) δ 179.8, 138.4, 128.8 (2C), 128.4 (2C), 126.9, 36.2, 33.5, 30.7, 28.4, 23.7.

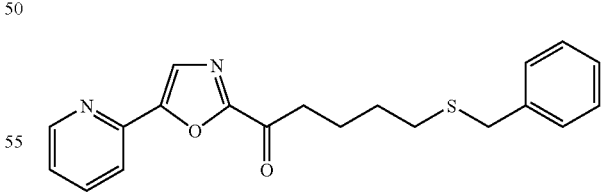

5-(Benzylthio)-1-(5-(pyridin-2-yl)oxazol-2-yl)pentan-1-one (12k). The title compound was prepared from 5-(2-pyridyl)oxazole (6) and 5-(benzylthio)pentanoic acid (S57) using general procedure B. Column chromatography (SiO$_2$, 3.5×8 cm, 25% EtOAc-hexanes) followed by PTLC (25% acetone-petroleum ether) afforded 12k (62 mg, 0.18 mmol, 9%) as a pale yellow solid: $^1$H NMR (CDCl$_3$, 400 MHz) δ 8.68 (app d, 1H, J=4.4 Hz), 7.89-7.86 (m, 2H), 7.89-7.86 (m, 2H), 7.82 (td, 1H, J=7.7, 1.8 Hz), 7.34-7.30 (m, 5H), 7.25-7.22 (m, 1H), 3.72 (s, 2H), 3.11 (t, 2H, J=7.3 Hz), 2.47 (t, 2H, J=7.3 Hz), 1.89-1.81 (m, 2H), 1.71-1.64 (m, 2H); $^{13}$C NMR (CDCl$_3$, 100 MHz) δ 187.8, 157.1, 153.1, 150.0, 146.1, 138.3, 137.0, 128.7 (2C), 128.3 (2C), 126.8, 126.7, 124.0, 120.3, 38.4, 36.1, 30.7, 28.4, 22.9; IR (film) $v_{max}$ 3059, 3027, 2925, 2856, 1791, 1703, 1694, 1602, 1575, 1504, 1469, 1454, 1425, 1383, 1283, 1238, 1152, 1118, 1072, 1018, 990, 962, 851, 784, 702 cm$^{-1}$; ESI-TOF m/z 353.1319 (C$_{20}$H$_{20}$N$_2$O$_2$S+H$^+$ requires 353.1318).

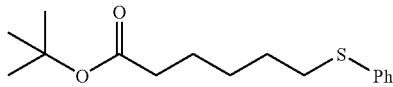

tert-Butyl 6-(phenylthio)hexanoate (S58). A solution of thiophenol (700 µL, 6.8 mmol) in anhydrous benzene (20 mL) was treated with DBU (920 µL, 6.2 mmol). After 5 min, Cert-butyl 6-bromohexanoate (S54, 1.5 g, 6.0 mmol) was added and the reaction mixture was stirred overnight at 25° C. The suspension was filtered through Celite and concentrated. The crude material was washed with aqueous 2 N KOH and extracted with EtOAc. The organic layer was dried over Na$_2$SO$_4$, filtered and concentrated. Column chromatography (SiO$_2$, 10×4.5 cm, 5% EtOAc-hexanes) afforded S58 (1.62 g, 5.8 mmol, 96%) as a colorless oil: $^1$H NMR (CDCl$_3$, 400 MHz) δ 7.34-7.26 (m, 4H), 7.19-7.14 (m, 1H), 2.92 (t, 2H, J=7.3 Hz), 2.21 (t, 2H, J=7.5 Hz), 1.71-1.57 (m, 4H), 1.50-1.45 (m, 2H), 1.44 (s, 9H).

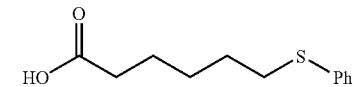

6-(Phenylthio)hexanoic acid (S59). A solution of tert-butyl 6-(phenylthio)hexanoate (S58, 1.16 g, 4.1 mmol) in 3 mL of anhydrous CH$_2$Cl$_2$ was treated with TFA (2 mL). After stirring for 2 h at 25° C., the reaction mixture was treated with a saturated aqueous NaCl. The organic layer was extracted with CH$_2$Cl$_2$, dried over Na$_2$SO$_4$, filtered and concentrated to afford S59 (870 mg, 3.9 mmol, 94%) which required no further purification: $^1$H NMR (CDCl$_3$, 400 MHz) δ 7.34-7.28 (m, 4H), 7.20-7.18 (m, 1H), 2.93 (t, 2H, J=7.2 Hz), 2.37 (t, 2H, J=7.4 Hz), 1.72-1.62 (m, 4H), 1.54-1.47 (m, 2H); $^{13}$C NMR (CDCl$_3$, 100 MHz) δ 179.8, 136.6, 129.0 (2C), 128.8 (2C), 125.8, 33.8, 33.4, 28.7, 28.1, 24.1.

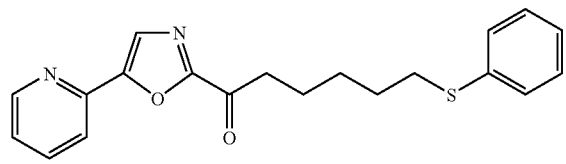

6-(Phenylthio)-1-(5-(pyridin-2-yl)oxazol-2-yl)hexan-1-one (12p). The title compound was prepared from 5-(2-pyridyl) oxazole (6) and 6-(phenylthio)hexanoic acid (S59) using general procedure B. Column chromatography (SiO$_2$, 4.5×9 cm, 15-20% EtOAc-hexanes gradient) afforded 12p (182 mg, 0.52 mmol, 22%) as a white solid: $^1$H NMR (CDCl$_3$, 400 MHz) δ 8.68-8.66 (m, 1H), 7.88-7.86 (m, 2H), 7.82 (td, 1H, J=7.7, 1.8 Hz), 7.34-7.25 (m, 5H), 7.19-

7.14 (m, 1H), 3.12 (t, 2H, J=7.3 Hz), 2.94 (t, 2H, J=7.2 Hz), 1.85-1.77 (m, 2H), 1.76-1.68 (m, 2H), 1.59-1.51 (m, 2H); $^{13}$C NMR (CDCl$_3$, 100 MHz) δ 188.1, 157.2, 153.3, 150.1, 146.2, 137.1, 136.6, 128.9 (2C), 128.8 (2C), 126.8, 125.7, 124.1, 120.3, 38.8, 33.2, 28.8, 28.2, 23.4; IR (film) $v_{max}$ 3055, 2931, 2858, 1699, 1602, 1575, 1504, 1480, 1425, 1382, 1283, 1235, 1152, 1118, 1085, 1025, 990, 962, 934, 784, 739, 691; ESI-TOF m/z 353.1321 (C$_{20}$H$_{20}$N$_2$O$_2$S+H$^+$ requires 353.1318).

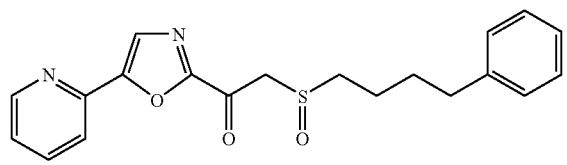

2-(4-Phenylbutylsulfinyl)-1-(5-(pyridin-2-yl)oxazol-2-yl) ethanone (12c). Oxidation of 2-(4-phenylbutylthio)-1-(5-(pyridin-2-yl)oxazol-2-yl)ethanone (12b) with m-CPBA (1.0 equiv) using general procedure M provided 2-(4-phenylbutylsulfonyl)-1-(5-(pyridin-2-yl)oxazol-2-yl)ethanone (12c, 3 mg, 25%) and 12d (4 mg, 34%) as a white solid: $^1$H NMR (CDCl$_3$, 600 MHz) δ 8.68 (app d, J=4.2 Hz, 1H), 7.95 (s, 1H), 7.88 (d, J=7.8 Hz, 1H), 7.84 (dt, J=7.5, 1.2 Hz, 1H), 7.35 (app dd, J=6.6, 5.4 Hz, 1H), 7.29-7.26 (m, 2H), 7.20-7.17 (m, 3H), 4.47 (q, J=13.2 Hz, 2H), 3.01-2.91 (m, 2H), 2.69 (t, J=7.8 Hz, 2H), 1.92-1.77 (m, 4H); $^{13}$C NMR (CDCl$_3$, 100 MHz) δ 178.9, 157.9, 157.0, 150.2, 145.7, 141.4, 137.2, 128.4, 128.3, 127.6, 125.9, 124.5, 120.7, 59.3, 53.1, 35.3, 30.4, 22.0; ESI-TOF m/z 369.1261 (C$_{20}$H$_{20}$N$_2$O$_3$S+H$^+$ requires 369.1267).

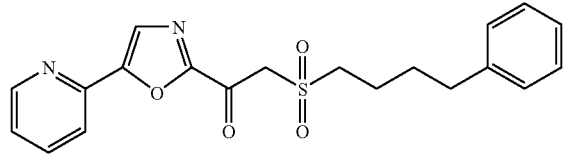

2-(4-Phenylbutylsulfonyl)-1-(5-(pyridin-2-yl)oxazol-2-yl) ethanone (12d). Oxidation of 2-(4-phenylbutylthio)-1-(5-(pyridin-2-yl)oxazol-2-yl)ethanone (12b) with m-CPBA (1.0 equiv) using general procedure M provided 12c (3 mg, 25%) and 2-(4-phenylbutylsulfinyl)-1-(5-(pyridin-2-yl) oxazol-2-yl)ethanone (12d, 4 mg, 34%) as a white solid: $^1$H NMR (CDCl$_3$, 600 MHz) δ 8.70 (app d, J=3.6 Hz, 1H), 7.98 (s, 1H), 7.88, (d, J=7.8 Hz, 1H), 7.85 (t, J=7.8 Hz, 1H), 7.37 (app t, J=5.4 Hz, 1H), 7.30-7.26 (m, 2H), 7.21-7.18 (m, 3H), 4.77 (s, 2H), 3.31 (t, J=7.8 Hz, 2H), 2.69 (t, J=7.2 Hz, 2H), 1.99-1.94 (m, 2H), 1.85-1.80 (m, 2H); ESI-TOF m/z 385.1208 (C$_{20}$H$_{20}$N$_2$O$_4$S+H$^+$ requires 385.1216).

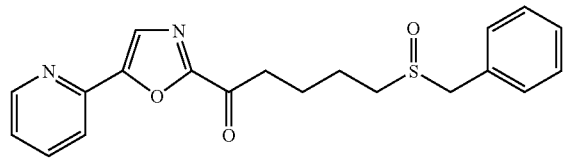

5-(Benzylsulfinyl)-1-(5-(pyridin-2-yl)oxazol-2-yl)pentan-1-one (12l). Oxidation of 5-(benzylthio)-1-(5-(pyridin-2-yl)

oxazol-2-yl)pentan-1-one (12k) with m-CPBA (1.0 equiv) using general procedure M provided 5-(Benzylsulfinyl)-1-(5-(pyridin-2-yl)oxazol-2-yl)pentan-1-one (12l, 10 mg, 45%) and 12m (10 mg, 48%) as a white solid: $^1$H NMR (CDCl$_3$, 400 MHz) δ 8.68-8.66 (m, 1H), 7.88-7.86 (m, 2H), 7.82 (td, 1H, J=7.7, 1.6 Hz), 7.41-7.28 (m, 6H), 4.05 (d, 1H, J=12.9 Hz), 3.96 (d, 1H, J=12.9 Hz), 3.16 (app t, 2H, J=6.6 Hz), 2.63 (app t, 2H, J=7.0 Hz), 1.95-1.84 (m, 4H); IR (film) $v_{max}$ 3057, 2922, 2852, 1704, 1694, 1603, 1575, 1505, 1470, 1455, 1426, 1386, 1284, 1153, 1119, 1074, 1028, 962, 936, 786, 739, 700 cm$^{-1}$; ESI-TOF m/z 369.1268 (C$_{20}$H$_{20}$N$_2$O$_3$S+H$^+$ requires 369.1267).

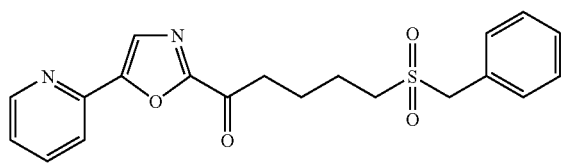

5-(Benzylsulfonyl)-1-(5-(pyridin-2-yl)oxazol-2-yl)pentan-1-one (12m). Oxidation of 5-(benzylthio)-1-(5-(pyridin-2-yl)oxazol-2-yl)pentan-1-one (12k) with m-CPBA (1.5 equiv) using the general procedure M provided 12l (7 mg, 27%) and 5-(benzylsulfonyl)-1-(5-(pyridin-2-yl)oxazol-2-yl)pentan-1-one (12m, 19 mg, 72%) as a white solid: $^1$H NMR (CDCl$_3$, 400 MHz) δ 8.69-8.66 (m, 1H), 7.88-7.85 (m, 2H), 7.82 (td, 1H, J=7.7, 1.8 Hz), 7.43-7.39 (m, 5H), 7.35-7.31 (m, 1H), 4.24 (s, 2H), 3.14 (t, 2H, J=6.7 Hz), 2.89 (t, 2H, J=7.5 Hz), 1.96-1.85 (m, 4H); $^{13}$C NMR (CDCl$_3$, 100 MHz) δ 187.2, 157.0, 153.4, 150.1, 146.1, 137.1, 130.5 (2C), 129.1 (2C), 129.0, 128.0, 126.9, 124.2, 120.4, 59.5, 50.6, 38.1, 22.5, 21.3; IR (film) $v_{max}$ 2933, 1699, 1601, 1575, 1505, 1469, 1456, 1426, 1282, 1118, 1029, 961, 934, 784, 739, 696 cm$^{-1}$; ESI-TOF m/z 385.1211 (C$_{20}$H$_{20}$N$_2$O$_4$S+H$^+$ requires 385.1216).

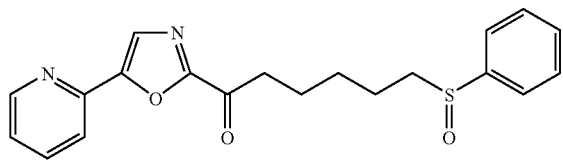

6-(Phenylsulfinyl)-1-(5-(pyridin-2-yl)oxazol-2-yl)hexan-1-one (12q). Oxidation of 6-(phenylthio)-1-(5-(pyridin-2-yl)oxazol-2-yl)hexan-1-one (12p) with m-CPBA (1.0 equiv) using general procedure M provided 6-(phenylsulfinyl)-1-(5-(pyridin-2-yl)oxazol-2-yl)hexan-1-one (12q, 10 mg, 26%) and 12r (27 mg, 73%) as a pale yellow oil: $^1$H NMR (CDCl$_3$, 400 MHz) δ 8.65 (app d, 1H, J=4.7 Hz), 7.86-7.82 (m, 2H), 7.80 (td, 1H, J=7.7, 1.7 Hz), 7.62-7.59 (m, 2H), 7.53-7.46 (m, 3H), 7.33-7.29 (m, 1H), 3.10 (t, 2H, J=7.1 Hz), 2.81 (t, 2H, J=7.5 Hz), 1.86-1.45 (m, 6H); $^{13}$C NMR (CDCl$_3$, 100 MHz) δ 187.9, 157.1, 153.3, 150.1, 146.1, 143.7, 137.1, 130.9, 129.2 (2C), 126.8, 124.1, 123.9 (2C), 120.3, 56.8, 38.6, 28.0, 23.3, 21.8; IR (film) $\mu_{max}$ 3057, 2938, 2865, 1704, 1694, 1602, 1575, 1505, 1471, 1427, 1284, 1154, 1087, 1030, 962, 933, 787, 744, 692 cm$^{-1}$; ESI-TOF m/z 369.1271 (C$_{20}$H$_{20}$N$_2$O$_3$S+H$^+$ requires 369.1267).

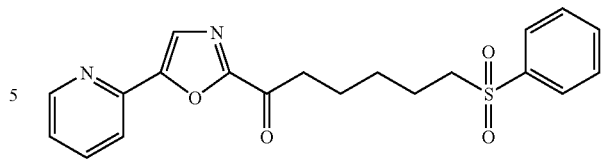

6-(Phenylthio)-1-(5-(pyridin-2-yl)oxazol-2-yl)hexan-1-one (12r). Oxidation of 6-(phenylthio)-1-(5-(pyridin-2-yl)oxazol-2-yl)hexan-1-one (12p) with m-CPBA (1.5 equiv) using general procedure M provided 12q (8 mg, 20%) and 6-(phenylthio)-1-(5-(pyridin-2-yl)oxazol-2-yl)hexan-1-one (12r, 31 mg, 79%) as a white solid: $^1$H NMR (CDCl$_3$, 400 MHz) δ 8.67-8.65 (m, 1H), 7.92-7.89 (m, 2H), 7.86-7.83 (m, 2H), 7.80 (td, 1H, J=7.7, 1.7 Hz), 7.67-7.63 (m, 1H), 7.59-7.54 (m, 2H), 7.33-7.30 (m, 1H), 3.13-3.06 (m, 4H), 1.82-1.71 (m, 4H), 1.52-1.44 (m, 2H); $^{13}$C NMR (CDCl$_3$, 100 MHz) δ 187.7, 157.1, 153.3, 150.1, 146.1, 139.0, 137.1, 133.7, 129.3 (2C), 128.0 (2C), 126.8, 124.2, 120.4, 56.0, 38.5, 27.7, 23.2, 22.5; IR (film) $v_{max}$ 3062, 2937, 2870, 1699, 1603, 1575, 1505, 1470, 1426, 1385, 1303, 1148, 1086, 1026, 963, 914, 786, 729, 690 cm$^{-1}$; ESI-TOF m/z 385.1221 (C$_{20}$H$_{20}$N$_2$O$_4$S+H$^+$ requires 385.1216).

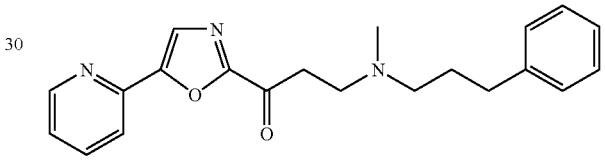

3-(Methyl(3-phenylpropyl)amino)-1-(5-(pyridin-2-yl)oxazol-2-yl)propan-1-one (12f). 1-(5-(Pyridin-2-yl)oxazol-2-yl)prop-2-en-1-one was prepared from 5-(pyridin-2-yl)oxazole (6) and 3-bromopropionyl chloride using general procedure B. 1-(5-(Pyridin-2-yl)oxazol-2-yl)prop-2-en-1-one (34 mg, 0.17 mmol) was dissolved in anhydrous CH$_2$Cl$_2$ (0.4 mL) under Ar and N-methyl-3-phenylpropylamine (38 mg, 0.255 mmol) was added dropwise. After 20 min, the reaction mixture was loaded onto a PTLC plate and eluted with 3% Et$_3$N in EtOAc. The crude product was subjected to further PTLC (1$^{st}$, 1% MeOH—CH$_2$Cl$_2$; 2$^{nd}$, 3% Et$_3$N-EtOAc) to yield 12f (4 mg, 7%) as a colorless oil: $^1$H NMR (CDCl$_3$, 500 MHz) δ 8.67 (ddd, J=5.0, 1.5, 1.0 Hz, 1H), 7.89 (s, 1H), 7.87-7.78 (m, 2H), 7.32 (ddd, J=7.4, 4.8, 1.5 Hz, 1H), 7.26-7.23 (m, 2H), 7.20-7.14 (m, 3H), 3.28 (t, J=7.0 Hz, 2H), 2.94 (t, J=7.0 Hz, 2H), 2.59 (t, J=7.5 Hz, 2H), 2.44 (t, J=7.0 Hz, 2H), 2.30 (s, 3H), 1.76-1.82 (m, 2H); $^{13}$C NMR (CDCl$_3$, 100 MHz) δ 188.4, 158.2, 157.3, 150.1, 146.3, 142.2, 137.1, 128.4, 128.3, 126.9, 125.7, 124.1, 120.4, 56.8, 52.3, 41.9, 36.8, 33.5, 28.9; ESI-TOF m/z 350.1860 (C$_{21}$H$_{23}$N$_3$O$_2$+H$^+$ requires 350.1863).

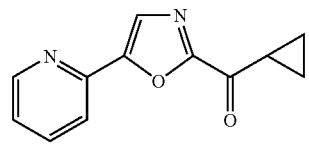

Cyclopropyl(5-(pyridin-2-yl)oxazol-2-yl)methanone (14d). The title compound was prepared from 5-(2-pyridyl)oxazole (6) and 4-bromobutyryl chloride following general procedure B. PTLC (50% hexanes-EtOAc) afforded 14d (20 mg, 8%) as a colorless oil: $^1$H NMR (CDCl$_3$, 500 MHz) δ 8.67 (ddd, J=5.0, 1.8, 0.5 Hz, 1H), 7.91 (s, 1H), 7.87 (app d, J=8.0 Hz, 1H), 7.81 (dt, J=7.8, 1.5 Hz, 1H), 7.31 (ddd, J=7.5, 5.0, 1.0 Hz, 1H), 3.16-3.11 (m, 1H), 1.38-1.35 (m, 2H), 1.21-1.17 (m, 2H); $^{13}$C NMR (CDCl$_3$, 125 MHz) δ 188.1, 157.9, 153.2, 150.1, 146.4, 137.1, 127.0, 124.1, 120.4, 18.3, 13.1; ESI-TOF m/z 215.0814 (C$_{12}$H$_{10}$N$_2$O$_2$+H$^+$ requires 215.0815).

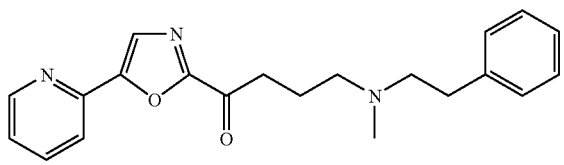

4-(Methyl(phenethyl)amino)-1-(5-(pyridin-2-yl)oxazol-2-yl)butan-1-one (12h). Cyclopropyl ketone 14d (24 mg, 0.112 mmol) was dissolved in anhydrous CH$_2$Cl$_2$ (0.4 mL) under Ar and N-methylphenethylamine (76 mg, 0.56 mmol, 5.0 equiv) was added. The mixture was cooled to 0° C. and TiCl$_4$ (1.0 M solution in CH$_2$Cl$_2$, 62 µL, 0.55 equiv) was added dropwise. The reaction mixture was allowed to warm slowly to room temperature and stirred for 4 h. The reaction mixture was diluted with CH$_2$Cl$_2$ and washed with aqueous 0.05 N NaOH and water. The organic phase was dried over anhydrous Na$_2$SO$_4$ and concentrated. Two successive PTLC purifications (1$^{st}$, 3% Et$_3$N-EtOAc; 2$^{nd}$, 50% hexanes-EtOAc) afforded 12h (11 mg, 28%) as light yellow oil: $^1$H NMR (CDCl$_3$, 400 MHz) δ 8.67 (ddd, J=4.8, 1.6, 1.2 Hz, 1H), 7.88 (s, 1H), 7.86 (dt J=7.6, 0.8 Hz, 1H), 7.80 (dt, J=7.4, 1.6 Hz, 1H), 7.31 (ddd, J=7.4, 4.8, 1.6 Hz, 1H), 7.25-7.21 (m, 2H), 7.17-7.13 (m, 3H), 3.08 (t, J=6.8 Hz, 2H), 2.68-2.61 (m, 2H), 2.58-2.47 (m, 4H), 2.21 (s, 3H), 2.06-1.99 (m, 2H); $^{13}$C NMR (CDCl$_3$, 150 MHz) δ 187.3, 157.9, 152.9, 150.1, 146.4, 140.3, 137.1, 128.7, 128.3, 126.7, 125.9, 124.0, 120.3, 59.1, 56.5, 41.2, 33.2, 29.7; ESI-TOF m/z 350.1863 (C$_{21}$H$_{23}$N$_3$O$_2$+H$^+$ requires 350.1863).

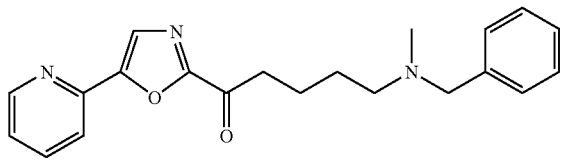

5-(Benzyl(methyl)amino)-1-(5-(pyridin-2-yl)oxazol-2-yl)pentan-1-one (12j). 5-Bromo-1-(5-(pyridin-2-yl)oxazol-2-yl)pentan-1-one was prepared from 5-(2-pyridyl)-oxazole (6) and 5-bromopentanoyl chloride using general procedure B. Column chromatography (SiO$_2$, 10-70% EtOAc-hexanes) afforded 5-bromo-1-(5-(pyridin-2-yl)oxazol-2-yl)pentan-1-one (339 mg, 31%) as a colorless oil. 5-Bromo-1-(5-(pyridin-2-yl)oxazol-2-yl)pentan-1-one (32 mg, 0.104 mmol) and N-methyl benzylamine (11 mg, 0.104 mmol) were dissolved in 2-butanone (0.34 mL) under Ar and K$_2$CO$_3$ (43 mg, 0.311 mmol) was added. The mixture was stirred overnight at room temperature and then diluted with H$_2$O and extracted with EtOAc. The organic phase was dried over anhydrous Na$_2$SO$_4$ and concentrated. PTLC (3% Et$_3$N-EtOAc) afforded a slightly impure product which was repurified on a second plate (50% hexanes-EtOAc) to yield 12j (16 mg, 44%): $^1$H NMR (CDCl$_3$, 400 MHz) δ 8.67 (ddd, J=4.8, 1.6, 0.8 Hz, 1H), 7.88 (s, 1H), 7.86 (t, J=1.2 Hz, 1H), 7.81 (dt, J=7.4, 2.0 Hz, 1H), 7.26-7.20 (m, 1H), 7.34-7.27 (m, 5H) 3.48 (s, 2H), 3.13 (t, J=7.6 Hz, 2H), 7.43 (t, J=7.2 Hz, 2H), 2.19 (s, 3H), 2.86-2.79 (m, 2H), 1.67-1.59 (m, 2H); $^{13}$C NMR (CDCl$_3$, 150 MHz) δ 188.3, 157.3, 153.2, 150.1, 146.3, 139.0, 137.1, 129.0, 128.2, 126.9, 126.8, 124.1, 120.4, 62.2, 56.8, 42.1, 38.9, 26.7, 21.7; ESI-TOF m/z 350.1869 (C$_{21}$H$_{23}$N$_3$O$_2$+H$^+$ requires 350.1863).

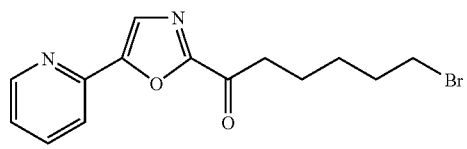

6-Bromo-1-(5-(pyridin-2-yl)oxazol-2-yl)hexan-1-one (S60). The title compound was prepared from 5-(2-pyridyl)oxazole (6) and 6-bromohexanoyl chloride using general procedure B. Column chromatography (SiO$_2$, 10-60% EtOAc-hexanes) afforded S60 (824 mg, 70%) as a tan solid: $^1$H NMR (CDCl$_3$, 400 MHz) δ 8.67 (app d, J=4.8 Hz, 1H), 7.88 (s, 1H), 7.86 (app s, 1H), 7.82 (dt, J=7.6, 1.6 Hz, 1H), 7.33 (ddd, J=7.0, 4.8, 1.2 Hz, 1H), 7.43 (t, J=6.8 Hz, 2H), 3.15 (t, 7.6 Hz, 2H), 1.97-1.90 (m, 2H), 1.86-1.79 (m, 2H), 1.61-1.53 (m, 2H); $^{13}$C NMR (CDCl$_3$, 100 MHz) δ 188.0, 157.2, 153.3, 150.1, 146.2, 137.1, 126.8, 124.1, 120.3, 38.7, 33.4, 32.4, 27.6, 23.0; ESI-TOF m/z 323.0386 (C$_{14}$H$_{15}$BrN$_2$O$_2$+H$^+$ requires 323.0390).

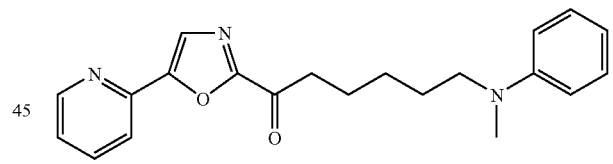

6-(Methyl(phenyl)amino)-1-(5-(pyridin-2-yl)oxazol-2-yl)hexan-1-one (12o). 6-Bromo-1-(5-(pyridin-2-yl)oxazol-2-yl)hexan-1-one (S60, 54 mg, 0.167 mmol) was added to a dry ½ dram vial under Ar and N-methylaniline (53.7 mg, 0.501 mmol) was added. The neat reactants were stirred overnight before diluting the reaction with CH$_2$Cl$_2$ and loading directly onto a PTLC plate. Elution with 1% MeOH—CH$_2$Cl$_2$ afforded 12o (30 mg, 52%) as a colorless oil: $^1$H NMR (CDCl$_3$, 400 MHz) δ 8.67 (ddd, J=4.8, 1.4, 0.8 Hz, 1H), 8.79 (s, 1H), 8.76 (t, J=1.2 Hz, 1H) 7.81 (dt, J=7.6, 1.6 Hz, 1H), 7.32 (ddd, J=7.4, 4.8, 1.6 Hz, 1H), 7.24-7.19 (m, 2H), 7.70-7.65 (m, 3H), 3.32 (t, J=7.2 Hz, 2H), 3.13 (t, J=7.6 Hz, 2H), 2.92 (s, 3H), 1.86-1.79 (m, 2H), 1.68-1.60 (m, 2H), 1.48-1.40 (m, 2H); $^{13}$C NMR (CDCl$_3$, 100 MHz) δ 188.3, 157.3, 153.3, 150.1, 149.2, 146.2, 137.1, 129.1, 126.8, 124.1, 120.4, 115.9, 112.1, 52.5, 39.0, 38.3, 26.7, 26.4, 23.9; ESI-TOF m/z 350.1868 (C$_{21}$H$_{23}$N$_3$O$_2$+H$^+$ requires 350.1863).

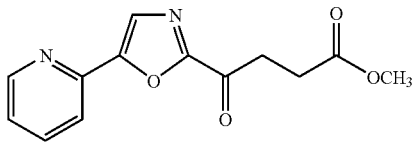

Methyl 4-oxo-4-(5-(pyridin-2-yl)oxazol-2-yl)butanoate (14a). The title compound was prepared from 5-(2-pyridyl)oxazole (6) and methyl succinate using general procedure B. Column chromatography (SiO$_2$, 10-60% EtOAc-hexanes) afforded 14a (433 mg, 16%) as a white solid: $^1$H NMR (CDCl$_3$, 400 MHz) δ 8.67 (app d, J=4.0 Hz, 1H), 7.90 (s, 1H), 7.86 (t, J=7.6 Hz, 1H), 7.82 (t, J=7.6 Hz, 1H), 7.33 (t, J=5.6 Hz, 1H), 3.71 (s, 3H), 3.46 (t, J=6.4 Hz, 2H), 2.82 (t, J=6.4 Hz, 2H); $^{13}$C NMR (CDCl$_3$, 100 MHz) δ 186.3, 172.6, 157.0, 153.4, 150.1, 146.2, 137.1, 127.0, 124.2, 120.4, 52.0, 33.9, 27.7; ESI-TOF m/z 261.0865 (C$_{13}$H$_{12}$N$_2$O$_4$+H$^+$ requires 261.0870).

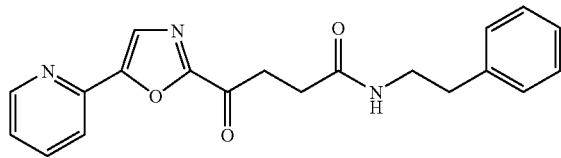

4-Oxo-N-phenethyl-4-(5-(pyridin-2-yl)oxazol-2-yl)butanamide (13a). The title compound was prepared from methyl 4-oxo-4-(5-(pyridin-2-yl)oxazol-2-yl)butanoate (14a) and phenethylamine using general procedure N. PTLC (66% EtOAc-hexanes) afforded 13a (53 mg, 40%) as clear oil: $^1$H NMR (CDCl$_3$, 400 MHz) δ 8.64 (ddd, J=4.8, 1.8, 0.8 Hz, 1H), 7.77 (dt, J=7.8, 2.0 Hz, 1H), 7.69 (s, 1H), 7.56 (dt, J=7.6, 1.2 Hz, 1H), 7.28 (ddd, J=7.6, 4.8, 1.2 Hz, 1H), 7.22-7.17 (m, 2H), 7.13-7.07 (m, 3H), 4.73 (br s, 1H), 3.49 (ddd, J=13.8, 10.4, 5.6 Hz, 1H), 3.33 (ddd, J=14.0, 10.4, 6.0 Hz, 1H), 2.87-2.62 (m, 4H), 2.53-2.53 (m, 1H), 2.41-2.35 (m, 1H); $^{13}$C NMR (CDCl$_3$, 100 MHz) δ 174.4, 163.0, 152.6, 150.0, 146.4, 138.6, 137.0, 128.7, 128.4, 126.3, 124.8, 123.6, 119.5, 87.9, 41.6, 34.5, 33.3, 29.0; ESI-TOF m/z 350.1499 (C$_{20}$H$_{19}$N$_3$O$_3$+H$^+$ requires 350.1499).

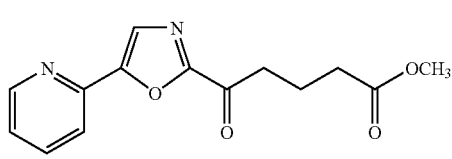

Methyl 5-oxo-5-(5-(pyridin-2-yl)oxazol-2-yl)pentanoate (14b). The title compound was prepared from 5-(2-pyridyl)oxazole (6) and 4-methoxycarbonylpentanoic acid using general procedure B. Column chromatography (SiO$_2$, 10-70% EtOAc-hexanes) afforded 14b (430 mg, 16%) as a white solid: $^1$H NMR (CDCl$_3$, 400 MHz) δ 8.67 (ddd, J=4.8, 1.6, 0.8 Hz, 1H), 7.88 (s, 1H), 7.86 (t, J=1.2 Hz, 1H), 7.82 (dt, J=7.4, 2.0 Hz, 1H), 7.32, (ddd, J=7.6, 4.8, 1.2 Hz, 1H), 3.69, (s, 3H), 3.21 (t, J=7.2 Hz, 2H), 2.47, (t, J=7.2 Hz, 2H), 2.20 (quint, J=7.2 Hz, 2H); $^{13}$C NMR (CDCl$_3$, 100 MHz) δ 187.4, 173.3, 157.1, 153.3, 150.1, 146.2, 137.1, 126.9, 124.1, 120.4, 51.6, 38.0, 32.9, 18.9; ESI-TOF m/z 275.1023 (C$_{14}$H$_{14}$N$_2$O$_4$+H$^+$ requires 275.1026).

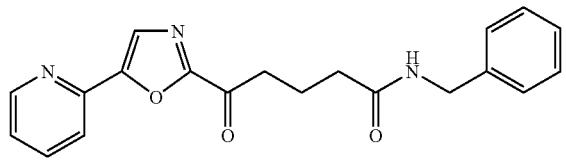

N-Benzyl-5-oxo-5-(5-(pyridin-2-yl)oxazol-2-yl)pentanamide (13b). The title compound was prepared from methyl 5-oxo-5-(5-(pyridin-2-yl)oxazol-2-yl)pentanoate (14b) and benzylamine using general procedure N. PTLC (67% EtOAc-hexanes) afforded 13b (12 mg, 56%) as white solid: $^1$H NMR (CDCl$_3$, 400 MHz) δ 8.67 (app d, J=4.4 Hz, 1H), 7.86 (s, 1H), 7.84 (s, 1H), 7.81 (dt, J=7.2, 1.6 Hz, 1H), 7.35-7.25 (m, 6H), 5.97 (br s, 1H), 4.45 (d, J=5.6 Hz, 2H), 3.21 (t, J=7.2 Hz, 2H), 2.36 (t, J=7.2 Hz, 2H), 2.16 (quint, J=7.2 Hz, 2H); $^{13}$C NMR (CDCl$_3$, 100 MHz) δ 187.7, 171.8, 157.1, 153.3, 150.1, 146.2, 138.2, 137.1, 128.7, 127.8, 127.5, 126.9, 124.2, 120.4, 43.7, 38.1, 35.3, 19.9; ESI-TOF m/z 350.1495 (C$_{20}$H$_{19}$N$_3$O$_3$+H$^+$ requires 350.1499).

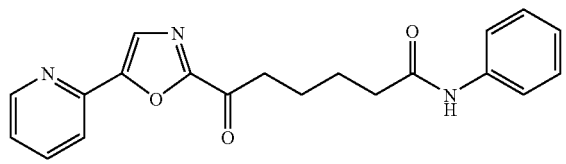

Methyl 6-oxo-6-(5-(pyridin-2-yl)oxazol-2-yl)hexanoate (14c). The title compound was prepared from 5-(2-pyridyl)oxazole (6) and 5-methoxycarbonylhexanoic acid using general procedure B. Column chromatography (SiO$_2$, 10-50% EtOAc-hexanes) afforded 14c (246 mg, 14%) as a white solid: $^1$H NMR (CDCl$_3$, 400 MHz) δ 8.67 (app d, J=4.4 Hz, 1H), 7.88 (s, 1H), 7.87 (d, J=8 Hz, 1H), 7.82 (dt, J=7.6, 1.6 Hz, 1H), 7.33 (ddd, J=7.6, 5.0, 1.2 Hz), 3.68 (2, 3H), 3.15 (t, J=6.8 Hz, 2H), 2.39 (t, J=7.2 Hz, 2H), 1.87-1.72 (m, 4H); $^{13}$C NMR (CDCl$_3$, 100 MHz) δ 187.8, 173.7, 157.2, 153.3, 150.1, 146.2, 137.1, 126.8, 124.1, 120.4, 51.5, 38.6, 33.7, 24.3, 23.3; ESI-TOF m/z 289.1178 (C$_{15}$H$_{16}$N$_2$O$_4$+H$^+$ requires 289.1183).

6-Oxo-N-phenyl-6-(5-(pyridin-2-yl)oxazol-2-yl)hexanamide (13c). The title compound was prepared from methyl 6-oxo-6-(5-(pyridin-2-yl)oxazol-2-yl)hexanoate (14c) and aniline using general procedure N. PTLC (66% EtOAc-hexanes) afforded 13c (132 mg, 61%) as white solid: $^1$H NMR (CDCl$_3$, 400 MHz) δ 8.67 (app d, J=4.8 Hz, 1H), 7.88 (s, 1H), 7.86 (s, 1H), 7.82 (dt, J=7.6, 8.8 Hz, 1H), 7.54 (d, J=8.0 Hz, 1H), 7.50 (br s, 1H), 7.35-7.28 (m, 3H), 7.10 (t, J=7.2 Hz, 3H), 7.20 (t, J=6.4 Hz, 2H), 2.45 (t, J=6.8 Hz, 2H), 1.93-1.83 (m, 4H); $^{13}$C NMR (CDCl$_3$, 100 MHz) δ 188.1, 170.7, 157.2, 153.4, 150.1, 146.2, 137.9, 137.1, 129.0, 126.9, 124.2, 120.4, 119.8, 38.7, 37.3, 24.9, 23.2; ESI-TOF m/z 350.1497 (C$_{20}$H$_{19}$N$_3$O$_3$+H$^+$ requires 350.1499).

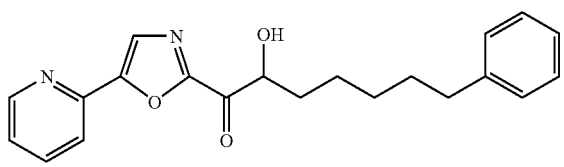

2-Hydroxy-7-phenyl-1-(5-(pyridin-2-yl)oxazol-2-yl)heptan-1-one (13d). KHMDS (0.5 M in toluene, 0.285 mL, 0.142 mmol) was added to a dry flask containing anhydrous THF (1.7 mL) and the solution was cooled to −78° C. A solution of OL-135 (2b, 34 mg, 0.102 mmol) in anhydrous THF (0.8 mL) was added dropwise and the solution stirred for 15 min before dropwise addition of a solution of freshly prepared Davis reagent (40 mg, 0.153 mmol) in THF (0.8 mL). The reaction mixture was stirred at −78° C. for 15 min before being quenched by the addition of $H_2O$ (0.1 mL). The reaction mixture was allowed to warm to 0° C. and $Et_3N$ (0.1 mL) was added. Stirring at 0° C. was continued for 5 min before pouring the reaction mixture onto aqueous 5% HCl (10 mL). Stirring was again continued for 15 min at room temperature before extracting with EtOAc. The organic phase was dried over anhydrous $Na_2SO_4$ and concentrated. Two successive PTLC purifications ($1^{st}$, 50% hexanes-EtOAc; $2^{nd}$, 1% MeOH—$CH_2Cl_2$) afforded 13d (14 mg, 39%): $^1H$ NMR ($CDCl_3$, 600 MHz) δ 8.69 (app d, J=4.8 Hz, 1H), 7.93 (s, 1H), 7.88 (d, J=7.8 Hz, 1H), 7.83 (app t, J=7.2 Hz, 1H), 7.35 (dd, J=6.9, 4.8 Hz, 1H), 7.27-7.24 (m, 2H), 7.17-7.15 (m, 3H), 5.04 (app d, J=4.8 Hz, 1H), 3.46 (br s, 1H), 2.60 (t, J=7.8 Hz, 2H), 2.12-2.06 (m, 1H), 1.81-1.35 (m, 7H); $^{13}C$ NMR ($CDCl_3$, 150 MHz) δ 189.4, 155.3, 153.6, 150.2, 145.9, 142.6, 137.2, 128.3, 128.2, 127.1, 125.6, 124.4, 120.6, 74.9, 35.8, 35.0, 31.2, 28.9, 24.9; ESI-TOF m/z 351.1703 ($C_{21}H_{22}N_2O_3$+$H^+$ requires 351.1703).

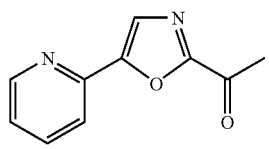

1-(5-(Pyridin-2-yl)oxazol-2-yl)ethanone (S61). (Boger, D. L.; Miyauchi, H.; et al. *J. Med. Chem.* 2005, 48, 1849-1856) 5-(Pyridin-2-yl)oxazole (X, 1.5 g, 10.26 mmol) was dissolved in anhydrous THF (60 mL, 0.17 M) and cooled to −78° C. under Ar. n-BuLi (2.18 M in hexanes, 5.65 mL, 12.32 mmol) was then added dropwise over 10 min. After addition, the dry ice/acetone bath was replaced with an ice bath and $ZnCl_2$ (1.0 M in $Et_2O$, 12.83 mL, 12.83 mmol) was added dropwise. After complete addition, stirring was continued for a further 45 min at 0° C. before addition of CuI (2.932 g, 15.40 mmol). Stirring was continued for 15 min before adding acetyl chloride (2.12 g, 27 mmol, 2.63 eq; freshly purified by refluxing over $PCl_5$ followed by distillation and subsequent redistillation from distilled quinoline) dropwise. The reaction was stirred at 0° C. for 10 min before removing the ice bath and stirring for 1 h at room temperature. The reaction was quenched by the addition of saturated aqueous $NaHCO_3$, diluted with $H_2O$ and extracted with EtOAc. The organic phase was dried over anhydrous $Na_2SO_4$ and concentrated. Column chromatography (0-50% EtOAc-hexanes) followed by recrystallization (EtOAc-hexanes) afforded S61 (960 mg, 50%) as a white solid: $^1H$ NMR ($CDCl_3$, 600 MHz) δ 8.67 (app d, J=4.2 Hz, 1H), 7.90 (s, 1H), 7.88 (app d, J=7.8 Hz, 1H), 7.82 (dt, J=7.5, 1.2 Hz, 1H), 7.33 (app dd, J=6.9, 5.4 Hz, 1H), 2.73 (s, 3H); $^{13}C$ NMR ($CDCl_3$, 600 MHz) δ 185.6, 157.5, 153.4, 150.1, 146.2, 137.1, 127.0, 124.2, 120.4, 26.6; ESI-TOF m/z 189.0661 ($C_{10}H_8N_2O_2$+$H^+$ requires 189.0659).

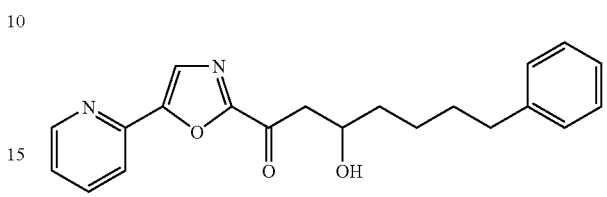

3-Hydroxy-7-phenyl-1-(5-(pyridin-2-yl)oxazol-2-yl)heptan-1-one (13e). 1-(5-(Pyridin-2-yl)oxazol-2-yl)ethanone (S61, 35 mg, 0.186 mmol) was dissolved in anhydrous THF (1.5 mL) and cooled to −78° C. under Ar. KHMDS (0.4 M in toluene, 0.512 mL, 0.204 mmol) was added dropwise and stirring was continued at −78° C. for 30 min before adding a solution of 5-phenylpentanal (42 mg, 0.26 mmol) in THF (0.5 mL) dropwise. After 15 min, the reaction was quenched by cannulating the cold reaction mixture directly from the flask onto a plug of oven-dried silica gel. The silica plug was rinsed with EtOAc and the organic filtrate concentrated. PTLC (66% EtOAc-hexanes) afforded 13e (23 mg, 35%): $^1H$ NMR ($CDCl_3$, 500 MHz) δ 8.67 (app d, J=4.5 Hz, 1H), 7.90 (s, 1H), 7.87 (d, J=8.0 Hz, 1H), 7.82 (dt, J=7.8, 2 Hz, 1H), 7.33 (ddd, J=7.3, 4.8, 1.5 Hz, 1H), 7.29-7.26 (m, 2H), 7.19-7.15 (m, 3H), 4.27-4.22 (m, 1H), 3.29 (dd, J=17, 3 Hz, 1H), 3.22 (dd, J=17, 9 Hz, 1H), 2.95-2.80 (br s), 2.64 (t, J=7.5 Hz, 2H), 1.72-1.40 (m, 6H); $^{13}C$ NMR ($CDCl_3$, 125 MHz) δ 188.0, 157.3, 153.6, 150.2, 146.1, 142.5, 137.1, 128.4, 128.3, 127.0, 125.7, 124.3, 120.5, 67.8, 46.3, 36.7, 35.9, 31.3, 25.2; ESI-TOF m/z 351.1706 ($C_{21}H_{22}N_2O_3$+$H^+$ requires 351.1703).

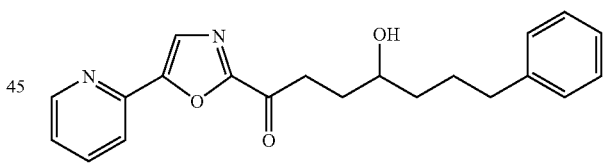

4-Hydroxy-7-phenyl-1-(5-(pyridin-2-yl)oxazol-2-yl)heptan-1-one (13f). 4-(Benzyloxy)butan-1-ol was oxidized to 4-(benzyloxy)butanal (7.35 g, 79%) following general procedure P. 4-(Benzyloxy)butanal was converted to (1-(benzyloxy)-7-phenylheptan-4-yloxy)triisopropylsilane with (3-phenylpropyl)magnesium bromide following general procedure Q. Column chromatography (5% EtOAc-hexanes) afforded (1-(benzyloxy)-7-phenylheptan-4-yloxy) triisopropylsilane (5.82 g, 81%) as a pale yellow oil. 7-Phenyl-4-(triisopropylsilyloxy)heptan-1-ol was prepared from (1-(benzyloxy)-7-phenylheptan-4-yloxy)triisopropylsilane following general procedure R. Column chromatography (5-10% EtOAc-hexanes) afforded 7-phenyl-4-(triisopropylsilyloxy)heptan-1-ol (3.31 g, 73%) as a clear oil. 7-Phenyl-4-(triisopropylsilyloxy)heptanoic acid was prepared from 7-phenyl-4-(triisopropylsilyloxy)heptan-1-ol following general procedure S. Column chromatography (5% EtOAc-hexanes) afforded 7-phenyl-4-(triisopropylsilyloxy)heptanoic acid (1.52, 47%) as a white solid. 7-Phenyl-1-(5-(pyridin-2-yl)oxazol-2-yl)-4-(triisopropylsilyloxy)heptan-1-one was prepared from 5-(2-pyridyl)oxazole (6) and 7-phenyl-4-(triisopropylsilyloxy)heptanoic acid using general procedure B. Column chromatography (SiO$_2$, 10-50% EtOAc-hexanes) afforded 7-phenyl-1-(5-(pyridin-2-yl)oxazol-2-yl)-4-(triisopropylsilyloxy)heptan-1-one (689 mg, 54%) as a clear oil. The title compound was prepared from 7-phenyl-1-(5-(pyridin-2-yl)oxazol-2-yl)-4-(triisopropylsilyloxy)heptan-1-one using general procedure O. PTLC (50% EtOAc-hexanes) afforded 13f (16 mg, 40%) as a white solid: $^1$H NMR (CDCl$_3$, 600 MHz) δ 8.66 (app d, J=4.2 Hz, 0.5H), 8.62 (app d, J=4.2 Hz, 0.5H), 7.89 (s, 0.5H), 7.86 (app d, J=7.8 Hz, 0.5H), 7.80 (app t, J=7.8 Hz, 0.5H), 7.73 (app q, J=8.4 Hz, 0.5H), 7.65-7.61 (m, 0.75H), 7.57, (d, J=8.4 Hz, 0.25H), 7.32-7.21 (m, 3H), 7.19-7.14 (m, 3H), 4.45-4.43 (m, 0.5H), 4.35-4.30 (m, 0.5H), 3.72-3.69 (m, 0.5H), 3.29-3.21 (m, 1H), 2.68-2.59 (m, 2.75H), 2.40-2.30 (m, 0.75H), 2.23-2.19 (m, 0.25H), 2.04-1.96 (m, 1.25H), 1.89-1.53 (m, 3.5H); $^{13}$C NMR (CDCl$_3$, 150 MHz) δ 188.6, 163.8, 163.7, 157.3, 153.3, 151.4, 150.1, 149.9, 147.0, 146.2, 142.2, 142.1, 137.1, 136.8, 136.7, 128.4, 128.3, 128.2, 126.9, 125.8, 125.7, 125.6, 125.0, 124.9, 124.1, 123.0, 120.4, 119.4, 119.3, 100.9, 100.5, 82.4, 80.4, 70.9, 37.6, 37.1, 36.9, 36.5, 35.8, 35.7, 35.5, 34.9, 31.6, 30.4, 30.3, 27.8, 27.5, 27.4; ESI-TOF m/z 351.1701 (C$_{21}$H$_{22}$N$_2$O$_3$+H$^+$ requires 351.1703).

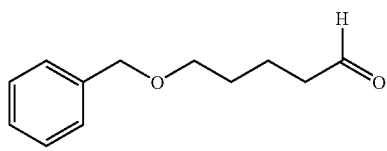

5-(Benzyloxy)pentanal (S62). The title compound was prepared from 5-(benzyloxy)-1-pentanol following general procedure P. Column chromatography (15% EtOAc-hexanes) afforded S62 (11.0 g, 68%) as a pale yellow oil: $^1$H NMR (CDCl$_3$, 400 MHz) δ 9.77 (m, 1H), 7.36-7.29 (m, 5H), 4.51 (s, 2H), 3.50 (t, J=6.2 Hz, 2H), 2.49-2.45 (m, 2H), 1.79-1.63 (m, 4H).

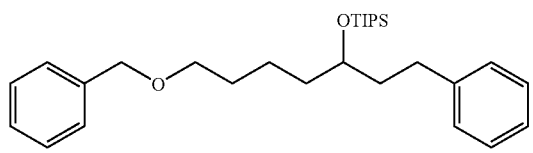

(7-(Benzyloxy)-1-phenylheptan-3-yloxy)triisopropylsilane (S63). The title compound was prepared from 5-(benzyloxy)pentanal (S62) following general procedure Q. Column chromatography (5% EtOAc-hexanes) afforded S63 (2.7 g, 85%) as a pale yellow oil: $^1$H NMR (CDCl$_3$, 400 MHz) δ 7.37-7.28 (m, 7H), 7.21-7.19 (m, 2H), 4.53 (s, 2H), 3.95-3.88 (m, 1H), 3.51 (t, J=6.4 Hz, 2H), 2.68 (t, J=8.2 Hz, 2H), 1.91-1.75 (m, 2H), 1.70-1.58 (m, 4H), 1.50-1.43 (m, 2H), 1.09 (s, 18H); $^{13}$C NMR (CDCl$_3$, 100 MHz) δ 142.8, 138.6, 128.3 (4C), 127.6 (4C), 127.4, 125.6, 72.9, 71.8, 70.4, 38.4, 36.3, 31.2, 30.0, 21.6, 18.2, 12.7.

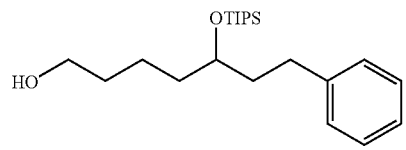

7-Phenyl-5-(triisopropylsilyloxy)heptan-1-ol (S64). A solution of the (7-(benzyloxy)-1-phenylheptan-3-yloxy)triisopropylsilane (S63, 2.6 g, 5.7 mmol) in 30 mL of EtOAc was treated with 10% Pd/C (400 mg). The reaction mixture was purged with H$_2$ and stirred overnight at 25° C. The suspension was concentrated and purified by column chromatography (15% EtOAc-hexanes) to afford S64 (1.0 g, 50%) as a pale yellow oil: $^1$H NMR (CDCl$_3$, 500 MHz) δ 7.38-7.34 (m, 2H), 7.28-7.24 (m, 3H), 4.01-3.97 (m, 1H), 3.74 (t, J=6.6 Hz, 2H), 1.97-1.84 (m, 2H), 1.70-1.64 (m, 4H), 1.53-1.48 (m, 2H), 1.16 (s, 18H); $^{13}$C NMR (CDCl$_3$, 100 MHz) δ 142.7, 128.3 (4C), 125.6, 71.8, 62.9, 38.2, 36.3, 33.0, 31.2, 21.0, 18.2, 12.7.

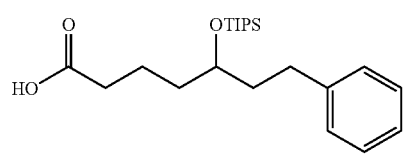

7-Phenyl-5-(triisopropylsilyloxy)heptanoic acid (S65). The title compound was prepared from 7-phenyl-5-(triisopropylsilyloxy)heptan-1-ol (S64) following general procedure S. Column chromatography (10-20% EtOAc-hexanes) afforded S65 (445 mg, 49%) as a yellow oil: $^1$H NMR (CDCl$_3$, 400 MHz) δ 7.30-7.28 (m, 2H), 7.20-7.18 (m, 3H), 3.95-3.90 (m, 1H), 2.66 (t, J=8.2 Hz, 2H), 2.39 (t, J=7.4 Hz, 2H), 1.87-1.79 (m, 2H), 1.75-1.68 (m, 2H), 1.65-1.59 (m, 2H), 1.07 (s, 18H).

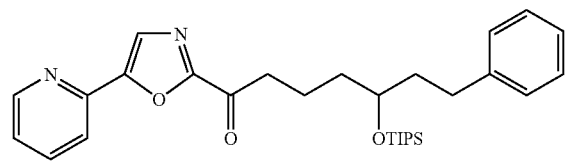

7-Phenyl-1-(5-(pyridin-2-yl)oxazol-2-yl)-5-(triisopropylsilyloxy)heptan-1-one (S66). The title compound was prepared from 5-(2-pyridyl)oxazole (6) and 7-phenyl-5-(triisopropylsilyloxy)heptanoic acid (S65) using general procedure B. Column chromatography (SiO$_2$, 10-40% EtOAc-hexanes) afforded S66 (55 mg, 21%) as a clear oil: $^1$H NMR (CDCl$_3$, 400 MHz) δ 8.67 (app d, J=4.8 Hz, 1H), 7.88 (s, 1.5H), 7.86 (s, 0.5H), 7.81 (dt, J=7.6, 1.6 Hz, 1H), 7.33-7.25 (m, 3H), 7.20-7.15 (m, 3H), 3.95 (quint, J=5.2 Hz, 1H), 3.14 (t, J=7.2 Hz, 2H), 2.67 (t, J=8.8 Hz, 2H), 1.91-1.79 (m, 4H), 1.74-1.63 (m, 2H), 1.06 (s, 21H); $^{13}$C NMR (CDCl$_3$, 150 MHz) δ 188.2, 157.3, 153.3, 150.1, 146.3, 142.5, 137.1, 128.4, 128.3, 126.9, 125.6, 124.1, 120.4, 71.6, 39.3, 38.3, 35.8, 31.2, 19.3, 18.2, 12.7; ESI-TOF m/z 507.3033 (C$_{30}$H$_{42}$N$_2$O$_3$Si+H$^+$ requires 507.3037).

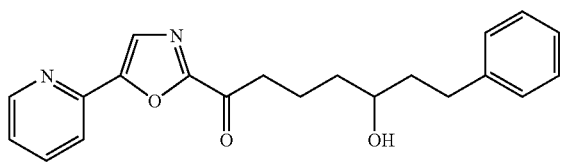

5-Hydroxy-7-phenyl-1-(5-(pyridin-2-yl)oxazol-2-yl)heptan-1-one (13g). The title compound was prepared from 7-phenyl-1-(5-(pyridin-2-yl)oxazol-2-yl)-5-(triisopropylsilyloxy)heptan-1-one (S66) using general procedure O. PTLC (33% EtOAc-hexanes) afforded 13g (15 mg, 57%): $^1$H NMR (CDCl$_3$, 400 MHz) δ 8.67 (app d, J=4.8 Hz, 0.5H), 8.64 (app d, J=4.4 Hz, 0.5H), 7.88 (s, 0.7H), 7.86 (s, 0.3H), 7.81 (dt, J=7.6, 1.6 Hz, 0.5H), 7.76 (dt, J=7.6, 1.6 Hz, 0.5H), 7.70 (s, 0.3H), 7.68-7.65 (m, 0.7H), 7.35-7.10 (m, 6H), 4.31 (br ex s, 1H), 4.15-4.05 (m, 0.5H), 3.92 (br s, 1H), 3.72-3.66 (m, 0.5H), 3.22-3.09 (m, 1H), 2.88-2.61 (m, 2H), 2.25-1.37 (m, 7H); $^{13}$C NMR (CDCl$_3$, 150 MHz) δ 188.3, 164.7, 157.2, 153.3, 151.1, 150.1, 149.9, 147.1, 146.2, 142.1, 142.0, 137.1, 136.9, 128.4, 128.3, 128.2, 126.9, 125.8, 125.7, 124.9, 124.2, 123.1, 120.4, 119.5, 93.2, 70.7, 70.5, 39.1, 38.8, 37.4, 36.7, 32.1, 32.0, 31.6, 30.4, 20.0, 18.5; ESI-TOF m/z 351.1705 (C$_{21}$H$_{22}$N$_2$O$_3$+H$^+$ requires 351.1703).

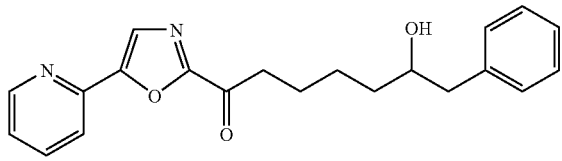

6-Hydroxy-7-phenyl-1-(5-(pyridin-2-yl)oxazol-2-yl)heptan-1-one (13h). 6-(Benzyloxy)hexan-1-ol was oxidized to 6-(benzyloxy)hexanal following general procedure P. 6-(Benzyloxy)hexanal was converted to (7-(benzyloxy)-1-phenylheptan-2-yloxy)triisopropylsilane with benzylmagnesium chloride following general procedure Q. Column chromatography (5% EtOAc-hexanes) afforded (7-(benzyloxy)-1-phenylheptan-2-yloxy)triisopropylsilane (2.7 g, 85%) as a pale yellow oil. 7-Phenyl-6-(triisopropylsilyloxy)heptan-1-ol was prepared from (7-(benzyloxy)-1-phenylheptan-2-yloxy)triisopropylsilane following general procedure R. Column chromatography (5-40% EtOAc-hexanes) afforded 7-phenyl-6-(triisopropylsilyloxy)heptan-1-ol (810 mg, 80%) as a clear oil. 7-Phenyl-6-(triisopropylsilyloxy)heptanoic acid was prepared from 7-Phenyl-6-(triisopropylsilyloxy)heptan-1-ol following general procedure S. Column chromatography (5% EtOAc-hexanes) afforded 7-phenyl-6-(triisopropylsilyloxy)heptanoic acid (400 mg, 55%) as a white solid. 7-Phenyl-1-(5-(pyridin-2-yl)oxazol-2-yl)-6-(triisopropylsilyloxy)heptan-1-one was prepared from 5-(2-pyridyl)oxazole (6) and 7-phenyl-6-(triisopropylsilyloxy)heptanoic acid using general procedure B. Column chromatography (SiO$_2$, 10-40% EtOAc-hexanes) afforded 7-phenyl-1-(5-(pyridin-2-yl)oxazol-2-yl)-6-(triisopropylsilyloxy)heptan-1-one (84 mg, 26%) as a clear oil. The title compound was prepared from 7-phenyl-1-(5-(pyridin-2-yl)oxazol-2-yl)-6-(triisopropylsilyloxy)heptan-1-one using general procedure O. PTLC (50% EtOAc-hexanes) afforded 13h (7 mg, 20%) as a white solid: $^1$H NMR (CDCl$_3$, 500 MHz) δ 8.67 (app d, J=4.5 Hz, 1H), 7.88 (s, 1H), 7.87 (d, J=9.5 Hz, 1H), 7.82 (dt, J=7.8, 1.5 Hz, 1H), 7.33-7.29 (m, 3H), 7.25-7.20 (m, 3H), 3.88-3.83 (m, 1H), 3.14 (t, J=7.5 Hz, 2H), 2.84 (dd, J=13.5, 4.0 Hz, 1H), 2.66 (dd, J=13.8, 8.0 Hz, 1H), 1.88-1.78 (m, 2H), 1.78-1.67 (m, 4H); $^{13}$C NMR (CDCl$_3$, 125 MHz) δ 188.3, 157.3, 150.1, 146.3, 138.4, 137.1, 129.4, 128.6, 126.9, 126.5, 124.1, 120.4, 72.4, 44.1, 39.0, 36.4, 25.3, 23.9; ESI-TOF m/z 373.1522 (C$_{21}$H$_{22}$N$_2$O$_3$+Na$^+$ requires 373.1523).

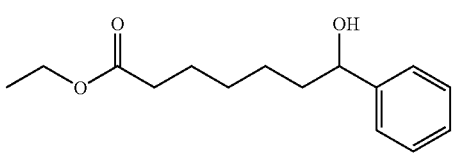

Ethyl 7-hydroxy-7-phenylheptanoate (S67). Ethyl 6-bromohexanoate (5.0 g, 22.4 mmol) was dissolved in anhydrous acetone (35 mL) under Ar and NaI (6.7 g, 44.8 mmol) was added. The reaction mixture was warmed at reflux for 1 h after which the acetone was removed in vacuo. The residue was taken up in EtOAc, washed with H$_2$O, dried over Na$_2$SO$_4$ and concentrated to afford a quantitative yield of ethyl 6-iodohexanoate. Ethyl 6-iodohexanoate (1.621 g, 6.0 mmol) was dissolved in a solution of anhydrous DMF (10 mL) containing benzaldehyde (318 mg, 3.0 mmol) and this mixture was then added at 30° C. to a dark blue/green suspension containing CrCl$_2$ (1.475 g, 12 mmol) and cobalt phthalocyanine (343 mg, 0.6 mmol) in anhydrous DMF (30 mL). The mixture was stirred at room temperature for 1 h and then filtered through a pad of Celite. The Celite was rinsed with Et$_2$O and the filtrate poured onto saturated aqueous NaCl and extracted with Et$_2$O. The combined Et$_2$O extracts were washed with saturated aqueous NaCl, dried over anhydrous MgSO$_4$ and concentrated. Column chromatography (0-50% EtOAc-hexanes) afforded S67 (504 mg, 67%): $^1$H NMR (CDCl$_3$, 400 MHz) δ 7.28-7.24 (m, 4H), 7.23-7.17 (m, 1H), 4.55 (t, J=6 Hz, 1H), 4.03 (q, J=7.2 Hz, 2H), 2.20 (t, J=7.6 Hz, 2H), 1.77-1.51 (m, 4H), 1.41-1.22 (m, 4H), 1.19 (t, J=7.2 Hz, 3H); $^{13}$C NMR (CDCl$_3$, 100 MHz) δ 173.5, 144.8, 127.8, 126.8, 125.5, 73.7, 59.8, 38.6, 33.8, 28.6, 25.0, 24.4, 13.8.

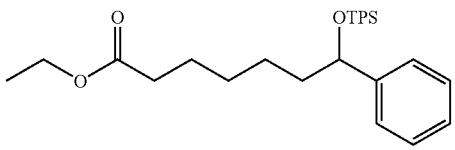

Ethyl 7-phenyl-7-(triisopropylsilyloxy)heptanoate (S68). Ethyl 7-hydroxy-7-phenylheptanoate (S67, 258 mg, 1.03 mmol) was dissolved in anhydrous THF (4.0 mL) under Ar and cooled to 0° C. TIPS-OTf (505 mg, 1.65 mmol) was added and the reaction mixture stirred for 2 min before adding NaH (60% dispersion in oil, 54 mg, 1.34 mmol) portionwise. After 10 min, the reaction was quenched by the addition of H$_2$O and then extracted with CH$_2$Cl$_2$. The organic phase was dried over anhydrous Na$_2$SO$_4$ and concentrated. Column chromatography (0-4% EtOAc-hexanes) afforded S68 (368 mg, 88%): $^1$H NMR (CDCl$_3$, 400 MHz) δ 7.29-7.26 (m, 4H), 7.23-7.18 (m, 1H), 4.75 (t, J=6.0 Hz, 1H), 4.09 (q, J=6.8 Hz, 2H), 2.22 (t, J=7.2 Hz, 2H), 1.82-1.64 (m, 2H), 1.59-1.52 (m, 2H), 1.30-1.21 (m, 7H), 1.06-0.95 (m, 21H); $^{13}$C NMR (CDCl$_3$, 100 MHz) δ

173.7, 145.4, 127.8, 126.8, 126.1, 75.0, 60.0, 40.5, 34.2, 29.2, 24.9, 24.3, 18.0, 17.9, 14.2, 12.3.

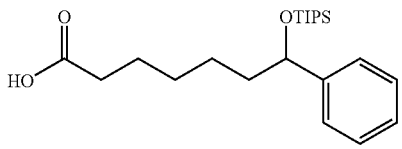

7-Phenyl-7-(triisopropylsilyloxy)heptanoic acid (S69). Ethyl 7-phenyl-7-(triisopropylsilyloxy)heptanoate (S68, 319 mg, 0.78 mmol, 1.0 equiv) was dissolved in THF (2 mL) and a LiOH solution (362 mg LiOH in 10 mL $H_2O$; use 1.0 mL, 0.863 mmol) was added. EtOH (1.0 mL) was added to bring the solution to homogeneity. After stirring at room temperature for 8 h, the reaction mixture was diluted with $H_2O$ and acidified to pH 2 with aqueous 1 N HCl. The acidic aqueous solution was extracted with $CH_2Cl_2$ and the combined organic phase dried over anhydrous $Na_2SO_4$ and concentrated. Column chromatography (0-15% EtOAc-hexanes) afforded S69 (270 mg, 91%): $^1$H NMR (CDCl$_3$, 600 MHz) δ 7.29-7.27 (m, 4H), 7.22-7.19 (m, 1H), 4.75 (t, J=6.0 Hz, 1H), 2.29 (t, J=7.2 Hz, 2H), 1.80-1.75 (m, 1H), 1.72-1.66 (m, 1H), 1.59-1.54 (m, 2H), 1.29-1.21 (m, 4H), 1.06-1.00 (m, 12H), 0.95 (d, 6.6 Hz, 9H); $^{13}$C NMR (CDCl$_3$, 150 MHz) δ 180.3, 145.5, 127.8, 126.8, 126.1, 75.0, 40.6, 34.0, 29.1, 24.6, 24.4, 18.0, 17.9, 12.3.

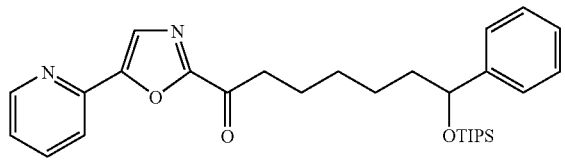

7-Phenyl-1-(5-(pyridin-2-yl)oxazol-2-yl)-7-(triisopropylsilyloxy)heptan-1-one (S70). The title compound was prepared from 5-(2-pyridyl)oxazole (6) and 7-phenyl-7-(triisopropylsilyloxy)heptanoic acid (S69) using general procedure B. Column chromatography (SiO$_2$, 5-40% EtOAc-hexanes) afforded S70 (47 mg, 21%) as a clear oil: $^1$H NMR (CDCl$_3$, 600 MHz) δ 8.67 (app d, J=4.8 Hz, 1H), 7.87 (s, 1H), 7.85 (s, 1H), 7.81 (app t, J=7.2 Hz, 1H), 7.32-7.27 (m, 5H), 7.22-7.20 (m, 1H), 4.76 (t, J=6.0 Hz, 1H), 3.05 (t, J=7.8 Hz, 2H), 1.83-1.77 (m, 1H), 1.74-1.68 (m, 3H), 1.37-1.33 (m, 2H), 1.29-1.23 (m, 2H), 1.06-1.00 (m, 12H), 0.95 (d, J=6.6 Hz, 9H); $^{13}$C NMR (CDCl$_3$, 150 MHz) δ 188.4, 157.3, 153.2, 150.1, 146.3, 145.5, 137.1, 127.8, 126.8, 126.7, 126.1, 124.1, 120.3, 75.0, 40.7, 39.0, 29.2, 24.5, 23.9, 18.0, 17.9, 12.3; ESI-TOF m/z 529.2849 ($C_{30}H_{42}N_2O_3Si+Na^+$ requires 529.2857).

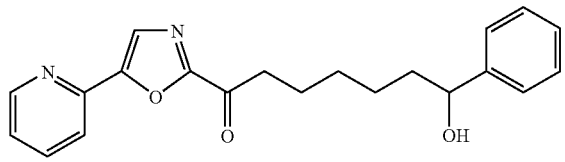

7-Hydroxy-7-phenyl-1-(5-(pyridin-2-yl)oxazol-2-yl)heptan-1-one (13i). The title compound was prepared from 7-phenyl-1-(5-(pyridin-2-yl)oxazol-2-yl)-7-(triisopropylsilyloxy)heptan-1-one (S70) using general procedure O. Column chromatography (SiO$_2$, 50% EtOAc-hexanes) afforded 13i (7 mg, 51%) as a white solid: $^1$H NMR (CDCl$_3$, 600 MHz) δ 8.67 (app d, J=4.2 Hz, 1H), 7.88 (s, 1H), 7.86, (d, J=10.8 Hz, 1H), 7.82 (dt, J=7.5, 1.8 Hz, 1H), 7.35-7.31 (m, 5H), 7.29-7.26 (m, 1H), 4.68 (dd, J=7.2, 6.0 Hz, 1H), 3.10 (t, J=7.8 Hz, 2H), 1.86-1.70 (m, 4H), 1.53-1.32 (m, 4H); $^{13}$C NMR (CDCl$_3$, 125 MHz) δ 188.4, 157.3, 153.2, 150.1, 146.2, 144.8, 137.2, 128.4, 127.5, 126.9, 125.8, 124.1, 120.4, 74.5, 39.0, 38.8, 29.0, 25.5, 23.9; ESI-TOF m/z 373.1525 ($C_{21}H_{22}N_2O_3+Na^+$ requires 373.1523).

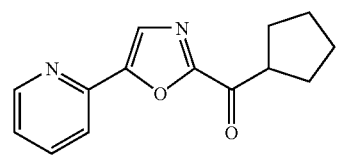

Cyclopentyl(5-(pyridin-2-yl)oxazol-2-yl)methanone (14e). 6-Bromo-1-(5-(pyridin-2-yl)oxazol-2-yl)hexan-1-one (S60, 89 mg, 0.275 mmol) was dissolved in anhydrous DMF (0.3 mL) and K$_2$CO$_3$ (114 mg, 0.826 mmol) and KI (46 mg, 0.275 mmol) were added followed by N-methylaniline (29.5 mg, 0.275 mmol). The reaction mixture was stirred overnight at room temperature before being diluted with EtOAc. The EtOAc mixture was washed with H$_2$O, dried over anhydrous Na$_2$SO$_4$ and concentrated. PTLC (66% hexanes-EtOAc) afforded 14e (34 mg, 59%): $^1$H NMR (CDCl$_3$, 600 MHz) δ 8.67 (app d, J=4.8 Hz, 1H), 7.89 (s, 1H), 7.87 (app d, J=7.8 Hz, 1H), 7.82 (app t, J=7.2, Hz, 1H), 7.32 (app dd, J=7.2, 4.8 Hz, 1H), 3.93 (quint, J=8.4 Hz, 1H), 2.07-2.01 (m, 2H), 1.97-1.91 (m, 2H), 1.80-1.73 (m, 2H), 1.73-1.67 (m, 2H); $^{13}$C NMR (CDCl$_3$, 150 MHz) δ 190.9, 157.5, 153.1, 150.0, 146.3, 137.0, 126.8, 124.0, 120.3, 47.4, 29.7, 26.2; ESI-TOF m/z 243.1133 ($C_{14}H_{14}N_2O_2+H^+$ requires 243.1128).

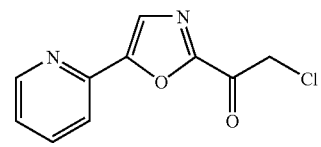

2-Chloro-1-(5-(pyridin-2-yl)oxazol-2-yl)ethanone (14f). 5-(Pyridin-2-yl)oxazole (6, 269 mg, 1.84 mmol) was dissolved in anhydrous Et$_2$O (5.0 mL, 0.37 M) and cooled to −78° C. under Ar. n-BuLi (1.5 M in hexanes, 1.35 mL, 1.1 equiv) was then added dropwise and the reaction mixture was stirred for 30 min. Bu$_3$SnCl (599 mg, 1.84 mmol) in anhydrous Et$_2$O (1.5 mL) was then added dropwise. After complete addition, the cooling bath was removed and the mixture was allowed to warm to room temperature and stirred for 1 h. The reaction was then filtered through oven dried Celite using anhydrous Et$_2$O to rinse the filter cake. The filtrate was concentrated in vacuo to yield 5-(pyridin-2-yl)-2-(tributylstannyl)oxazole which was immediately redissolved in anhydrous THF (10 mL) under Ar. A solution of chloroacetyl chloride in THF (4 mL) was added dropwise and the reaction mixture was stirred for 2 h. The reaction was quenched by the addition of saturated aqueous NH$_4$Cl, diluted with H$_2$O and extracted with EtOAc. The organic layer was dried over anhydrous Na$_2$SO$_4$ and concentrated. Column chromatography (EtOAc-hexanes) followed by PTLC (1% MeOH—$CH_2Cl_2$) afforded 14f (105 mg, 26%) as a colorless oil: $^1$H NMR ($CDCl_3$, 400 MHz) δ 8.68 (app d, J=4.4 Hz, 1H), 7.92 (s, 1H), 7.89 (app d, J=7.6 Hz, 1H), 7.84 (dt, J=7.2, 1.6 Hz, 1H), 7.36 (ddd, J=7.2, 4.8, 1.6 Hz, 1H), 4.90 (s, 2H); $^{13}$C NMR ($CDCl_3$, 125 MHz) δ 178.8, 155.2, 154.1, 150.1, 145.7, 137.1, 127.1, 124.4, 120.5, 45.7; ESI-TOF m/z 223.0269 ($C_{10}H_7N_2O_2Cl+H^+$ requires 223.0269).

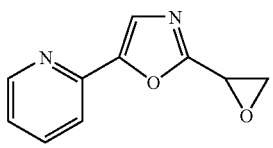

2-(Oxiran-2-yl)-5-(pyridin-2-yl)oxazole (S71). 2-Chloro-1-(5-(pyridin-2-yl)oxazol-2-yl)ethanone (14f, 70 mg, 0.315 mmol) was dissolved in EtOH (5.0 mL) and $NaBH_4$ (24 mg, 0.63 mmol) was added in one portion. After 10 min, the reaction mixture was diluted with $H_2O$, stirred for 10 min and then extracted with EtOAc. The organic layer was dried over anhydrous $Na_2SO_4$ and concentrated to yield 2-chloro-1-(5-(pyridin-2-yl)oxazol-2-yl)ethanol (70 mg, 99%). 2-Chloro-1-(5-(pyridin-2-yl)oxazol-2-yl)ethanol (52 mg, 0.231 mmol) was dissolved in EtOH (2.0 mL) and a 50% solution of NaOH in $H_2O$ (37 mL, 0.463 mmol) was added. The reaction mixture was stirred at room temperature for 30 min before diluting with $H_2O$ and extracting with EtOAc. The organic phase was dried over anhydrous $Na_2SO_4$ and concentrated. PTLC (50% hexanes-EtOAc) afforded S71 (26 mg, 59%) as a colorless oil: $^1$H NMR ($CDCl_3$, 400 MHz) δ 8.63 (ddd, J=4.6, 1.4, 0.8 Hz, 1H), 7.77 (dt, J=7.6, 1.6 Hz, 1H), 7.68 (s, 1H), 7.63 (dt, J=8.0, 0.8 Hz, 1H), 7.25 (ddd, J=7.6, 4.8, 1.2 Hz, 1H), 4.10 (dd, J=4.0, 2.4 Hz, 1H), 3.44 (dd, J=5.6, 2.4 Hz, 1H), 3.25 (dd, J=5.8, 4.4 Hz, 1H); $^{13}$C NMR ($CDCl_3$, 600 MHz) δ 160.1, 151.7, 150.0, 146.8, 136.9, 125.9, 123.2, 119.3, 48.0, 45.5; ESI-TOF m/z 189.0662 ($C_{10}H_8N_2O_2+H^+$ requires 189.0659).

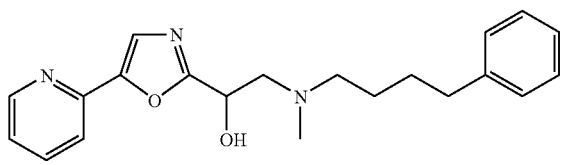

2-(Methyl(4-phenylbutyl)amino)-1-(5-(pyridin-2-yl)oxazol-2-yl)ethanol (14i). 2-(Oxiran-2-yl)-5-(pyridin-2-yl)oxazole (S71, 23 mg, 0.123 mmol) was dissolved in anhydrous THF (0.5 mL) under Ar and N-methyl-4-phenylbutylamine (Ding, C. Z.; Lu, X.; et al. J. Med. Chem. 1993, 36, 1711-1715) (40 mg, 0.245 mmol) was added. The reaction mixture was warmed at 60° C. and stirred overnight. After cooling to room temperature, the reaction mixture was loaded directly onto a PTLC plate and eluted with 2% MeOH, 1% $NH_4OH$ in $CH_2Cl_2$ to yield 14i (39 mg, 91%) as a colorless oil: $^1$H NMR ($CDCl_3$, 400 MHz) δ 8.63 (app d, J=4.4 Hz, 1H), 7.75 (dt, J=7.8, 2.0 Hz, 1H), 7.69 (app d, J=7.6 Hz, 1H), 7.65 (s, 1H), 7.30-7.26 (m, 2H), 7.23 (ddd, J=7.2, 4.8, 1.2 Hz, 1H), 7.20-7.16 (m, 3H), 4.90 (dd, J=9.6, 4.0 Hz, 1H), 2.99 (dd, J=12.4, 10.0 Hz, 1H), 2.79 (dd, J=12.4, 4.0 Hz, 1H), 2.63 (t, J=7.2 Hz, 2H), 2.61-2.56 (m, 1H), 2.52-2.45 (m, 1H), 2.33 (s, 3H), 1.69-1.52 (m, 4H); $^{13}$C NMR ($CDCl_3$, 150 MHz) δ 163.9, 151.2, 149.9, 147.2, 142.2, 136.8, 128.4, 128.3, 125.8, 125.3, 122.9, 119.4, 63.7, 60.9, 57.7, 41.8, 35.7, 29.0, 26.7; ESI-TOF m/z 352.2023 ($C_{21}H_{25}N_3O_2+H^+$ requires 352.2019).

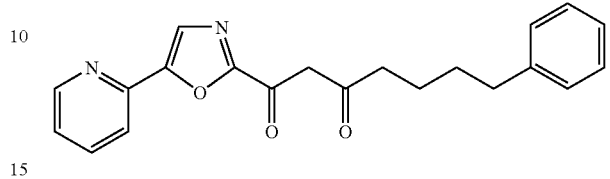

7-Phenyl-1-(5-(pyridin-2-yl)oxazol-2-yl)heptane-1,3-dione (14g). 3-Hydroxy-7-phenyl-1-(5-(pyridin-2-yl)oxazol-2-yl)heptan-1-one (13e, 12 mg, 0.0342 mmol) was dissolved in anhydrous $CH_2Cl_2$ (0.25 mL) under Ar and Dess-Martin periodinane (17.4 mg, 0.0411 mmol) was added. The reaction mixture was stirred at room temperature for 20 min before being filtered through Celite. The Celite pad was rinsed with $CH_2Cl_2$ and the filtrate concentrated. PTLC (50% hexanes-EtOAc) afforded 14g as a white solid (8.2 mg, 69%): $^1$H NMR ($CDCl_3$, 600 MHz) δ 8.68 (app d, J=4.2 Hz, 1H), 7.89 (s, 1H), 7.86-7.80 (m, 2H), 7.32-7.26 (m, 3H), 7.19-7.18 (m, 3H), 6.54 (s, 1H), 2.66 (t, J=7.2 Hz, 2H), 2.48 (t, J=7.2 Hz, 2H), 1.75-1.66 (m, 4H); $^{13}$C NMR ($CDCl_3$, 150 MHz) δ 195.3, 171.7, 157.0, 153.1, 150.1, 146.3, 141.9, 137.1, 128.4, 128.3, 127.4, 125.8, 123.9, 120.2, 98.3, 38.3, 35.6, 30.9, 25.3; ESI-TOF m/z 349.1549 ($C_{21}H_{20}N_2O_3+H^+$ requires 349.1547).

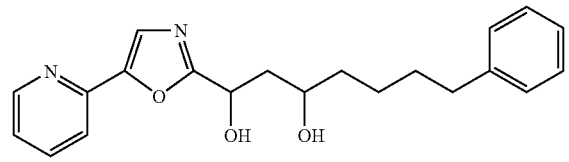

7-Phenyl-1-(5-(pyridin-2-yl)oxazol-2-yl)heptane-1,3-diol (14h). α-Hydroxyketone 13d (11 mg, 0.314 mmol) was dissolved in MeOH (0.2 mL) and $NaBH_4$ (1.5 mg, 0.408 mmol) was added. The mixture was stirred for 10 min before being quenched with $H_2O$ (1.0 mL) and stirred for an additional 10 min. An additional amount of $H_2O$ (5 mL) was added and the mixture extracted with EtOAc. The organic phase was washed with $H_2O$, dried over anhydrous $Na_2SO_4$ and concentrated to yield 14h (9 mg, 99%) as a mixture of 4 diastereomers. $^1$H NMR showns that the syn (S,S:R,R) and anti (R,S:S,R) pairs of enantiomers are present in a 0.63:0.37 ratio: $^1$H NMR ($CDCl_3$, 600 MHz) δ 8.62 (app d, J=4.8 Hz, 1H), 7.76 (t, J=7.8 Hz, 1H), 7.62-7.65 (m, 2H), 7.24-7.27 (m, 3H), 7.14-7.17 (m, 3H), 4.79 (d, J=4.2, 0.63H), 4.71 (d, J=3.0 Hz, 0.37H), 2.59 (app q, J=8.4 Hz, 2H), 1.55-1.71 (m, 4H), 1.31-1.51 (m, 4H); $^{13}$C NMR ($CDCl_3$, 150 MHz) δ 149.5, 149.4, 146.5, 146.5, 142.7, 142.6, 139.6, 137.4, 137.3, 128.4, 128.2, 125.6, 125.3, 125.3, 123.2, 123.2, 119.6, 119.6, 73.9, 72.7, 70.3, 69.9, 35.8, 35.8, 32.7, 32.6, 31.4, 31.3, 29.1, 29.1, 25.5, 25.5; ESI-TOF m/z 353.1860 ($C_{21}H_{24}N_2O_3+H^+$ requires 353.1868).

Compounds 5j, 5k, 5aa, 5jj, 5mm, 4ss, 4jj, 12a, 12f, 12n, 14a, and 14d had a purity greater than 99%. Compounds 5f, 5l, 5o, 5ff, 5ii, 4y, 4z, 4aa, 4 cc, 4gg, 12g, 12i, and 13b had a purity of 99%. Compounds 5g, 5h, 5i, 5v, 5w, 5y, 5gg, 4f, 4qq, 4p, 4q, 4r, 4x, 12k, 12l, 12m, 12p, 12q, 12r, 13a, 13f, 14c, 14f, and 14g had a purity of 98%. Compounds 5e, 5n, 5r, 5u, 5bb, 5ee, 5hh, 5ll, 4e, 4 pp, 12c, 12d, 12e, 12h, 14b, 14h, and 14i had a purity of 97%. Compounds 5b, 5c, 5d, 5p, 5l, 5x, 5z, 5kk, 5nn, 4s, 4rr, 4w, 4bb, 4hh, 4ii, 12b, 12j, 12o, 13c, and 13e had a purity of 96%. Compounds 5a, 5m, 5q, 5s, 5cc, 5dd, 5oo, 4o, 13d, 13g, 13h, 13i, and 14e had a purity of 95%. Purity of each compound was determined on an Agilent 1100 LC/MS instrument on a ZORBAX® SB-C18, 3.5 mm, 4.6× 50, a flow rate of 0.75 mL/min, detection at 220 and 254 nm, with a 10-98% acetonitrile/water/0.1% formic acid gradient and a 50-98% acetonitrile/water/0.1% formic acid gradient. FAAH Inhibition. $^{14}$C-labeled oleamide was prepared from $^{14}$C-labeled oleic acid as described (Cravatt, B. F.; et al. *Science* 1995, 268, 1506-1509). The truncated rat FAAH (rFAAH) was expressed in *E. coli* and purified as described (Patricelli, M. P.; Lashuel, H. A.; et al. *Biochemistry* 1998, 37, 15177-15187). The purified recombinant rFAAH was used in the inhibition assays unless otherwise indicated. The full-length human FAAH (hFAAH) was expressed in COS-7 cells as described (Giang, D. K.; Cravatt, B. F. *Proc. Natl. Acad. Sci. U.S.A.* 1997, 94, 2238-2242), and the lysate of hFAAH-transfected COS-7 cells was used in the inhibition assays where explicitly indicated.

The inhibition assays were performed as described (Cravatt, B. F.; et al. *Science* 1995, 268, 1506-1509). In brief, the enzyme reaction was initiated by mixing 1 nM of rFAAH (800, 500, or 200 pM rFAAH for inhibitors with $K_i \leq 1$-2 nM) with 10 μM of $^{14}$C-labeled oleamide in 500 μL of reaction buffer (125 mM TrisCl, 1 mM EDTA, 0.2% glycerol, 0.02% Triton X-100, 0.4 mM Hepes, pH 9.0) at room temperature in the presence of three different concentrations of inhibitor. The enzyme reaction was terminated by transferring 20 μL of the reaction mixture to 500 μL of 0.1 N HCl at three different time points. The $^{14}$C-labeled oleamide (substrate) and oleic acid (product) were extracted with EtOAc and analyzed by TLC as detailed (Cravatt, B. F.; et al. *Science* 1995, 268, 1506-1509). The $K_i$ of the inhibitor was calculated using a Dixon plot as described (standard deviations are provided in the Supporting Information tables) (Boger, D. L.; Sato, H.; et al. *Proc. Natl. Acad. Sci. U.S.A.* 2000, 97, 5044-5049). Lineweaver-Burk analysis was performed as described confirming competitive, reversible inhibition (Boger, D. L.; Miyauchi, H.; et al. *J. Med. Chem.* 2005, 48, 1849-1856).

What is claimed is:
1. A compound having the following structure:

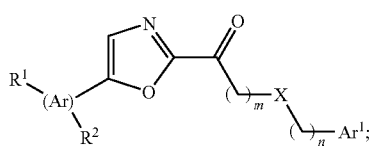

wherein Ar is a phenyl or pyridyl having a carbon as its point of attachment to the oxazole;
R$^1$ is independently selected from the group consisting of hydrogen, —(C$_1$-C$_6$ alkyl), —(C$_3$-C$_6$ alkyl), —CF$_3$, —CN, —C(O)C$_1$-C$_4$ alkyl optionally substituted with one, two, or three fluoro substituents, —CO$_2$(C$_1$-C$_4$ alkyl), —CO$_2$H, —C(O)N(R$^a$)R$^b$, —OH, —O(C$_1$-C$_6$ alkyl), halo, —NO$_2$, —NR$^a$R$^b$, —N(R$^a$)C(O)R$^b$, —N(R$^a$)SO$_2$R$^b$, —SO$_2$N(R$^a$)R$^b$, —SR$^a$, —S(O)R$^a$, and —SO$_2$R$^a$;

where R$^a$ and R$^b$ are each independently selected from the group consisting of —H, —(C$_1$-C$_6$ alkyl), and —(C$_3$-C$_6$ cycloalkyl); and
R$^2$ is independently selected from the group consisting of hydrogen, —(C$_1$-C$_6$ alkyl), —(C$_3$-C$_6$ alkyl), —CF$_3$, —CN, —C(O)C$_1$-C$_4$ alkyl optionally substituted with one, two, or three fluoro substituents, —CO$_2$(C$_1$-C$_4$ alkyl), —CO$_2$H, —C(O)N(R$^c$)R$^d$, —OH, —O(C$_1$-C$_6$ alkyl), -halo, —NO$_2$, —NR$^c$R$^d$, —N(R$^c$)C(O)R$^d$, —N(R$^c$)SO$_2$R$^d$, —SO$_2$N(R$^c$)R$^d$, —SR$^C$, —S(O)R$^C$, —SO$_2$R$^c$;
where R$^c$ and R$^d$ are each independently selected from the group consisting of —H, —(C$_1$-C$_6$ alkyl), and —(C$_3$-C$_6$ cycloalkyl); and
Ar$^1$ is selected from the group consisting of:

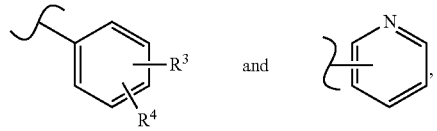

X is selected from the group of diradicals consisting of —CH$_2$—, —O—, —S—, —S(O)—, —S(O)$_2$—, —NR$^5$—, —CH(OH)—, and —C(O)NH—; and
R$^3$ is selected from the group consisting of —NHBOC, —Cl, —Br, —I, —NH$_2$, —NO$_2$, —O(C$_1$-C$_6$ alkyl), —S(C$_1$-C$_6$ alkyl), —S(O)(C$_1$-C$_6$ alkyl), —S(O)$_2$(C$_1$-C$_6$ alkyl), —CF$_3$, —COOH, and —CO$_2$(C$_1$-C$_6$ alkyl);
R$^4$ is selected from the group consisting of —H, —NHBOC, —Cl, —Br, —I, —NH$_2$, —NO$_2$, —O(C$_1$-C$_6$ alkyl), —S(C$_1$-C$_6$ alkyl), —S(O)(C$_1$-C$_6$ alkyl), —S(O)$_2$(C$_1$-C$_6$ alkyl), —CF$_3$, —COOH, and —CO$_2$(C$_1$-C$_6$ alkyl); and
R$^5$ is selected from the group consisting —H, and —(C$_1$-C$_6$ alkyl); and
Z is selected from the group of diradicals consisting of —O—, —S—, and —NR$^5$—; and
m is an integer between 0 and 6; and
n is an integer between 0 and 6;
with the following provisos:
if m is 0, then n cannot be 0; and
if X is —CH$_2$—, then Ar$^1$ cannot be phenyl;
or a pharmaceutically acceptable salt thereof.
2. A compound according to claim 1, wherein Ar is selected from the group consisting of the following

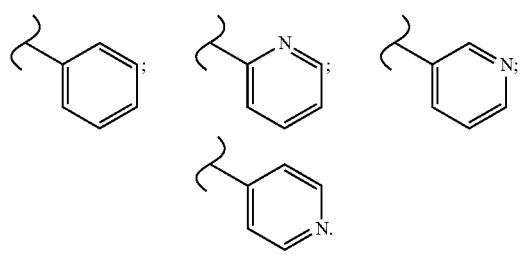

3. A compound according to claim 1, wherein R$^1$ is selected from the group consisting of —CH$_3$, —CF$_3$, —CN, —C(O)CF$_3$, —CO$_2$CH$_3$, —CO$_2$H, —C(O)NH$_2$, —OH, —OCH$_3$, —F, —NO$_2$, —NH$_2$, and —SO$_2$NH$_2$.
4. A compound according to claim 1, wherein R$^2$ is —H.
5. A compound according to claim 2, wherein R$^1$ is selected from the group consisting of —CH$_3$, —CF$_3$, —CN, —C(O)

CF₃, —CO₂CH₃, —CO₂H, —C(O)NH₂, —OH, —OCH₃, —F, —NO₂, —NH₂, and —SO₂NH₂.

6. A compound according to claim 2, wherein R² is —H.

7. A compound according to claim 2, wherein R¹ is selected from the group consisting of —CH₃, —CF₃, —CN, —C(O)CF₃, —CO₂CH₃, —CO₂H, —C(O)NH₂, —OH, —OCH₃, —F, —NO₂, —NH₂, and —SO₂NH₂.

8. A compound according to claim 2, wherein R² is —H.

9. A compound according to claim 7, wherein R² is —H.

10. A compound according to claim 1, having the following structure:

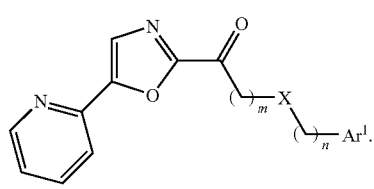

11. A compound according to claim 10, having any of the following structures, or a pharmaceutically acceptable salt thereof:

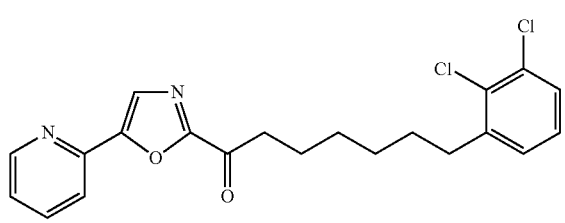

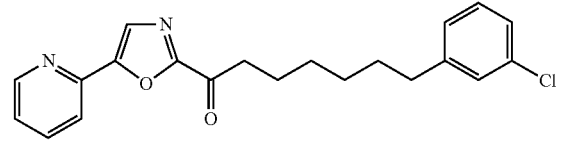

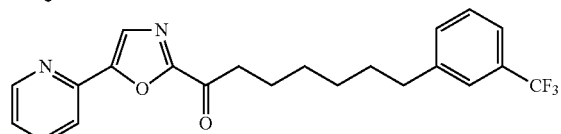

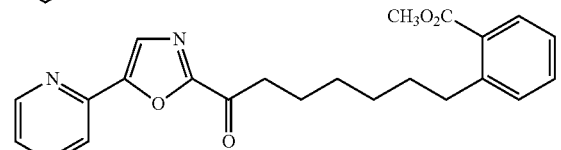

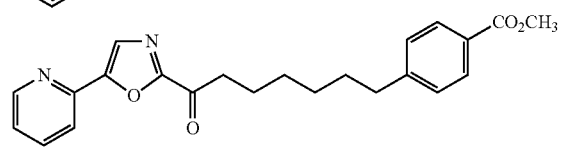

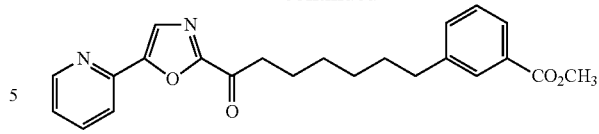

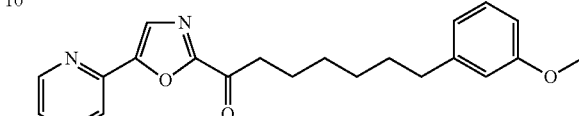

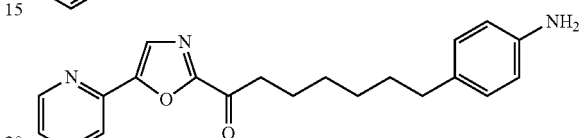

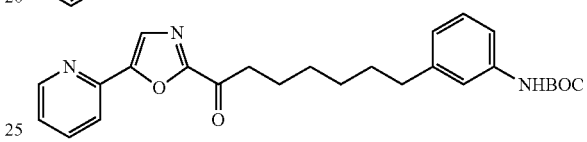

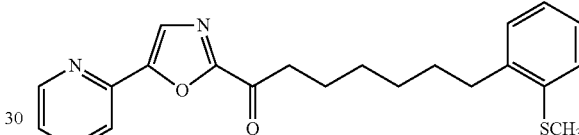

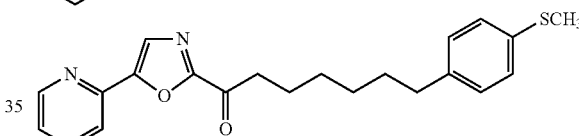

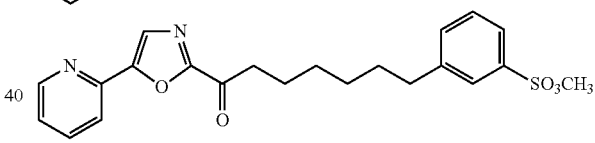

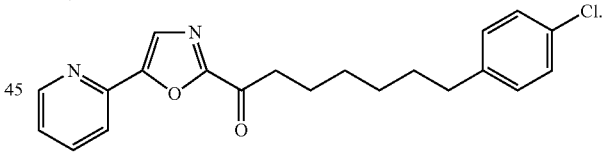

12. A pharmaceutical composition comprising a compound of claim 1 and a pharmaceutically acceptable carrier.

13. A pharmaceutical combination comprising a compound of claim 1 in combination with another FAAH modulator or another biologically active agent.

14. A pharmaceutical combination of claim 13 wherein the active ingredient is an opiod, an NSAID, gabapentin, pregabalin, tramadol, acetaminophen or aspirin.

* * * * *

UNITED STATES PATENT AND TRADEMARK OFFICE
CERTIFICATE OF CORRECTION

| | |
|---|---|
| PATENT NO. | : 8,124,778 B2 |
| APPLICATION NO. | : 12/600736 |
| DATED | : February 28, 2012 |
| INVENTOR(S) | : Dale L. Boger |

It is certified that error appears in the above-identified patent and that said Letters Patent is hereby corrected as shown below:

On the face page, in field (57), under "Abstract", in column 2, line 5, delete "arc" and insert -- are --, therefor.

In column 1, lines 53-54, delete "arachidonoyl" and insert -- arachidonyl --, therefor.

In column 2, lines 65-66, delete "benzodiazepene" and insert -- benzodiazepine --, therefor.

In column 4, line 15, delete "triacylglyceride" and insert -- triacylglycerol --, therefor.

In column 7, line 65, delete "$R^6=(C_1-C_6$ alkyl)." and insert -- $R^6=(C_1-C_6$ alkyl). --, therefor.

In column 8, line 46, delete "pruritis," and insert -- pruritus, --, therefor.

In column 9, line 37, delete "napthyl," and insert -- naphthyl, --, therefor.

In column 9, line 48, delete "X=S," and insert -- X=S, --, therefor.

In column 12, line 46, delete "Propertions," and insert -- Properties, --, therefor.

In column 13, line 58, delete "isodemosine," and insert -- isodesmosine, --, therefor.

In column 13, line 59, delete "norvalin," and insert -- norvaline, --, therefor.

In column 15, line 25, delete "neurogenerative" and insert -- neurodegenerative --, therefor.

In column 20, line 53, delete "4o-4-s," and insert -- 4o-4s, --, therefor.

In column 20, line 54, delete "4x-4 cc, 4gg-4-jj" and insert -- 4x-4cc, 4gg-4jj --, therefor.

Signed and Sealed this
Twenty-eighth Day of August, 2012

David J. Kappos
*Director of the United States Patent and Trademark Office*

In column 21, line 17, delete "13c." and insert -- 13e. --, therefor.

In column 21, line 47, delete "substitutent" and insert -- substituent --, therefor.

In column 21, line 67, delete "potency." and insert -- potency --, therefor.

In column 22, line 6, delete "(R=Cl)" and insert -- (R=Cl) --, therefor.

In column 22, line 18, delete "Shonogashira" and insert -- Sonogashira --, therefor.

In column 22, lines 28-29, delete "substitutents" and insert -- substituents --, therefor.

In column 22, line 33, delete "(X=S," and insert -- (X=S, --, therefor.

In column 22, line 35, delete "(X=$SO_2$, 12d)" and insert -- (X=$SO_2$, 12d) --, therefor.

In column 24, line 42, delete "$^1$NMR" and insert -- $^1$H NMR --, therefor.

In column 24, line 66, delete "□8.68" and insert -- δ8.68 --, therefor.

In column 25, line 3, delete "□187.9," and insert -- δ187.9, --, therefor.

In column 25, line 65, delete "□8.68" and insert -- δ8.68 --, therefor.

In column 26, line 2, delete "□188.4," and insert -- δ188.4, --, therefor.

In column 31, line 43, delete "(t, 211," and insert -- (t, 2H, --, therefor.

In column 49, line 22, before "1-Oxo" delete "b".

In column 53, line 24, delete "(5 ft)." and insert -- (5ff). --, therefor.

In column 53, line 26, delete "(5 cc)" and insert -- (5cc) --, therefor.

In column 64, line 24, delete "(m, 11H)." and insert -- (m, 1H). --, therefor.

In column 67, line 20, delete "Cert-" and insert -- tert- --, therefor.

In column 78, line 66, delete "$H^+$requires" and insert -- $H^+$ requires --, therefor.

In column 80, line 45, delete

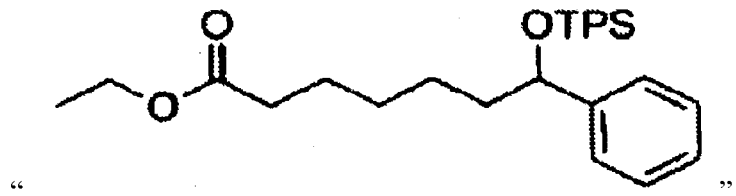
" "

and insert

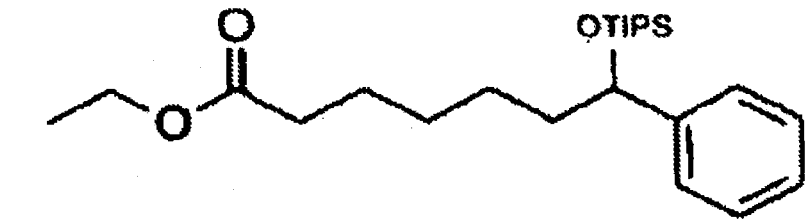
-- --, therefor.

In column 83, line 10, delete "($C_{10}H_2N_2O_2Cl+H^+$" and insert -- ($C_{10}H_7N_2O_2Cl+H^+$ --, therefor.

In column 84, line 52, delete "showns" and insert -- shows --, therefor.

In column 84, line 67, delete "4 cc," and insert -- 4cc, --, therefor.

In column 85, line 4, delete "4 pp," and insert -- 4pp, --, therefor.

In column 85, line 5, delete "5l," and insert -- 5t, --, therefor.

In column 85, line 58, in Claim 1, after "is" delete "a".

In column 86, line 10, in Claim 1, delete "—$SR^C$, —$S(O)R^C$," and insert -- —$SR^c$, —$S(O)R^c$, --, therefor.

In column 86, line 20, in Claim 1, delete " 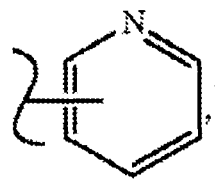 " and insert

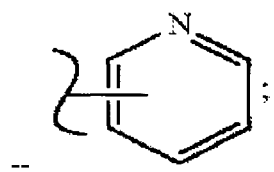
-- --, therefor.

CERTIFICATE OF CORRECTION (continued)
U.S. Pat. No. 8,124,778 B2

In column 88, line 45, in Claim 12, delete

" 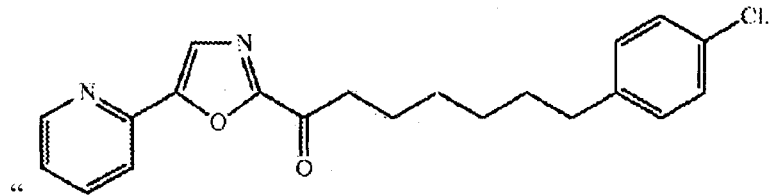 " and insert

-- 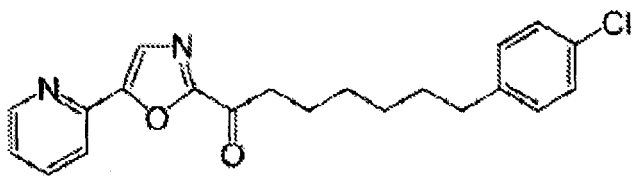

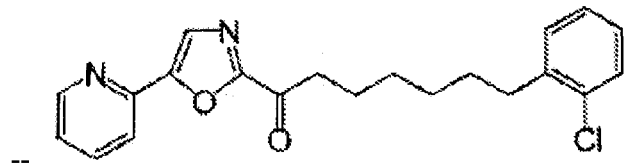 --, therefor.

In column 88, line 55, in Claim 14, delete "opiod," and insert -- opioid, --, therefor.